(12) United States Patent
Barve et al.

(10) Patent No.: US 12,708,457 B1
(45) Date of Patent: Aug. 18, 2026

(54) APPARATUS AND METHOD FOR LOCALIZATION ASSOCIATED WITH AORTIC VALVE REPAIR USING TRANSESOPHAGEAL ECHOCARDIOGRAPHY

(71) Applicant: Anumana, Inc., Cambridge, MA (US)

(72) Inventors: Rakesh Barve, Bengaluru (IN); Suthirth Vaidya Subramany, Bengaluru (IN); Animesh Agarwal, San Mateo, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 19/295,844

(22) Filed: Aug. 11, 2025

(51) Int. Cl.

| | |
|---|---|
| ***A61B 34/20*** | (2016.01) |
| ***A61B 8/08*** | (2006.01) |
| ***A61B 8/12*** | (2006.01) |
| ***A61F 2/24*** | (2006.01) |
| *A61B 90/00* | (2016.01) |
| *A61M 25/01* | (2006.01) |

(52) U.S. Cl.
CPC ............ *A61B 34/20* (2016.02); *A61B 8/0883* (2013.01); *A61B 8/12* (2013.01); *A61F 2/2427* (2013.01); *A61B 2034/2063* (2016.02); *A61B 2034/2065* (2016.02); *A61B 2090/364* (2016.02); *A61B 2090/3782* (2016.02); *A61M 2025/0166* (2013.01)

(58) Field of Classification Search
CPC .......... A61B 8/0883; A61B 2034/2063; A61B 2090/3782; A61M 2025/0166
See application file for complete search history.

(56) References Cited

U.S. PATENT DOCUMENTS

| | | | | |
|---|---|---|---|---|
| 5,713,950 | A * | 2/1998 | Cox | A61L 27/507 435/238 |
| 2011/0153286 | A1* | 6/2011 | Zaeuner | G06T 19/00 703/1 |
| 2013/0150710 | A1* | 6/2013 | Zentgraf | A61B 8/461 600/424 |
| 2014/0052241 | A1 | 2/2014 | Harks et al. | |
| 2018/0256131 | A1* | 9/2018 | Bracken | A61B 8/12 |
| 2019/0015203 | A1 | 1/2019 | Kheradvar | |
| 2020/0261157 | A1 | 8/2020 | Chen et al. | |
| 2024/0315779 | A1* | 9/2024 | Pai Raikar | A61B 34/20 |

FOREIGN PATENT DOCUMENTS

| | | | |
|---|---|---|---|
| CN | 118634033 | A1 | 9/2024 |
| WO | 2023133592 | A1 | 7/2023 |

* cited by examiner

*Primary Examiner* — Rochelle D Turchen
(74) *Attorney, Agent, or Firm* — CALDWELL LLC

(57) ABSTRACT

An apparatus for localization associated with aortic valve repair using transesophageal echocardiography, wherein the apparatus includes a probe configured to capture images of an aortic valve pertaining to a subject, a delivery system including a delivery catheter configured for aortic valve repair, and a computing device configured to receive a 3D model representative of the aortic valve, receive an initial set of images from the Probe, wherein the Probe is located within an esophagus of the subject, identify a position of the Probe and the delivery system by identifying anatomical landmarks within the initial set of images and locating the position of the Probe and the delivery system relative to the anatomical landmarks and display the position of the delivery system relative to the 3D model.

14 Claims, 16 Drawing Sheets

1004
1000c
1020

APPARATUS AND METHOD FOR LOCALIZATION ASSOCIATED WITH AORTIC VALVE REPAIR USING TRANSESOPHAGEAL ECHOCARDIOGRAPHY

FIELD OF THE INVENTION

The present invention generally relates to the field of medical imaging. In particular, the present invention is directed to an apparatus and method for localization associated with aortic valve repair using transesophageal echocardiography.

BACKGROUND

Aortic valve procedures may be performed to treat conditions such as aortic stenosis or aortic regurgitation. Existing systems or processes associated with aortic valve procedures often lack the capability to accurately localize and position prosthetic devices or imaging device within the left side of the heart, thus limiting a medical professional's ability to plan and guide device placement during aortic valve interventions. A precise reconstruction of heart anatomy, including clear identification of catheters and prosthetic devices, is critically important for achieving safe and effective outcomes in procedures involving the aortic valve.

SUMMARY OF THE DISCLOSURE

In an aspect, an apparatus for localization associated with aortic valve repair using transesophageal echocardiography is described. The apparatus includes a transesophageal echocardiography (TEE) probe configured to capture TEE images of an aortic valve pertaining to a subject and a delivery system including a delivery catheter configured for aortic valve repair. The apparatus further includes a computing device configured to receive a 3D model representative of the aortic valve, receive an initial set of TEE images from the TEE probe, identify a position of the TEE probe and the delivery system by identifying anatomical landmarks within the initial set of TEE images and locating the position of the TEE probe and the delivery system relative to the anatomical landmarks and display the position of the delivery system relative to the 3D model.

In another aspect, a method for localization associated with aortic valve repair using transesophageal echocardiography is described, the method includes receiving, by at least a processor, a 3D model representative of an aortic valve, receiving, by the at least a processor and a transesophageal echocardiography (TEE) probe, an initial set of TEE images wherein the TEE probe is configured to capture TEE images of the aortic valve pertaining to a subject and the TEE probe is further configured to capture a delivery system, wherein the delivery system includes a delivery catheter configured for aortic valve repair. The method further includes identifying, by the at least a processor, a position of the TEE probe and the delivery system by identifying anatomical landmarks within the initial set of TEE images and locating the position of the TEE probe and the delivery system relative to the anatomical landmarks and displaying, by the at least a processor, the position of the delivery system relative to the 3D model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

Figure 1:
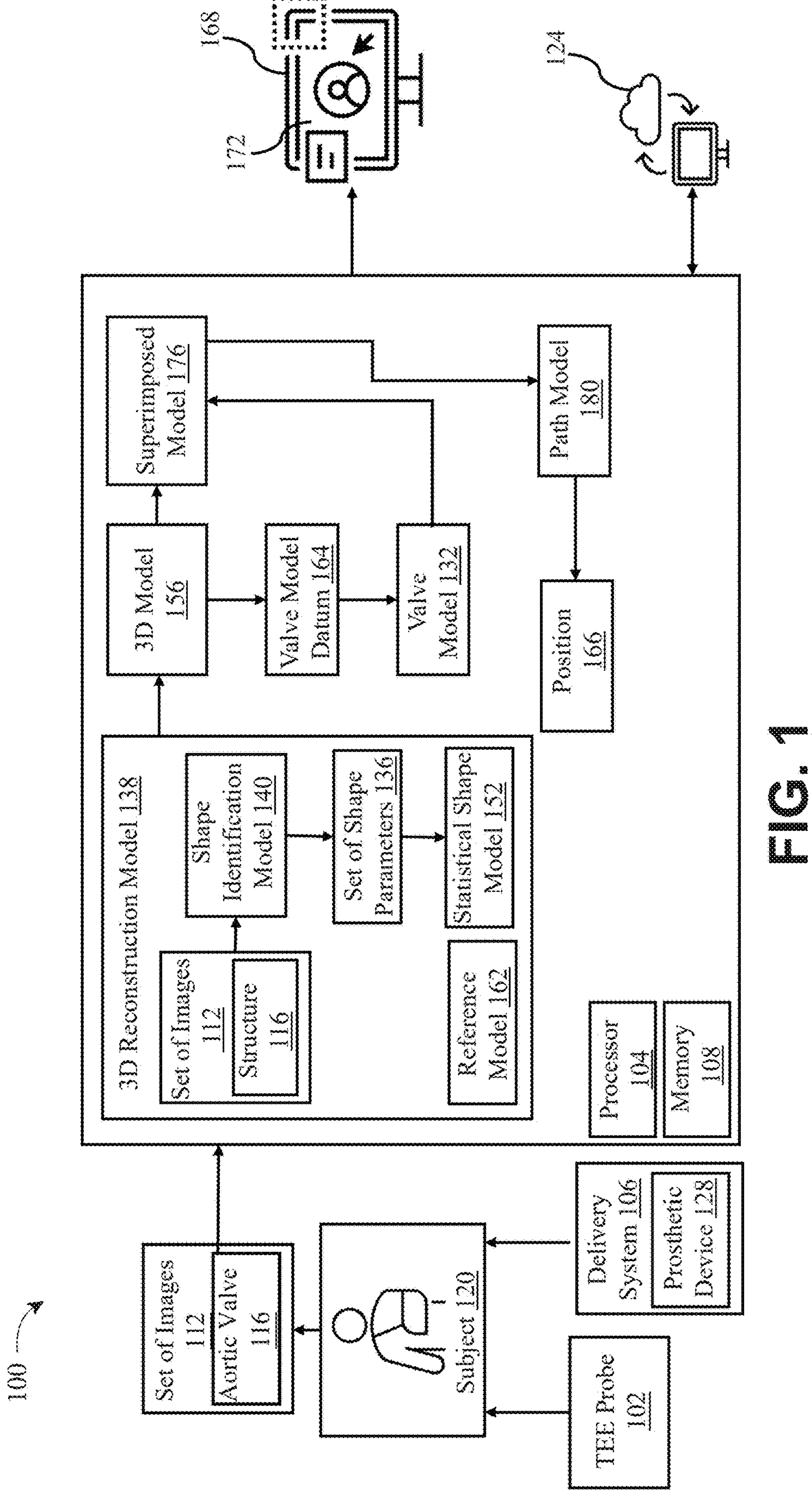
FIG. 1 is a block diagram of an exemplary embodiment of an apparatus for localization associated with aortic valve repair using transesophageal echocardiography.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

The present disclosure generally relates to aortic valve surgery and associated interventional procedures. Aspects of the present disclosure include the utilization of a 3D model in order to localize TEE probes and delivery systems. Aspects of the present disclosure may facilitate in procedures associated with mitral valve repair. Aspects of the present disclosure may be utilized independently or in combination with any of the surgical or interventional techniques described herein, including but not limited to valve repair, valve replacement, and/or transcatheter procedures.

The aortic valve is one of the four cardiac valves and is positioned between the left ventricle and the aorta. Its role is to permit unidirectional blood flow from the heart into the aorta while preventing retrograde flow. Structurally, the aortic valve includes three cusps that open during systole and close during diastole. Aortic valve procedures may be indicated for the treatment of conditions such as aortic regurgitation or aortic stenosis. Regurgitation refers to incomplete valve closure allowing backflow into the left ventricle, while stenosis is characterized by narrowing that restricts forward flow into the aorta. Treatment may involve either repair or replacement of the valve. Access to the aortic valve for surgical or interventional procedures can be achieved through various routes, including full sternotomy, partial sternotomy, thoracotomy, mini-thoracotomy, robotically assisted access, video-assisted thoracic surgery, and transcatheter techniques. Surgical approaches generally involve incisions of greater size than those used for transcatheter procedures, and commonly employ cardiopulmonary bypass. In contrast, transcatheter approaches typically proceed without the use of heart-lung bypass. Surgical access allows for direct visualization and manipulation of cardiac structures, whereas transcatheter procedures rely on fluoroscopic and echocardiographic guidance. Differences in these access methods may influence post-procedural recovery times, with larger surgical incisions often requiring longer healing periods compared to transcatheter entry points.

Traditional surgical access is commonly achieved via full median sternotomy, which involves a midline incision to divide the sternum and expose the heart. Cardiopulmonary bypass is established to facilitate the removal and replacement of the valve. Upon completion, the sternum is reapproximated and secured with sternal wires. This method allows for extensive exposure of the cardiac structures. Modifications to sternotomy include partial upper sternotomy, J-shaped sternotomy, and right anterior thoracotomy, which reduce the extent of sternotomy while maintaining operative access. Robot-assisted surgery may also be employed, in which instruments are inserted through small incisions and manipulated by robotic systems under surgeon control. Transcatheter access routes are selected based on anatomical and clinical considerations. The transfemoral route, which accesses the valve via the femoral artery, is the most frequently used. The catheter is advanced retrograde from the groin to the aortic valve and the procedure is conducted under imaging guidance. When transfemoral access is not viable, alternate routes include transapical (via the apex of the left ventricle), transaortic (via the ascending aorta), trans-subclavian or trans-axillary (via arteries under the collarbone or in the armpit), transcarotid (via the neck), and transcaval (via a connection created between the vena cava and the aorta). Each of these alternatives is chosen based on patient-specific anatomical features and may involve either direct aortic access or remote arterial entry.

Repair of the aortic valve, rather than replacement, may be selected to preserve native valve structures. Repair is considered in aortic regurgitation and conditions involving aortic root pathology, particularly in patients where valve preservation may be advantageous due to factors such as age or structural integrity. Specific anatomical presentations include Type I regurgitation (dilation of the aortic root or sinotubular junction), Type II regurgitation (cusp prolapse), and those involving bicuspid valves with suitable tissue morphology. Additional indications may include aortic root aneurysms with structurally intact cusps, infective endocarditis with limited tissue destruction, and cases in pediatric or young adult patients. Contraindications to aortic valve repair include the presence of significant cusp calcification or retraction, active infective endocarditis with widespread destruction, insufficient cusp tissue, severe aortic stenosis with heavy calcification, certain connective tissue disorders, and cases involving limited life expectancy where procedural complexity does not yield long-term benefit.

Techniques employed in aortic valve repair include annuloplasty, leaflet procedures, edge-to-edge repair, chordal replacement, and aortic aneurysm repair. Annuloplasty involves the placement of a prosthetic ring or suture-based constructs (e.g., De Vega annuloplasty) to reduce annular dimensions and restore cusp coaptation. Ring annuloplasty may employ rigid or semi-rigid devices, anchored with pledgeted or continuous sutures. Leaflet procedures address prolapse, tethering, or perforation through resection, plication, or use of artificial chordae. Commissurotomy is performed by incising fused commissures to relieve stenosis. Leaflet repair may include the use of pericardial or synthetic patches to close perforations, reshaping of cusps through resection, resuspension of prolapsed leaflets, and decalcification of mildly affected tissue. Edge-to-edge repair includes techniques such as the Alfieri stitch, which approximates leaflet edges to reduce regurgitant orifice area. This surgical method has influenced the development of percutaneous equivalents. Repair techniques may also incorporate valvuloplasty, either balloon-based or surgical. Balloon valvuloplasty is executed via catheter, typically inserted through a peripheral vessel and guided into the stenotic valve, where the balloon is inflated to enlarge the orifice. Surgical valvuloplasty is conducted during open-heart surgery and may involve decalcification, leaflet reshaping, or annuloplasty. Aortic root aneurysm repair may be performed in conjunction with valve preservation. Valve-sparing root replacement involves excising the aneurysmal root and replacing it with a graft while retaining the native valve. The Yacoub (remodeling) and David (reimplantation) techniques are established methods for this procedure. The remodeling technique replaces the aortic root with a scalloped graft, while the reimplantation method involves securing the valve within a tubular graft. Additionally, thoracic endovascular aortic repair (TEVAR) may be employed to treat aneurysms or dissections in the thoracic aorta by deploying a stent-graft through an endovascular approach.

Aortic valve replacement involves the substitution of a patient's native aortic valve with a prosthetic valve. This procedure is generally performed when the valve is no longer suitable for repair due to pathology such as aortic regurgitation, aortic stenosis, infective endocarditis, rheumatic heart disease, or congenital malformations. It serves as the definitive intervention for severe aortic valve disease when clinical symptoms or specific echocardiographic thresholds are present. Replacement is indicated in symptomatic individuals with severe aortic stenosis, regardless of left ventricular ejection fraction. Echocardiographic criteria for severe aortic stenosis typically include a valve area less than 1.0 $cm^2$, a mean transvalvular gradient greater than 40 mmHg, or a peak aortic jet velocity exceeding 4.0 meters per second. In asymptomatic individuals, replacement is considered when the left ventricular ejection fraction is less than 50%, when concurrent cardiac surgical procedures are required, in cases of very severe stenosis (velocity ≥5.0 m/s), or when abnormal findings are observed during exercise testing. Severe aortic regurgitation is also an indication when symptoms are present, or in asymptomatic cases where the left ventricular ejection fraction is 55% or lower, or the end-systolic dimension exceeds 50 mm or is indexed at 25 mm/m$^2$ or more. Additional indications include infective endocarditis associated with structural destruction, persistent infection, or hemodynamically significant vegetations, as well as cases involving bicuspid aortic valves in the presence of aortic root or ascending aorta aneurysms greater than 4.5 to 5.0 cm in diameter. Prosthetic valve failure, including stenosis or regurgitation of bioprosthetic devices, also necessitates replacement. Contraindications to aortic valve replacement include active non-cardiac infection that cannot be adequately managed, prohibitively high surgical risk without access to transcatheter alternatives, and comorbid conditions that significantly limit life expectancy to under one year, such as terminal malignancy, severe cognitive impairment, or advanced pulmonary fibrosis. Relative contraindications may include advanced frailty, severe fixed pulmonary hypertension, non-compliance with anticoagulation requirements (in the case of mechanical valves), and extensive aortic root disease that cannot be surgically corrected.

The selection between surgical and transcatheter approaches is based on factors such as procedural risk stratification, patient age, anticipated life expectancy, anatomical considerations, and valve morphology. Transcatheter aortic valve replacement (TAVR) is typically utilized in patients aged 75 years or older who are at high or intermediate risk for surgical intervention. Surgical aortic valve replacement (SAVR) is generally preferred in younger individuals under the age of 65, in cases involving bicuspid valve morphology, active endocarditis, or when other open cardiac procedures are concurrently required.

Prosthetic valves used in replacement procedures generally fall into two categories: mechanical and bioprosthetic. Mechanical valves are fabricated from durable materials such as titanium or carbon and are designed for long-term function, often exceeding 20 years. Patients receiving mechanical valves are typically prescribed lifelong anticoagulation therapy to mitigate thromboembolic risk. Bioprosthetic valves, constructed from porcine, bovine, or human tissue, generally offer functional durations of 10 to 15 years and do not commonly necessitate chronic anticoagulation.

Aortic valve replacement may be conducted via open-heart surgery, minimally invasive surgery, or transcatheter techniques. Open-heart surgery involves a median sternotomy, the use of cardiopulmonary bypass, excision of the native valve, and sutured placement of the prosthetic valve. This approach provides full exposure of the cardiac structures and is often selected for complex or combined procedures. Minimally invasive surgery may be performed through smaller intercostal incisions, such as mini-thoracotomies, and may incorporate specialized instrumentation or robotic assistance. This method also generally requires cardiopulmonary bypass. Compared to full sternotomy, minimally invasive approaches may reduce surgical trauma and potentially shorten hospitalization and recovery time. Transcatheter aortic valve replacement involves the deployment of a prosthetic valve via catheter-based delivery systems. The most common access point is transfemoral, through the femoral artery, although alternative routes such as transapical, transaortic, or trans-subclavian may be employed based on anatomical or clinical considerations. The transcatheter valve, once navigated into position within the native annulus, is expanded using either balloon inflation or self-expanding technology, displacing the native leaflets and assuming functional regulation of blood flow from the left ventricle to the aorta. Transcatheter heart valves generally consist of a stent frame, bioprosthetic leaflets, a sealing skirt, and radiopaque markers. The frame provides structural support and is typically constructed from self-expanding alloys such as nitinol, or balloon-expandable metals such as cobalt-chromium or stainless steel. The leaflets are derived from bovine or porcine pericardial tissue and mimic native valve function. A skirt made from synthetic fabric, such as polyethylene terephthalate (PET), forms a seal at the annulus to reduce paravalvular leakage. Radiopaque markers aid in positioning under fluoroscopic imaging. TAVR procedures rely on advanced imaging modalities including fluoroscopy and echocardiography to ensure accurate deployment, and may involve auxiliary devices such as guidewires, delivery catheters, and embolic protection systems.

In one or more embodiments, aspects of the present disclosure may describe procedures and/or prosthetic devices consistent with the procedures and/or prosthetic devices as described above.

Referring now to FIG. 1, an exemplary embodiment of an apparatus 100 localization associated with aortic valve repair using transesophageal echocardiography is described. Aortic valve repair" as describe herein refers to any surgical or transcatheter procedure performed to restore the function, structure, or integrity of the native aortic valve. In one or more embodiments, aortic valve repair may include the inclusion of a prosthetic device to restore function to an aortic valve and/or the complete replacement of an aortic valve with a prosthetic device. In one or more embodiments, aortic valve repair may include any medical procedure associated with the aortic valve as described in this disclosure.

With continued reference to FIG. 1, apparatus 100 includes an ultrasound imaging device. An "ultrasound imaging device" for the purposes of this disclosure is a device capable of capturing ultrasonic images. In one or more embodiments, ultrasound imaging device includes a TEE probe 102 (endoscope) and/or a transesophageal echocardiography imaging device as described in reference to at least FIG. 9. The ultrasound probe is a long, flexible device equipped with an ultrasound transducer (ultrasound sensor) at its tip. Ultrasound transducer can emit high-frequency sound waves and capture the echoes reflected from cardiac structures to produce detailed images (e.g., set of images). In a non-limiting example, ultrasound probe may be inserted into the patient's esophagus, where the ultrasound probe may be connected to an ultrasound machine, which processes signals from ultrasound transducer to generate images of the heart. In one or more embodiments, ultrasound imaging device may be communicatively connected to at least a display. The display disclosed herein is further described in detail below. Additional disclosure related to ultrasound imaging device is further described in detail below.

With continued reference to FIG. 1, ultrasound imaging device may include at least an ultrasound sensor configured to be located within an esophagus of a patient and detect at least an ultrasound image. In one or more embodiments, one or more ultrasound images may be used to generate set of images as described in further detail below. In one or more embodiments, ultrasound sensor may be configured to capture one or more ultrasound images of subject. For the purposes of this disclosure, an "ultrasound sensor" is a device that uses ultrasonic waves to detect the presence and distance of objects. In a non-limiting example, ultrasound sensor May measure the distance to an object using ultrasonic sound waves. For the purposes of this disclosure, a "sensor" is a device that produces an output signal for the purpose of sensing a physical phenomenon. For example, and without limitation, sensor may transduce a detected phenomenon, such as without limitation, temperature, voltage, current, pressure, speed, motion, light, moisture, sound waves, and the like, into a sensed signal. Sensor may output the sensed signal. Sensor may include any computing device as described in the entirety of this disclosure and configured to convert and/or translate a plurality of signals detected into electrical signals for further analysis and/or manipulation. Electrical signals may include analog signals, digital signals, periodic or aperiodic signal, step signals, unit impulse signal, unit ramp signal, unit parabolic signal, signum function, exponential signal, rectangular signal, triangular signal, sinusoidal signal, sine function, or pulse width modulated signal. Any datum captured by sensor may include circuitry, computing devices, electronic components or a combination thereof that translates into at least an electronic signal configured to be transmitted to another electronic component. In a non-limiting embodiment, sensor may include a plurality of sensors included in a sensor suite. In one or more embodiments, and without limitation, sensor may include a plurality of sensors. Sensor may include an ultrasound sensor.

With continued reference to FIG. 1, in one or more embodiments, ultrasound sensor may include an electrode. For the purposes of this disclosure, an "electrode" is a conductive material or element that facilitates the transmission and reception of electrical signals associated with ultrasound waves. In a non-limiting example, electrode may detect and record electrical activity; for instance, but not limited to, the heart's electrical signals. For example, and without limitation, electrode may generate ultrasonic sound waves, from which ultrasound sensor receives the ultrasonic waves and transmit ultrasound images related to the ultrasonic waves to processor 104. In one or more embodiments, ultrasound sensor may include a transducer. For the purposes of this disclosure, a "transducer" is a component of an ultrasound sensor that converts one form of energy into another. In a non-limiting example, transducer may operate on a principle of piezoelectricity, where piezoelectric material can convert electrical energy into mechanical vibration (i.e., ultrasonic waves) and vice versa. In one or more embodiments, ultrasound sensor may include a transceiver. For the purposes of this disclosure, a "transceiver" is a combined unit of a transmitter and a receiver. In a non-limiting example, transceiver may transmit ultrasonic waves and receive echoes.

With continued reference to FIG. 1, for the purposes of this disclosure, "ultrasound image" is a visual representation generated by reflection of high-frequency sound waves off internal body structures. In a non-limiting example, ultrasound image may include visual representation of a heart examined through esophagus of subject. As a non-limiting example, ultrasound image may include distance between sensor and surrounding tissue or organs. In one or more embodiments, ultrasound sensor may detect ultrasound image in a plurality of angles. In a non-limiting example, ultrasound image may include a plurality of distances between sensor and a heart in different angles. For example, without limitation, when ultrasound sensor moves around within an esophagus, ultrasound sensor receives a plurality of distances between ultrasound sensor and organ and generate ultrasound image using the plurality of distances.

With continued reference to FIG. 1, ultrasound imaging device includes a probe and may be used in conjunction with a transesophageal echocardiogram (TEE) system. In one or more embodiments, ultrasound imaging device may further include a catheter. In one or more embodiments, the probe may be integrated with a specialized TEE probe assembly designed for esophageal insertion. A "catheter" as described in this disclosure refers to any elongated, flexible instrument used in association with cardiovascular related procedures. In one or more embodiments, catheter may include a flexible instrument in which a probe is positioned and/or situated at a distal end of the flexible instrument. In one or more embodiments, a probe, such as a TEE probe 102 may be inserted into the esophagus to acquire cardiac images of subject. A "probe," also referred to as a "transducer probe" or a "transducer" in this disclosure, is a component that generates and receives ultrasound signals to create images of internal body structures. The probe may function as both a transmitter and a receiver of high-frequency sound waves. In one or more embodiments, a TEE probe 102 may include a probe used for transesophageal echocardiography. In one or more embodiments, a probe may contains piezoelectric crystals that deform when an electrical current is applied, emitting ultrasound waves into the body. Reflected waves from tissue and structural boundaries may then be converted by the crystals into electrical signals, which are processed into real-time images. In one or more embodiments, a TEE probe 102 includes a durable, waterproof housing that encloses piezoelectric elements, acoustic lens, backing material, and matching layers. The acoustic lens focuses ultrasound into a beam, and the backing material improves image resolution by dampening residual vibrations. The probe is connected to an ultrasound system via a cable, which supplies power and transmits signals for processing.

With continued reference to FIG. 1, ultrasound imaging device may be configured to capture ultrasound images of the aortic valve and related cardiac anatomy of a subject using transesophageal echocardiography (TEE) imaging and/or a TEE probe 102. In one or more embodiments, ultrasound images may be received as a set of images by processor 104, as described in further detail below. In one or more embodiments, ultrasound imaging device may be configured to capture real-time images and/or ultrasound data of the aortic valve and its surrounding anatomical features for diagnostic assessment or image-guided intervention during aortic valve repair.

With continued reference to FIG. 1, an ultrasound imaging device used in TEE may include a flexible probe that is inserted into the esophagus and advanced to obtain detailed ultrasound images of the heart and surrounding structures. The TEE probe 102 may provide near-field imaging of posterior cardiac structures, including the aortic valve, without requiring vascular access. In one or more embodiments, the TEE probe 102 allows for comprehensive visualization of the aortic valve leaflets, annulus, sinuses of Valsalva, and adjacent left ventricular outflow tract and ascending aorta. TEE imaging may also support color Doppler analysis to assess flow patterns, aortic regurgitation or stenosis, annular dimensions, and leaflet coaptation. In one or more embodiments, the ultrasound imaging device may be used during interventional aortic valve repair procedures, including surgical or transcatheter aortic valve replacement.

With continued reference to FIG. 1, the transducer and/or ultrasound imaging device may be positioned within the esophagus and/or stomach to achieve optimal imaging of the aortic valve through TEE imaging. In one or more embodiments, the probe may be advanced to mid-esophageal or trans-gastric positions to obtain views that allow comprehensive assessment of aortic valve structure and function. In one or more embodiments, the transducer may capture high-resolution images of the aortic valve leaflets, annulus, and surrounding left-sided heart structures. In one or more embodiments, the TEE probe 102 may be positioned to obtain long-axis or short-axis views of the left ventricular outflow tract, aortic valve, and ascending aorta, enabling precise evaluation of leaflet motion, calcification, annular dilation, and regurgitant or stenotic jets. In one or more embodiments, multiple imaging planes, including five-chamber, long-axis, and short-axis views, may be employed to fully characterize the anatomy and function of the aortic valve.

With continued reference to FIG. 1, ultrasound imaging device may be configured to capture images, such as set of images. In one or more embodiments, ultrasound imaging device includes a Transesophageal Echocardiography (TEE) imaging device. In one or more embodiments, set of images may include TEE images. "TEE images" as described in this disclosure refer to real-time or recorded ultrasound images of cardiac structures acquired using a transesophageal echocardiography system. TEE images may be obtained by positioning an ultrasound transducer (e.g., ultrasound imaging device) within the esophagus or stomach, posterior to the heart, thereby providing high-resolution acoustic access to various cardiac components, including but not limited to the atria, ventricles, cardiac valves, and proximal great vessels. TEE imaging may allow for the capture of multiple cross-sectional views (e.g., mid-esophageal, trans gastric, deep trans gastric, and upper esophageal) through manipulation of the probe and adjustment of imaging planes. In one or more embodiments, TEE images may include two-dimensional (2D), three-dimensional (3D), and Doppler-mode visualizations that assist in anatomical assessment, hemodynamic evaluation, and interventional guidance. In one or more embodiments, TEE images may be received from a transesophageal echocardiogram (TEE) imaging device. In one or more embodiments, TEE imaging device may be consistent with ultrasound imaging device. In one or more embodiments, TEE imaging device may include a TEE probe 102 configured to capture ultrasound images, set of images and/or the like as described in this disclosure. A "Transesophageal Echocardiography (TEE) imaging device" as described in this disclosure is an ultrasound system configured to obtain high-resolution images of the heart and surrounding structures by transmitting and receiving ultrasonic waves using a probe inserted into a patient's esophagus. The TEE imaging device may include an ultrasound transducer mounted on the tip of a flexible endoscopic probe, a control unit for probe manipulation, a signal processing unit, and a display interface. The TEE probe 102 may allow for detailed visualization of cardiac anatomy and function with reduced interference from surrounding tissues or air-filled lungs.

With continued reference to FIG. 1, apparatus 100 includes a delivery system 106. In one or more embodiments, delivery system 106 includes a catheter and a prosthetic device 128. In one or more embodiments, delivery system 106 is configured to route prosthetic device 128 through the body for use in aortic valve repair procedures, including surgical or transcatheter aortic valve replacement. A "delivery system" as described in this disclosure is a medical instrument designed to facilitate the navigation and delivery of a prosthetic device, such as an aortic valve prosthesis, through the vasculature to the heart. In one or more embodiments, delivery system 106 may include a flexible, steerable shaft that allows for controlled manipulation and precise placement of prosthetic device 128 at a target location, such as the aortic valve. In one or more embodiments, delivery system 106 may be used as part of a minimally invasive procedure for the implantation or repair of a prosthetic aortic valve. In one or more embodiments, delivery system 106 may be designed for ease of navigation through the cardiovascular system, including the femoral artery, and into the left side of the heart. In one or more embodiments, delivery system 106 may be made of biocompatible materials such as polyurethane, Pebax, and/or other suitable polymers. In one or more embodiments, delivery system 106 may include a catheter reinforced with a braided metal. In one or more embodiments, delivery system 106 may include a delivery catheter. A "delivery catheter" as described in this disclosure is a catheter configured to navigate a device within a subject. For example, and without limitation, the delivery catheter may be configured to navigate prosthetic device 128 to the aortic valve. In one or more embodiments, delivery system 106 may include a distal portion designed to hold a prosthetic valve and guide the prosthetic valve to a desired location. In one or more embodiments, at a distal tip of the catheter of delivery system 106, delivery system 106 may include a mechanism used to deploy or release the prosthetic valve once it reaches the target area, such as the aortic valve. In one or more embodiments, delivery system 106 may include sensors, such as pressure sensors or force sensors, to ensure accurate placement of prosthetic device 128. In one or more embodiments, sensors may provide real-time feedback to a user, such as a medical professional during an aortic valve repair procedure. In one or more embodiments, delivery system 106 may include embedded thermocouples or thermistors near a tip to monitor temperature during a procedure, ensuring that the device is positioned correctly. In one or more embodiments, the catheter of delivery system 106 may further include location tracking sensors to allow for precise tracking of movement of the catheter through the vasculature and to the heart. In one or more embodiments, delivery catheter is configured to perform aortic valve repair. In one or more embodiments, aortic valve repair may include any medical procedures associated with the aortic valve as described in this disclosure.

With continued reference to FIG. 1, ultrasound imaging device, such as, for example, a transesophageal echocardiography (TEE) imaging device, may be used to visualize the position and movement of the delivery system 106 within the heart by providing real-time ultrasound imaging (in the form of ultrasound data and/or an initial set of images) from within the esophagus and in close proximity to the heart. In one or more embodiments, ultrasound imaging device and/or processor 104 may generate cross-sectional views of the cardiac anatomy, including the left ventricular outflow tract, aortic root, ascending aorta, and valves, including the aortic valve, and/or other relevant structures. In one or more embodiments, ultrasound imaging device may be used to identify the position of delivery system 106 by capturing an initial set of images, which includes a region of interest, such as the left ventricular outflow tract or aortic valve, and identifying signatures that are representative of the delivery system. These signatures may appear as linear or point reflections depending on the imaging angle of the initial set of images. In one or more embodiments, continuous and/or dynamic tracking may be achieved by observing catheter movement in response to steering or manipulation and confirming its relation to cardiac structures. This may be done by capturing the initial set of images and subsequent images to ensure the accurate delivery of prosthetic device 128.

With continued reference to FIG. 1, delivery system 106 includes a catheter and a prosthetic device 128. The catheter may be consistent with any catheter and/or delivery catheter as described in this disclosure. A "prosthetic device" as described in this disclosure is a device used to replace or repair a damaged or diseased aortic valve in the heart. The aortic valve is responsible for ensuring unidirectional blood flow from the left ventricle to the aorta. When this valve fails to function properly due to conditions such as aortic stenosis or regurgitation, a prosthetic valve or repair device is employed to restore normal heart function. In one or more embodiments, prosthetic device 128 may either replace the valve entirely or aid in its repair. In one or more embodiments, prosthetic device 128 may include, but is not limited to, mechanical valves, biological (bioprosthetic) valves, and/or the like. In one or more embodiments, prosthetic device 128 may include devices for repair such as, for example, annuloplasty rings or bands, which are used to reshape and support the valve's annulus without complete replacement. In one or more embodiments, prosthetic device 128 may include any cardiovascular device as described in this disclosure. In one or more embodiments, prosthetic devices 128 may include transcatheter aortic valve replacement (TAVR) systems, leaflet repair technologies, and/or edge-to-edge repair devices suitable for the aortic valve. In one or more embodiments, prosthetic device 128 is situated at a distal end of delivery catheter.

With continued reference to FIG. 1, in one or more embodiments, prosthetic device 128 may include an annuloplasty ring designed to repair the aortic valve of a subject 120. An "annuloplasty ring" as described in this disclosure refers to a device configured to reinforce, reshape, or stabilize a native annulus of the aortic valve. The annuloplasty ring may be implanted through a delivery system 106 and may be used in aortic valve repair procedures, such as any procedures as described in this disclosure. In one or more embodiments, the annuloplasty ring may be complete (i.e., encircling the entire annulus) or partial (i.e., supporting only a segment of the annulus), and may be flexible, semi-rigid, or rigid, depending on the specific pathology being treated. In one or more embodiments, the annuloplasty ring may be sized and shaped to conform to the native aortic annulus and may be configured to restore the anatomical geometry and functional competency of the aortic valve. An "aortic annulus" as described herein is a structure that forms the base of the aortic valve. In one or more embodiments, the aortic annulus may include a ring-like structure that anchors valve leaflets to the left ventricular outflow tract. In one or more embodiments, the aortic annulus may further maintain the shape and structural integrity of the valve opening of the aortic valve. In one or more embodiments, the annuloplasty ring may be flexible, semi-rigid, or rigid depending on the desired clinical outcome, and may be delivered to the aortic annulus through the delivery system in a collapsed or compressed configuration. Upon reaching the target location, the annuloplasty ring may be expanded and anchored to the aortic annulus using one or more anchoring mechanisms such as barbs, hooks, or tissue-penetrating fasteners. In one or more embodiments, the annuloplasty ring may include radiopaque markers and/or be echogenic to enhance visibility under fluoroscopic or ultrasound imaging. This allows the ultrasound imaging device to confirm placement and deployment of the annuloplasty ring in real time. In one or more embodiments, the delivery system may include steering and/or positioning controls that allow an operator, such as a medical professional, to align the annuloplasty ring with the aortic annulus with precision. In one or more embodiments, the annuloplasty ring may be self-expanding, utilizing shape-memory materials such as nitinol. In one or more embodiments, the annuloplasty ring may be balloon expandable. The delivery and deployment process may be visualized using real-time TEE imaging data, with the ultrasound imaging device positioned within the esophagus to capture cross-sectional views of the aortic valve apparatus and surrounding left-sided cardiac structures. In one or more embodiments, annuloplasty rings may include, but are not limited to, flexible rings, semi-rigid rings, rigid rings, complete rings, partial rings, self-expanding annuloplasty rings, and/or the like.

With continued reference to FIG. 1, in one or more embodiments, prosthetic device 128 may include a mechanical valve configured to replace a native aortic valve. A "mechanical valve" as described in this disclosure refers to a prosthetic heart valve configured to replace a native aortic valve. In one or more embodiments, the mechanical valve may be made of durable, biocompatible materials and designed to regulate unidirectional blood flow across the left ventricular outflow tract. In one or more embodiments, the mechanical valve may include a frame and/or housing and one or more occluding components (e.g., leaflets or discs) that open and close in response to pressure gradients during the cardiac cycle. In one or more embodiments, the mechanical valve is delivered by the delivery system and deployed at an aortic annular position to restore valvular function. In one or more embodiments, the mechanical valve may be constructed from biocompatible metals such as titanium or cobalt-chromium alloys and may include occluded leaflets or discs that pivot or rotate to regulate unidirectional blood flow. In one or more embodiments, the mechanical valve may be delivered in a crimped or collapsed configuration and expanded at the target site using mechanical, balloon, or self-expanding mechanisms. In one or more embodiments, the mechanical valve may be delivered through the delivery system via transfemoral or transapical arterial access routes and deployed in the region of the native aortic valve annulus after adequate imaging-based alignment and confirmation. In one or more embodiments, delivery system may include control elements that allow the mechanical valve to be oriented and seated properly. In one or more embodiments, delivery system may include markers, sensors, or alignment aids to assist in this positioning.

With continued reference to FIG. 1, in one or more embodiments, real-time imaging captured from ultrasound imaging device may be used to guide valve positioning and confirm seating of the prosthetic device 128. In one or more embodiments, ultrasound imaging device may also facilitate the detection of complications such as interference with surrounding cardiac structures (e.g., anterior mitral leaflet or coronary ostia), confirm adequate leaflet motion, and ensure device stability post-deployment.

With continued reference to FIG. 1, in one or more embodiments, delivery system 106 may be introduced into a subject via a percutaneous arterial access site, such as the femoral artery. The delivery system may be navigated through the femoral artery and advanced through the descending aorta, aortic arch, and into the ascending aorta to reach the aortic valve. This arterial route may provide direct access to the aortic valve for repair or replacement. In one or more embodiments, the delivery system 106 may be navigated using a set of images as described in further detail below to ensure precise alignment and positioning relative to the aortic valve annulus. In one or more embodiments, delivery system 106 may include a steerable catheter shaft that enables controlled articulation within the arterial system and the cardiac chambers. The steerable mechanism may allow the distal portion of the catheter to be oriented toward the aortic valve, facilitating coaxial alignment of the prosthetic device 128 with the native valve annulus. In one or more embodiments, positioning of the delivery system may be confirmed using real-time TEE imaging, which provides dynamic visualization of the left ventricular outflow tract, aortic valve, and surrounding cardiac structures. In one or more embodiments, the distal end of the delivery catheter may include an integrated deployment mechanism, such as a sheath retraction system, balloon expansion system, or self-expanding frame release, depending on the type of prosthetic device being delivered. In one or more embodiments, once the distal end of delivery system 106 is positioned at the target location near the aortic valve, the prosthetic device 128 may be advanced and deployed. Deployment may occur in a stepwise fashion, beginning with partial expansion or anchoring, followed by full release after confirmation of appropriate alignment and seating. In one or more embodiments, anchoring mechanisms such as radial force, barbs, anchors, or leaflet clasping elements may be used to secure the prosthetic device 128 within the aortic annulus. Throughout the deployment process, TEE imaging may be used to monitor device orientation, confirm annular engagement, and verify functionality of the prosthetic valve or repair device in real time. In one or more embodiments, after the prosthetic device 128 is deployed, the delivery system 106 may be withdrawn through the femoral artery. Hemostasis at the access site may be achieved using vascular closure devices or manual compression, in accordance with standard interventional cardiology techniques. Post-deployment imaging with TEE and/or fluoroscopy may be performed to confirm proper device function, assess for residual stenosis or regurgitation, and exclude complications such as device embolization or interference with adjacent cardiac structures.

With continued reference to FIG. 1, delivery system 106 is within a field of view of ultrasound imaging device. A “field of view” as described in reference to ultrasound imaging device refers to an anatomical region that is imaged and visualized by the ultrasound imaging device. In one or more embodiments, the field of view may encompass a range of cardiac structures, including but not limited to, the ascending aorta, aortic valve annulus, aortic valve leaflets, left ventricular outflow tract, and/or the like. In one or more embodiments, the catheter and prosthetic device 128 may be visualized in real time as the delivery system is advanced through the arterial vasculature, including the femoral artery and aorta, and positioned at or near the aortic valve. In one or more embodiments, delivery system 106 may be within the field of view of the ultrasound imaging device such that the delivery system may be captured within at least one image of a set of images. In one or more embodiments, delivery system 106 may be within the field of view such that ultrasound imaging device is capable of capturing and visualizing the delivery system during one or more phases of an aortic valve-related procedure as described herein. In one or more embodiments, the field of view may be adjusted by repositioning or steering the ultrasound imaging device to optimize visualization of the delivery system 106 and target anatomy. In one or more embodiments, ultrasound imaging device may detect acoustic signatures, such as echogenic reflections or acoustic shadows, corresponding to a catheter shaft, distal tip, or prosthetic components of delivery system 106, thereby allowing an operator to confirm device identity, orientation, and placement of delivery system 106. In one or more embodiments, delivery system 106 may be within the field of view for only a portion of the procedure. For example and without limitation, once the delivery system enters the ascending aorta or approaches the aortic annulus, delivery system may no longer be within the field of view. In one or more embodiments, ultrasound imaging device may be used to dynamically track a position of delivery system 106 by acquiring and analyzing real-time images that include anatomical landmarks and device components, as described in further detail below.

Apparatus 100 includes at least a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail through a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a “shared nothing” architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus includes a memory 108 communicatively connected to at least a processor 104, wherein the memory 108 contains instructions configuring at least a processor 104 to perform any processing steps described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, through a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 is configured to receive a set of images 112 of a structure of a subject 120. As used in this disclosure, a "set of images" refers to a group of one or more visual representations. Set of images 112 may include, without limitation, a two-dimensional image. In one or more embodiments, set of images 112 may include an ultrasonic image. As used herein, an "ultrasonic image" is an image generated as a function of a reflection of a sound wave off of a structure. In one or more embodiments, the ultrasonic image is a transesophageal echocardiogram (TEE) image. As used herein, a "structure" is a component of a subject's heart. Non-limiting examples of structures include organs and tissues. In one or more embodiments, structure includes an organ of a subject. In non-limiting examples, a structure may include a heart, lung, spleen, liver, kidney, muscle, skeleton, intestine, stomach, vein, and/or artery. In additional non-limiting examples, structure may include the left ventricle, ascending aorta, and/or aortic valve 116. In one or more embodiments, structure includes an aortic valve pertaining to subject 120. In one or more embodiments, structure may include portions of the heart and/or cardiac anatomy that are close in proximity to the aortic valve. In one or more embodiments, set of images 112 may include images captured at or near the aortic valve 116, wherein structure may include the surrounding walls or tissue around the TEE probe 102. In one or more embodiments, structure may include any surrounding walls or tissue captured by the transducer. In one or more embodiments, structure may include a portion of a heart, a single chamber of the heart, and/or the like. In one or more embodiments, structure may include the left ventricular outflow tract or ascending aorta, wherein the TEE probe 102 may capture sets of images in proximity to the aortic valve 116. In one or more embodiments, structure may include chambers (e.g., four chambers including left and right atria and left and right ventricles), valves (i.e., the structures that regulate blood flow between chambers and vessels, including the aortic, mitral, tricuspid, and pulmonary valves), vessels (e.g., aorta, pulmonary arteries and veins, and coronary arteries), conduction system (i.e., a network of specialized cells that control the heart's electrical activity and rhythm), muscular and connective tissues (e.g., heart's muscular walls, septa, any other connective tissues that provide structural integrity and enable contraction), and/or other components of a heart. In one or more embodiments, structure may include the aortic valve 116 and/or any other portions of the heart that may be of interest during an aortic-valve-related procedure.

Still referring to FIG. 1, as used in this disclosure, a "subject" refers to an individual organism that is the focus of an aortic valve related procedure. In one or more embodiments, subject 120 may include a human, such as a human undergoing a medical procedure including aortic valve repair, aortic valve replacement, left heart catheterization, and/or any other cardiac procedures involving the left heart or aortic outflow tract. In one or more embodiments, subject 120 may include a provider of set of images 112 and/or an individual associated with set of images 112 as described herein. In one or more embodiments, subject 120 may include a recipient or a participant in a clinical trial or research study. In a non-limiting example, subject 120 may include a human patient with aortic stenosis or regurgitation undergoing a transcatheter valve intervention, an individual undergoing cardiac screening, a participant in a clinical trial, patient with congenital heart disease, heart transplant candidate, patient receiving follow-up care after cardiac surgery, healthy volunteer, patient with heart failure, or the like. Additionally, or alternatively, subject 120 may include an animal model used to study cardiac function, such as a laboratory animal used in aortic valve procedure research.

Still referring to FIG. 1, in an embodiment, each ultrasonic image of set of ultrasonic images (or each image of set of images) may include a particular view of subject's 120 heart's chambers, valves, vessels, and/or the like. In a non-limiting example, set of images 112 may include multiple views such as different angles and perspectives of subject's 120 heart obtained using a TEE probe 102. In another embodiment, set of images 112 may be arranged in a temporal sequence. In a non-limiting example, set of images 112 may include a series of images captured over time, allowing for observation of dynamic cardiac functions such as valve leaflet motion, blood flow across the aortic valve 116, and/or cardiac cycle progression. In one or more embodiments, each ultrasonic image of set of images 112 may include a corresponding timestamp, wherein the timestamp may include an indicator showing a date and time of when the corresponding ultrasonic image was acquired.

Additionally, or alternatively, and still referring to FIG. 1, various imaging techniques or settings may be applied to set of images 112 that provide specific insights into structure. In one or more embodiments, structure may include a plurality of physical characteristics, spatial relationships, and functional aspects of the heart's components. For instance, and without limitation, receiving set of images 112 may include applying a Doppler imaging technique. A "Doppler imaging technique" as described in this disclosure is a specialized ultrasound method used to assess the movement of blood, particularly within the heart and great vessels. Processor 104 may configure a TEE probe 102 to emit high-frequency sound waves into the subject's 120 body, wherein the sound waves may reflect off moving blood cells and cardiac structures. The reflected waves may be received by the transducer, and changes in frequency (Doppler shift) based on the velocity and direction of flow may be analyzed to determine one or more hemodynamic parameters. In one or more embodiments, one or more ultrasonic images within set of images 112 may include visual representations of blood flow characteristics, optionally color-coded to indicate speed and direction of flow through the aortic valve 116 or left heart chambers.

With continued reference to FIG. 1, in one or more embodiments, receiving set of images 112 of structure may include receiving a patient profile pertaining to subject 120. As used in this disclosure, a "patient profile" is a comprehensive collection of information related to an individual patient. In one or more embodiments, patient profile may include a variety of different types of data that, when combined, provide a detailed picture of a patient's overall health. In an embodiment, patient profile may include demographic data of patient, for example, and without limitation, patient profile may include basic information about the patient such as name, age, gender, ethnicity, socioeconomic status, and/or the like. In another embodiment, each patient profile may also include a patient's medical history, for example, and without limitation, patient profile may include a detailed record of the patient's past health conditions, medical procedures, hospitalizations, and illnesses such as surgeries, treatments, medications, and/or the like. In another embodiment, each patient profile may include lifestyle Information of patient, for example, and without limitation, patient profile may include details about the patient's diet, exercise habits, smoking and alcohol consumption, and other behaviors that could impact health. In a further embodiment, patient profile may include patient's family history, for example, and without limitation, patient profile may include a record of hereditary diseases. As an ordinary person skilled in the art, upon reviewing the entirety of this disclosure, will be aware of various type of data within patient profiles. Apparatus 100 may receive and process in consistent with this disclosure.

In a non-limiting example, and still referring to FIG. 1, patient profile may include one or more ultrasonic images or set of images 112. Receiving set of images 112 may include extracting the set of images 112 from patient profile (subsequent to patient identity verification and obtaining consent from subject 120). In one or more embodiments, patient profile of subject 120 may be obtained through hospital information system (HIS) or any other data acquisition platform to securely access patient's electronic medical record (EMR) or other relevant databases. Set of images 112 may be directly or indirectly downloaded or exported. In one or more embodiments, each ultrasonic image of set of images 112 may be in a usable and/or computer-readable format such as, without limitation, DICOM format, and necessary metadata (e.g., patient information described above) may be included. Further, receiving set of images 112 may include recording the access and extraction of set of images 112; for instance, and without limitation, this process may be documented, by processor 104, in the patient's/subject's 120 medical record, databases, or other appropriate logs.

Further, and still referring to FIG. 1, in other embodiments, patient profile may include electrocardiogram (ECG) data, wherein the "ECG data," for the purpose of this disclosure, refers to data related to an electrocardiogram of the patient that corresponds to the patient profile. An "electrocardiogram," as used herein, is a medical test that records the electrical activity of subject's heart over a period of time. In an embodiment, ECG data may include one or more recordings captured by a plurality of electrodes placed on patient's skin. In one or more embodiments, ECG data may include information regarding a P wave, T wave, QRS complex, PR interval, ST segment, and/or the like. Processor 104 may associate set of images 112 with ECG data, or in other cases, receiving set of images 112 may include receiving ECG data pertaining to subject 120 associated with set of images 112. Such ECG data may be collected simultaneously during ultrasonic imaging. In one or more embodiments, set of images 112 may be linked with ECG data by one or more unique identifiers, such as without limitations, timestamps or other metadata described herein. In a non-limiting example, ECG data may be used to identify specific cardiac events or phases of the cardiac cycle, and the corresponding ultrasonic images may be analyzed to see how heart's structure changes during those times.

With continued reference to FIG. 1, in other embodiments, receiving set of images 112 may include receiving set of ultrasonic images from Data store 124. In one or more embodiments, Data store 124 may be implemented, without limitation, as a relational database, a key-value retrieval database such as a NOSQL database, or any other format or structure for use as a database that a person skilled in the art would recognize as suitable upon review of the entirety of this disclosure. Data store 124 may alternatively or additionally be implemented using a distributed data storage protocol and/or data structure, such as a distributed hash table or the like. Data store 124 may include a plurality of data entries and/or records as described above. Data entries in Data store 124 database may be flagged with or linked to one or more additional elements of information, which may be reflected in data entry cells and/or in linked tables such as tables related by one or more indices in Data store 124 or another relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

In a further embodiment, and still referring to FIG. 1, receiving set of images 112 may involve one or more image preprocessing steps. In one or more embodiments, processor 104 may be configured to calibrate one or more ultrasonic images of set of images 112 by correcting for distortions and ensuring accurate spatial representation of structure pertaining to subject 120. In a non-limiting example, processor 104 may select one or more reference objects within ultrasonic image that needs calibration to correct spatial distortions. In one or more embodiments, processor 104 may be configured to place a phantom with pre-determine dimensions in such ultrasonic image and adjust ultrasonic image until the phantom's dimensions are accurately represented. In another non-limiting example, one or more ultrasonic images' brightness and contrast may be adjusted, by processor 104 to ensure that echogenicity (reflectivity) of the tissues is accurately represented. One or more tissues with known echogenicity may be selected by processor 104 as reference tissues to adjust corresponding portions of the one or more ultrasonic images. In other cases, standardized correction curves may be applied in order to correct the echogenicity of ultrasonic images. As an ordinary person skilled in the art, upon reviewing the entirety of this disclosure, may be aware of various calibration techniques, such as, without limitation, temporal calibration, geometric calibration, among others that can be used by processor 104 to preprocess set of images 112.

Additionally, or alternatively, and still referring to FIG. 1, receiving set of images 112 may include perform image segmentation on or more ultrasonic images of set of images 112. In one or more embodiments, image segmentation may include separating specific structures or regions of interest (ROI) from the background or other structures in a given ultrasonic image. In a non-limiting example, processor 104 may be configured to use edge detection algorithms to outline the heart chambers, separating them from surrounding tissues. One or more filters may be applied to highlight the boundaries between different types of tissues during the segmentation. In another non-limiting examples, valves and vessels may also be segmented by applying thresholding techniques. Processor 104 may be configured to set an intensity threshold based on the known echogenicity of blood and vessel walls and select pixels or regions having intensity below or above the intensity threshold from the given ultrasonic image. In one or more embodiments, one or more machine learning models may be used to perform image segmentations, for example, and without limitation, a U-net (i.e., a convolution neural network containing a contracting path as an encoder and an expansive path as a decoder, wherein the encoder and the decoder forms a U-shaped structure).

With continued reference to FIG. 1, as used in this disclosure, a "segmentation model" is an artificial intelligence or algorithm-based model designed to process images data, such as sets of images and identify anatomical structures of interest by segmenting or delineating specific regions within the acquired imaging frames. In an embodiment, the segmentation model may include a segmentation algorithm. As used in this disclosure, a "segmentation algorithm" is a computational method designed to partition image data (e.g., sets of images) into distinct regions or categories based on predefined criteria. As used in this disclosure, a "segmented image" is an output image produced by the segmentation model. In an embodiment, the segmented image may include specific anatomical structures or regions that have been highlighted or delineated to facilitate analysis, interpretation, and probe navigation. As used in this disclosure, a "comparison" is an analytical process in which a newly segmented image is evaluated against previously segmented images from adjacent probe positions. In an embodiment, the comparison may be performed to determine positional differences, identify structural variations, refine probe guidance, and the like. As used in this disclosure, an "adjacent probe position" is a previously recorded spatial position of the Probe (wherein probe may be consistent with a TEE probe 102) that is proximal to the current or predicted probe position. In an embodiment, the adjacent probe position may be used as a reference for comparative analysis in guiding probe navigation. For example, without limitation, in an embodiment, the apparatus 100 may utilize the probe position predictor to estimate the predicted position of the TEE probe 102 based on prior movement data. Continuing, as the probe is advanced, the apparatus 100 may capture a new frame of sets of images from the at least a transducer and process it using the segmentation model to generate the segmented image highlighting cardiac structures. Without limitation, the comparison may then be performed between the segmented image of the new frame and segmentations obtained from adjacent probe positions within the at least a 3D model, allowing the apparatus 100 to refine its estimate of the probe's position. Without limitation, this approach may enhance probe navigation, improve visualization of anatomical structures, and ultimately reduce errors in interventional procedures.

With continued reference to FIG. 1, segmenting each image of a set of images may include applying a segmentation algorithm, wherein the segmentation algorithm includes detecting at least a feature of the structure and removing artifacts from each frame of the set of images of each sweep. The segmentation algorithm may be used to identify and delineate specific structures within medical imaging data, such as organs, tissues, or pathological regions, enabling more precise analysis and visualization. The segmentation algorithm may leverage techniques such as thresholding, edge detection, clustering, or machine-learning-based approaches to enhance accuracy and adapt to variations in image quality and anatomical differences. As used in this disclosure, a "feature" is a structural or textural characteristic within an image that is identifiable. In an embodiment, the at least a feature may be used for analysis, such as anatomical boundaries, edges, shapes, or specific tissue properties, and the like. In an embodiment, the at least a feature may include elements like the endocardial border of the heart, valve leaflets, or the left ventricular outflow tract, the aortic valve 116 and/or the like, which are essential for accurate interpretation and procedural navigation.

With continued reference to FIG. 1, as used in this disclosure, "artifacts" are noise present in an image. In an embodiment, the artifacts may include distortions, unintended elements, and the like. In an embodiment, the artifacts may obscure relevant anatomical structures and interfere with accurate segmentation or analysis. Without limitation, the artifacts may arise due to factors such as motion, shadowing, reverberation, or signal dropout and can lead to misinterpretation of the imaging data if not properly accounted for. In an embodiment, segmenting each image of the set of images during a sweep of catheter and/or transducer may involve applying a segmentation algorithm designed to isolate and enhance key features of the imaged structure while minimizing the impact of artifacts. For instance, without limitation, the segmentation algorithm may detect the boundary of a heart valve, differentiating it from surrounding tissues and fluid-filled regions, ensuring clearer visualization of the structure. Continuing, without limitation, by accurately extracting relevant features, the apparatus may improve the precision of anatomical analysis and interventional guidance. Additionally, and/or alternatively, the segmentation algorithm may incorporate artifact removal techniques to enhance image clarity. Motion-related artifacts, which can occur due to probe movement or cardiac motion, may be mitigated by using temporal filtering methods. Shadowing artifacts, which can obscure portions of the image, may be addressed by leveraging adaptive intensity correction or deep-learning-based artifact suppression. Without limitation, through these processes, the segmentation algorithm may refine the imaging data, allowing for improved reliability in automated probe navigation and procedural decision-making. Continuing, without limitation, by effectively detecting key features and minimizing artifacts, the segmentation process may contribute to enhanced accuracy in ultrasound imaging. This may facilitate more reliable interpretation of anatomical structures, support real-time adjustments in probe positioning, and ultimately reduce errors in interventional procedures such as valve implantation or atrial appendage closure. The improved imaging clarity may lead to better procedural outcomes by providing clinicians with a clearer and more comprehensive view of the target structures.

Still referring to FIG. 1, apparatus 100 may include a 3D reconstruction model 138. In one or more embodiments, the 3D reconstruction model 138 may be configured to generate at least a 3D model 156 representative of at least an aortic valve 116 as a function of the set of images. In one or more embodiments, generating the 3D model includes segmenting each image of a set of images within the set of images and generating the 3D model 156 as a function of those images. As used in this disclosure, a "3D reconstruction model" is a model configured to generate a three-dimensional (3D) representation of a structure as acquired from a set of images. In one or more embodiments, 3D model may include a three-dimensional representation of structure such as the aortic valve 116 and/or surrounding anatomical features of the cardiac anatomy near the aortic valve 116. The 3D reconstruction model 138 may process a sequence of ultrasound frames, extract spatial and depth information, and reconstruct the structure in a volumetric format for enhanced visualization and analysis. The model may utilize image segmentation, interpolation, machine learning algorithms, and the like, to refine the 3D representation, enabling improved diagnostic accuracy and procedural guidance.

With continued reference to FIG. 1, in one or more embodiments, processor and/or 3D reconstruction model 138 may receive a sequence of ultrasound frames and/or a set of images obtained during a sweep of the ultrasound imaging device within the heart. The 3D reconstruction model 138 may process the set of images to extract spatial, depth, and structural information, aligning and integrating the frames to create a volumetric representation of the heart and/or aortic valve 116. The reconstruction process may involve several computational steps, including image segmentation, where relevant cardiac structures such as the ventricles, atria, valves (including the aortic valve 116), and major blood vessels are identified and isolated from the surrounding tissue. The 3D reconstruction model 138 may then perform interpolation and surface rendering, generating a smooth and continuous representation of the heart by filling in gaps between imaging planes and reconstructing anatomical contours with high precision. Additionally, and/or alternatively, advanced processing techniques such as motion correction and artifact reduction may be applied to enhance the clarity and accuracy of the 3D model. Without limitation, the generated 3D model may provide a comprehensive visualization of the anatomy of the heart, allowing clinicians to assess structural integrity, detect abnormalities such as aortic valve 116 stenosis or regurgitation, plan interventional procedures with greater accuracy, and the like. In one or more embodiments, the 3D reconstruction model 138 may enable real-time updates, dynamically adjusting the 3D model as new sets of images are received, providing continuous visualization during diagnostic evaluations or surgical navigation. The 3D reconstruction model 138 may be displayed on a user interface, manipulated for different viewing angles, or integrated with additional imaging modalities for enhanced diagnostic insight, as described in more detail below.

With continued reference to FIG. 1, processor 104 and/or 3D reconstruction model 138 may be configured to generate a 3D data structure that represents structure and/or the aortic valve as a function of set of images 112. In one or more embodiments, the set of shape parameters may include a 3D data structure representative of the structure and/or aortic valve 116. In a non-limiting example, the 3D data structure may include a 3D voxel occupancy representation (VOR). As used in this disclosure, a "3D voxel occupancy representation (VOR)" of anatomy is a 3D digital representation of a spatial structure of the anatomy, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such as density/occupancy as described below. In an embodiment, each voxel of the plurality of voxels within the 3D VOR may represent a specific portion of structure. In one or more embodiments, a voxel may be the smallest distinguishable box-shaped part (i.e., 1px·1px·1px) of a three-dimensional image. In one or more embodiments, each voxel of the plurality of voxels within the VOR may be represented as a cube or rectangular prism (although other shapes may be used in specialized applications). Each voxel may include a size that determines a resolution of the 3D image or model. In an embodiment, smaller voxels may provide higher resolution; however, it may require more computational resources (e.g., RAM) for processor 104 to process.

In an embodiment, and still referring to FIG. 1, each voxel of plurality of voxels within VOR may include one or more embedded values. As used herein, "embedded values" refers to specific numerical or categorical data associated with each voxel. In one or more embodiments, embedded values may represent various attributes or characteristics of the corresponding portion of structure that voxel represents. In a non-limiting example, embedded values may include density values, intensity values, texture information, or any other quantitative measures that provide insights into the underlying tissue. Such embedded values may be derived from set of ultrasonic images or other imaging modalities used to generate data structure. In one or more embodiments, embedded values may be utilized, by processor 104, to differentiate between different types of tissues, such as myocardial tissue, blood vessels, or chambers. Embedded values may also facilitate the visualization of dynamic cardiac functions, for example, and without limitation, blood flow or heart beating by encoding temporal information such as timestamps within plurality of voxels.

Still referring to FIG. 1, in an embodiment, each voxel of plurality of voxels may include a presence indicator. As used in this disclosure, a "presence indicator" refers to a data element that indicates a presence or absence (i.e., occupancy) of tissue within that portion. In one or more embodiments, and without limitation, presence indicator may include an occupancy status as one of the embedded values described herein. Portion may include a specific location within 3D space where data structure is generated; for instance, and without limitation, a coordinate in 3D space represented in a tuple such as (x, y, z). In an embodiment, 3D VOR may provide a spatial framework that allows for the modeling and visualization of structure in 3D space. In one or more embodiments, 3D data structure may include a plurality of layers or slices (either horizontal [e.g., xy plane] or vertical [e.g., xz or yz plane depends on the view direction]), wherein each layer or slices of the plurality of layers or slices is corresponding to a different cross-sectional view of a structure of subject 120, and collectively forming a comprehensive 3D depiction of the structure. In a non-limiting example, 3D VOR having plurality of voxels with presence indicators may indicate whether each voxel in 3D space may be occupied by a part of a structure of subject 120. A binary value such as 0 or 1 may be configured as presence indicator to show ether a pixel of 3D space is occupied (e.g., 1) or empty (e.g., 0). In should be noted that other values may be used as presence indicator such as a Boolean value e.g., TRUE or FALSE.

In one or more embodiments, and still reference to FIG. 1, one or more embedded values, such as, without limitations, occupancy, or density, may be derived from set of images 112 described herein by processor 104. In a non-limiting example, determining occupancy status of each voxel of plurality of voxels may include converting set of ultrasonic images to a set of binary images and determining occupancy status of each voxel as a function of the structure of interest's binary value. In one or more embodiments, occupancy status may include a value representing the likelihood of occupancy of the corresponding tissue. In another non-limiting example, density may be calculated, by processor 104, for each voxel as a function of the echogenicity of one or more pixels on a given ultrasonic image, wherein, the brightness of the given ultrasonic image may be analyzed since different tissues reflect ultrasound waves differently.

With continued reference to FIG. 1, generating 3D data structure of structure may include generating a 3D array. In one or more embodiments, processor 104 may divide 3D space into a grid of plurality of voxels, each with specific x, y, and z coordinates as embedded values. Each element of 3D array may correspond to a voxel. In one or more embodiments, 3D array may allow for easy access and manipulation of plurality of voxels, enabling various analyses, visualizations, and transformations either described or not described herein. In a non-limiting example, embedded values may include a density of the tissue at a specific location of a patient's body derived from one or more ultrasonic images of set of images 112.

Additionally, or alternatively, and still referring to FIG. 1, 3D data structure of structure may include a 3D grid configured to map presence indicators and/or other embedded values described herein of plurality of voxels (e.g., tissue density, blood flow velocity, echogenicity or acoustic properties, and any other biophysical properties). As used in this disclosure, a "3D grid" refers to a 3D data structure that divides a given volume (e.g., volume of a structure) into a plurality of discrete units called cells (i.e., volume elements). In an embodiment, each cell within 3D grid may be associated with a distinct voxel. Mapping presence indicators or other embedded values may include assigning each presence indicator or embedded value to each point within 3D grid such as corners of each corresponding cell. Such values May be derived from set of images 112 as described above.

In yet another embodiment, and still referring to FIG. 1, cells may be continuous, meaning that one or more cells may represent one or more continuous regions of space rather than discreate, separate units. In a non-limiting example, instead of being uniform, mapped presence indicator and/or other embedded values may vary continuously across different cells or cell's volume. In such embodiment, processor 104 may use interpolation to estimate other (unknown) embedded values within a range based on existing values such as known embedded values at specific points, thereby allowing for smooth transitions between cells. Exemplary interpolation methods may include, without limitation, linear interpolation, cubic interpolation, and/or the like. For example, and without limitation, if the corners of a cell have known values interpolation can be used to estimate the values at any point within the cell based on those corner values.

In a non-limiting example, and still referring to FIG. 1, 3D data structure of structure may include a 3D grid having a plurality of cells e.g., voxels, wherein each cell may contain a continuous range of values representing tissue density, blood flow velocity, or other properties (i.e., embedded values). Processor 104 may be configured to apply trilinear or tricubic interpolation to estimate tissue density within each cell based on presence indicator or other known values at the cell's boundaries, since tissue densities change gradually; Such 3D grid may provide a smooth, continuous representation of heat's internal structures, allowing for more nuanced analysis and visualization as described below. In a further embodiment, 3D grid with continuous cells may be additionally used in fluid dynamics simulations.

With continued reference to FIG. 1, in some case, presence indicators and/or other embedded values may be mapped to 3D grid as a function of array masking, wherein specific array or grid may be selected to modify based on one or more pre-defined criteria. In a non-limiting example, processor 104 may generate a mask e.g., a binary array that defines which voxels or cells are affected. Mask may be used to select or modify specific voxels or cells based on certain attributes; for instance, and without limitation, processor 104 may use mask to isolate the LA within the heart focusing the analysis on that specific region. Such mask may include criteria defined by specific density thresholds that distinguish the LA's tissue (i.e., voxels representing LA in 3D grid) from surrounding structures (i.e., neighboring voxels). In one or more embodiments, such mask may further include a binary mask, wherein each voxel in the 3D grid may be assigned a first presence indicator such as 1 if the voxel meets the criteria for the LA and a second presence indicator such as 0 if it does not. In one or more embodiments, mask may be directly applied to 3D grid, selecting, or modifying voxels or cells, thereby enabling processor 104 to highlight, exclude, or otherwise manipulate specific parts of structure within 3D grid. Processor 104 may then perform an element-wise multiplication between 3D grid and the mask. Continuing from the previous non-limiting example, voxels corresponding to the LA (wherein the mask value is 1) may retain their original values, while other voxels (where the mask value is 0) may be set to 0 or other specific value (i.e., excluded or masked out).

With continued reference to FIG. 1, in one or more embodiments, 3D grid may include one or more spatial features extracted from set of images 112 of structure. As used in this disclosure, "spatial features" are specific characteristics or attributes related to the spatial arrangement, shape, size, texture, or orientation of structures within a 3D space. In one or more embodiments, spatial features may include one or more embedded values described herein and their combinations thereof. In a non-limiting example, spatial feature may be represented numerically as a vector, a metric or other mathematical constructs that capture specific spatial characteristics. In one or more embodiments, spatial features may also be visualized as contours, surfaces, or other geometric representations. In an embodiment, spatial features may be extracted using edge detection, texture analysis, or other image processing techniques (e.g., cleaning and enhancing images, image segmentation, and/or the like). In another embodiment, one or more machine learning models, such as convolutional neural networks (CNNs) as described in further detail below, may be used to extract complex spatial features.

Still referring to FIG. 1, as used in this disclosure, a "vector" is a data structure that represents one or more a quantitative values and/or measures of one or more spatial features. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes.

Still referring to FIG. 1, in a non-limiting example, one or more spatial features may include one or more shape features (i.e., characteristics related to the shape of specific structures), such as curvature, surface area, volume, and/or the like. In another non-limiting example, one or more spatial features may include one or more texture features (i.e., characteristics related to the texture or pattern within tissues, as seen in set of images 112), such as gray-level co-occurrence matrix (GLCM) features representing the texture of heart muscle tissue. In another non-limiting example, one or more spatial features may include one or more orientation features (i.e., characteristics related to the orientation or alignment of structures), such as the angle or alignment of the septum within the heart. In a further non-limiting example, one or more spatial features may include one or more edge and boundary features (i.e., Characteristics related to the edges or boundaries between different structures), such as edge detection features highlighting the boundary between the myocardium and the cardiac chambers. As an ordinary person skilled in the art, upon reviewing the entirety of this disclosure, will be aware of various spatial features extracted from set of images 112 in consistent with this disclosure.

With continued reference to FIG. 1, in one or more embodiments, apparatus 100 and/or 3D reconstruction model 138 may include a computer vision model configured to generate 3D data structure of structure by implementing image segmentation methods as described further below. A "computer vision model," for the purpose of this disclosure, is a computation model designed to interpret and make determinations based on visual data. In an embodiment, computer vision model may process set of images 112, to make a determination about a scene, space, and/or object in structure. In a non-limiting example, computer vision model may be used for registration of plurality of voxels within a 3D space. In one or more embodiments, registration may include image processing described herein, such as without limitation object recognition, feature detection, edge/corner detection, and the like. Non-limiting example of feature detection may include scale invariant feature transform (SIFT), Canny edge detection, Shi Tomasi corner detection, and the like. In one or more embodiments, registration may include one or more transformations to orient an ultrasonic image relative to a 3D coordinate system; exemplary transformations include without limitation homography transforms and affine transforms. In an embodiment, registration of ultrasonic image to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto the ultrasonic image; however, a third dimension of registration, representing depth and/or a z axis, may be detected by utilizing depth-sensing techniques such as Doppler imaging. Alternatively, the third dimension may be inferred from the known geometry and orientation of the imaging device (e.g., TEE catheter), or through the application of one or more machine learning models trained to interpret depth from the two-dimensional projection.

With continued reference to FIG. 1, processor 104 and/or 3D reconstruction model 138 may use and/or a include a machine learning module to implement one or more algorithms or generate one or more machine learning models, such as a structure modeling model to generate data structure of structure, such as aortic valve 116. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from a database, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In a further embodiment, training data may include previous outputs such that one or more machine learning models iteratively produces outputs.

Still referring to FIG. 1, machine learning module may be used to generate structure modeling model and/or any other machine learning models, such as shape identification model as described in further detail below, using training data. Structure modeling model may be trained by correlated inputs and outputs of training data. Training data may be data sets that have already been converted from raw data whether manually, by machine, or any other method. In an embodiment, generating data structure of structure includes receiving structure training data, wherein the structure training data may include a plurality of image sets as input and a plurality of computed tomography (CT) based 3D models as output, and wherein each image set of plurality of image sets may include any images described in this disclosure. In one or more embodiments, structure training data may be received from Data store 124 or other databases. In other cases, structure training data may be collected by a data acquisition unit from external sources such as one or more medical equipment's e.g., imaging devices or diagnostic tools, wherein the data acquisition may be configured as an intermediary between the data source and machine learning module.

Still referring to FIG. 1, in one or more embodiments, a training dataset may be identified by correlating an instance of computed tomography scan data with a historical ultrasonic image as a function of a medical record and a language model. For example, a language model may be used to interpret a medical record and/or determine whether an instance of computed tomography scan data should be associated with a historical ultrasonic image in a training dataset. For example, a language model may be used to interpret language of a medical record, and the output of the language model may be used to identify whether a medical event has taken place between when the historical ultrasonic image was taken and when the historical computed tomography scan data was recorded, such that they are not to be associated in a training dataset. In another example, a language model may be used to interpret language of a medical record, and the output of the language model may be used to identify whether historical ultrasonic image and historical computed tomography scan data were recorded in a sufficiently short time, such that they are associated in a training dataset. In one or more embodiments, a training dataset may be identified by generating a synthetic ultrasonic image as a function of an instance of computed tomography scan data.

Still referring to FIG. 1, as used in this disclosure, a "computed tomography (CT) based 3D model" refers to a 3D representation of a structure that is created using data from CT scans. In one or more embodiments, a computed tomography (CT) based 3D model may include a 3D representation of a structure and surrounding structures that is created using data from CT scans. Computed Tomography is a medical imaging technique that uses X-rays to capture cross-sectional images (slices) of the body. By taking a plurality of slices, a CT scan creates a detailed 3D representation of the internal structure. In an embodiment, CT-based 3D model may include 3D representations of a structure such as the heart including chambers, valves, blood vessels, and surrounding tissues. In one or more embodiments, CT-based 3D model may be interactive; for instance, medical professionals may rotate, zoom, and/or explore CT-based 3D model from various angles. In one or more embodiments, plurality of CT-based 3D models may be generated prior to the training of the structure modeling model. Plurality of CT-based 3D models may be generated using existing techniques in the field as described above such as, without limitation, FAM, cardiac CT merging, among others. In a non-limiting example, plurality of CT-based 3D models may provide ground through or references models against structure modeling model that is being trained. In a non-limiting example, generating data structure of structure further includes training structure modeling model using structure training data described herein. Structure modeling model trained using structure training data may be able to interpret ultrasonic images by learning relationships between ultrasonic images and corresponding CT-based 3D models. Processor 104 is further configured to generate data structure of structure as a function of set of images 112 using trained structure modeling model. In one or more embodiments, data structure e.g., 3D model 156 as described below may be interpreted, visualized, and analyzed by processor 104 in similar manner to CT-based 3D models, wherein both are 3D structures that correspond to ultrasonic images.

With continued reference to FIG. 1, in an embodiment, 3D reconstruction model 138 includes structure modeling model. In an embodiment, structure modeling model includes a deep neural network (DNN). As used in this disclosure, a "deep neural network" is defined as a neural network with two or more hidden layers. Neural network is described in further detail below with reference to FIGS. 4-5. In a non-limiting example, structure modeling model may include a convolutional neural network (CNN). Generating 3D data structure of structure may include training CNN using structure training data and generating 3D data structure as a function of set of images 112 using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In one or more embodiments, CNN may include, without limitation, a deep neural network (DNN) extension. Mathematical (or convolution) operations performed in the convolutional layer may include convolution of two or more functions, where the kernel may be applied to input data e.g., set of images 112 through a sliding window approach. In one or more embodiments, convolution operations may enable processor 104 to detect local/global patterns, edges, textures, and any other spatial features described herein within each ultrasonic image of set of images 112. Spatial features may be passed through one or more activation functions, such as without limitation, Rectified Linear Unit (ReLU), to introduce non-linearities into the processing step of generating 3D data structure of structure. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the spatial dimensions of spatial feature maps by applying downsampling, such as max-pooling or average pooling, to small, non-overlapping regions of one or more spatial features.

Still referring to FIG. 1, CNN may further include one or more fully connected layers configured to combine spatial features extracted by the convolutional and pooling layers as described above. In one or more embodiments, one or more fully connected layers may allow for higher-level pattern recognition. In a non-limiting example, one or more fully connected layers may connect every neuron (i.e., node) in its input to every neuron in its output, functioning as a traditional feedforward neural network layer. In one or more embodiments, one or more fully connected layers may be used at the end of CNN to perform high-level reasoning and produce the final output such as, without limitation, a 3D data structure of structure. Further, each fully connected layer may be followed by one or more dropout layers configured to prevent overfitting, and one or more normalization layers to stabilize the learning process described herein.

With continued reference to FIG. 1, CNN may further include a 3D CNN, wherein the 3D CNN, unlike standard 2D CNN, may include utilization of one or more 3D convolutions which allow them to directly process 3D data, thereby enabling processor 104 to generate 3D structures such as 3D data structure of structure using the 3D CNN. In a non-limiting example, 3D CNN may include one or more 3D filters (i.e., kernels) that move through the set of images 112 in three dimensions and capturing spatial relationships in x, y, and z axis. Similar to 3D convolutions, 3D CNN may further include one or more 3D pooling layers that may be used to reduce the dimensionality of ultrasonic images while preserving spatial features as described above. Additionally, or alternatively, an encoder-decoder structure may be implemented (extended to 3D), by processor 104, in 3D CNN, wherein the encoder-decoder structure includes an encoding path that captures the context and a decoding path that enables precise localization in a same manner as U-net as described above. Such encoder-decoder structures may also include a plurality of skip connections, allowing 3D CNN to use information from multiple resolutions to improve the process of generating 3D data structure of structure.

With continued reference to FIG. 1, in an embodiment, training the structure modeling model (i.e., CNN) may include selecting a suitable loss function to guide the training process. In a non-limiting example, a loss function that measures the difference between the predicted 3D VORs and the ground truth 3D structure e.g., CT-based 3D models may be used, such as, without limitation, mean squared error (MSE) or a custom loss function may be designed for one or more embodiments described herein. Additionally, or alternatively, optimization algorithms, such as stochastic gradient descent (SGD), may then be used to adjust the structure modeling model's parameters to minimize such loss. In a further non-limiting embodiment, instead of directly predicting 3D data structure, structure modeling model may be trained as a regression model to predict presence indicators and/or other embedded values described herein for each voxel of plurality of voxels within a 3D grid. Additionally, CNN may be extended with additional deep learning techniques, such as recurrent neural networks (RNNs) or attention mechanism, to capture additional features and/or data relationships within input data. These extensions may further enhance the accuracy and robustness of the 3D modeling.

With continued reference to FIG. 1, processor 104 and/or 3D reconstruction model 138 is configured to generate a set of shape parameters 136 based on set of images 112. As used in this disclosure, a "set of shape parameters" refers to a collection of numerical values or descriptors that quantitatively represent the geometric or morphological characteristics of a structure. In one or more embodiments, a set of shape parameters may represent a shape of a structure. In a non-limiting example, set of shape parameters 136 may include information and/or metadata calculated, determined, and/or extracted from set of ultrasonic images, such as, dimensions, angles, curvatures, surface areas, texture, symmetry, and/or the like. In one or more embodiments, set of shape parameters may include a 3D data structure of a structure such as aortic valve 116. In other embodiments, processor 104 may be configured to parameterize features (e.g., edges, textures, contours, and any other characteristics that describe the shape structure) extracted from set of images 112 using CNN described herein. Such parameterization may involve processor 104 to derive one or more shape parameters including one or more morphological descriptors that quantitatively describe structure based on extracted features. In one or more embodiments, processor 104 may be configured to use principal component analysis (PCA) to reduce the dimensionality of set of shape parameters 136, allowing processor 104 to focusing on the most informative shape parameters of set of shape parameters 136 in further processing steps described below.

With continued reference to FIG. 1, in a non-limiting example, set of shape parameters 136 may be generated based on set of images 112 using machine learning model such as, without limitation, a shape identification model 140. In one or more embodiments, 3D reconstruction model 138 includes shape identification model. In one or more embodiments, generating set of shape parameters 136 may include receiving structure training data, wherein the structure training data may include a plurality of image sets as inputs correlated to a plurality of shape parameter sets as outputs. In one or more embodiments, structure training data may be received from Data store 124. For example, and without limitation, structure training data may be used to show each ultrasonic image may indicate a particular set of shape parameters. In one or more embodiments, structure training data may include historical ultrasonic images correlated with historical computed tomography scan data. Such a training dataset may be used to train shape identification model to generate a set of shape parameters representing a structure's shape as a function of a set of ultrasonic images, which may be input into the model in order to receive, as an output, a set of shape parameters. Shape identification model 140 may be trained, by processor 104, using structure training data. Additionally, structure training data may include previously input image sets and their corresponding shape parameter outputs. Shape identification model 140 may be iterative such that outputs may be used as future inputs of shape identification model 140. This may allow the shape identification model 140 to evolve. Processor 104 may be further configured to generate set of shape parameters 136 as a function of set of images 112 using the trained shape identification model 140.

Still referring to FIG. 1, generating set of shape parameters 136 may include performing image processing/segmentation techniques, as described above, prior to implementation of shape identification model 140 in order to optimize performance and runtime of processor 104 and training of model. For example, image segmentation may include normalization and standardization methods performed by computer vision model to ensure that pixel values in images 112 are normalized or standardized to a consistent scale thus aiding convergence during training of shape identification model 140. Image segmentation may include data augmentation techniques such as rotation, scaling, flipping, and translation to artificially increase the size of the training dataset and improve model generalization. Image segmentation may include image enhancement preprocessing techniques like histogram equalization or contrast stretching to enhance relevant features in the images. Image segmentation may include texture and shape descriptors to extract features beyond pixel values, such as texture and shape descriptors, to capture additional information about structures. Image segmentation may include architecture selection methods, as in experiments with different architectures, such as U-Net, DeepLab, or custom architectures, depending on the complexity and characteristics of the images. Image segmentation may include grid Search or random Search processing methods to systematically explore hyperparameter combinations to find the optimal configuration for a 3D model. As previously disclosed, image segmentation may include separating specific structures or regions of interest (ROI) from the background or other structures in a given ultrasonic image, wherein a collection of ROIs may be also incorporated by the shape parameter training data/structure training data.

With continued reference to FIG. 1, processor is configured to receive a 3D model representative of at least an aortic valve 116. In one or more embodiments, processor 104 may use a statistical shape model to generate and/or iteratively refine a 3D model 156 based on a set of shape parameters. As used herein, a "3D model," is a 3D representation of a structure. In one or more embodiments, a 3D model may include a heart model. In one or more embodiments, 3D model may include a representation of the aortic valve 116 of subject and/or surround structure within the heart including an aortic valve 116. A heart model may include a 3D representation of cardiac anatomy. In one or more embodiments, processor may be configured to generate 3D model representative of at least the aortic valve 116. In one or more embodiments, generating the 3D model may include generating the 3D model representative of a surrounding structure of a cardiac anatomy of the subject including the aortic valve 116. In one or more embodiments, 3D model 156 may be generated through a direct 3D reconstruction from a series of (2D) ultrasonic images. In a non-limiting example, set of images 112 may include a plurality of ultrasonic images captured from different angles and positions within and/or around a structure. Processor 104 may be configured to apply one or more 3D reconstruction algorithms, such as without limitation, marching cubes, contour detection and segmentation, active contour models, and/or the like to create a coherent 3D representation e.g., 3D model 156 of structure. In one or more embodiments, such direct 3D reconstruction may leverage the inherent spatial information within set of images 112, providing a direct and intuitive way to model the 3D model 156 of a structure. In a further embodiment, generic 3D modeling techniques may be applied to create the initial 3D model. In one or more embodiments, generic 3D modeling techniques may include surface modeling, solid modeling, or parametric modeling, among others. As an ordinary person skilled in the art, upon reviewing the entirety of this disclosure, will be aware of various 3D reconstruction algorithms that may be used by processor 104 to generate 3D model 156 of structure. As used in this disclosure, a "statistical shape model" (SSM) is a data structure representing, including, and/or utilizing a mathematical model that captures principal modes of variation in shape across a population of structures. In one or more embodiments, SSM may be constructed by analyzing one or more datasets of shapes and identifying, for example, mean shapes and main modes of variation within the one or more datasets. In a non-limiting example, SSM may start with calculation of at least one mean shape, which represents an average geometry of all shapes of a structure in a given dataset, wherein the at least one mean shape may be served as a central reference point for processor 104 to understand different variations. In one or more embodiments, unique SSMs are created for different structure categories, such as different organs or tissues. In a non-limiting example, a first SSM may be created for a first structure category such as kidneys and a second SSM may be created for a second structure category such as hearts. In one or more embodiments, dataset may include, without limitation, structure training data, structure training data, and/or any datasets within ultrasonic image databases described herein. SSM may also identify one or more principal modes of variation within given datasets described herein, wherein the "principal modes of variations," for the purpose of this disclosure, refer to main patterns or directions along which data points vary within dataset. In a non-limiting example, identifying principal modes of variations may include applying principal component analysis (PCA) on given dataset. Additionally, or alternatively, shapes may be described directly using plurality of shape parameter sets (in structure training data). In one or more embodiments, shape parameter sets may correspond to a plurality of modes of variations. Further, one or more statistical constraints (e.g., mean, variance, correlation, boundary, proportion constraint and/or the like) may be introduced into SSM 152 based on the distribution of shape parameters within plurality of shape parameter sets and/or 3D structure dimensions. In one or more embodiments, each shape parameter within a set of shape parameters may be associated with and/or comprise a corresponding parameter range. Such a parameter range may, for example, include a range of values associated with a normal and/or healthy structure. Such a parameter range may be determined based on, for example, a subset of possible values of a parameter which historical healthy structures commonly fall into, as determined from a dataset.

With continued reference to FIG. 1, in one or more embodiments, once modes of variation are extracted, processor 104 may be configured to create a shape representation for any given structure shape within the studied class. In a non-limiting example, 3D model 156 having a shape S may be mathematically represented as $$S = \overline{S} + \sum_{k=1}^{M} a_k \times \phi_k,$$

wherein $\overline{S}$ denotes the mean shape derived from the set of example shapes, M is the number of modes of variation considered, $a_k$ are the coefficients or weights for each mode, and $\phi_k$ are the modes of variation (eigenvectors corresponding to the kth principal component). In one or more embodiments, coefficients $a_k$ may dictate a degree to which each mode of variation is present in shape S. In one or more embodiments, coefficients $a_k$ may vary from positive to negative (or negative to positive) based on the deformation of the 3D model 156 in directions described by each mode of variation. In one or more embodiments, 3D model 156 may include mean shape as described herein. In one or more embodiments, 3D model 156 may include a predictive structure shape that may not have been explicitly seen in the set of example shapes or patient's heart observations. In one or more embodiments, 3D model 156 may be in 3D VOR as described above.

With continued reference to FIG. 1, processor is configured to generate and/or receive 3D Model 156 representative of aortic valve 116 in any way as described in this disclosure. In one or more embodiments, 3D model 156 may be received from a database such as any database as described in this disclosure. In one or more embodiments, 3D model 156 may include a generic 3D model that is representative of a generic heart and/or cardiac anatomy. In one or more embodiments, a generic 3D model may include a three-dimensional representation of a heart, cardiac anatomy and/or anatomical structure that is not specific to any particular, but rather includes features, dimensions and/or structures that have been generated from a plurality of hearts, cardiac anatomies and/or the like of differing individuals. In one or more embodiments, 3D model 156 may be generated on a previous day, previous iteration of a processing of apparatus 100 and/or the like. In one or more embodiments, 3D model 156 may be generated using 3D reconstruction model, generated using initial set of images, generated using ultrasound imaging device and/or generated and/or received in anyway as described in this disclosure.

Still referring to FIG. 1, generating the 3D model 156 may include transforming 3D model 156 to a second 3D model as a function of a plurality of mode changers within SSM 152, wherein each mode changer of the plurality of mode changers is associated with a model feature of 3D model 156. As used in this disclosure, a "mode changer" is an algorithmic component derived from PCA configured to encapsulate a specific mode of variation as described above (representing a distinct way in which the shape of 3D model 156 may deviate from the mean shape). A "model feature," for the purpose of this disclosure, is a distinct, recognizable and quantifiable attribute or characteristic of the 3D model 156. For example, and without limitation, model feature may include an anatomical feature such as the size and curvature of the ventricles, the thickness of the heart wall, the positioning of heart valves or the like. In one or more embodiments, model feature may correspond to at least one shape parameter as described herein. In a non-limiting example, a mode changer may be associated with the size variation of the left ventricle identified within 3D model 156. Such mode changer may be adjusted to modify the volume of the left ventricle, resulting in a second 3D model that mimics potential biological variations or specific patient conditions that is different from original 3D model 156. In one or more embodiments, multiple mode changers of SSM 152 may be adjusted simultaneously. For example, without limitation, the rigid registration might involve translations and rotations to superimpose the shapes; affine registration could incorporate scaling, shearing, and other linear transformations; while non-rigid methods might employ B-splines, thin-plate splines, or diffeomorphic transformations to flexibly map one shape onto another. In one or more embodiments, an averaged position of each corresponding point (or voxel) across all example shapes may be calculated using formula $$\overline{p}_i = \frac{1}{N} \sum_{j=1}^{N} p_{ji},$$

where $\overline{p}_i$ is the mean position of the ith point (or voxel), $p_{ij}$ is the position of the ith point in the jth example shape, and N is the total number of example shapes in the labeled set. In one or more embodiments, principle component analysis (PCA) may be applied to the aligned shapes to extract at least a primary mode of variation. As described herein, a "primary mode of variation" is a mode of variation that have the most significant variability, wherein the "mode of variation," for the purpose of this disclosure, is a specific pattern or direction of a shape change. In one or more embodiments, such significancy may be indicated by the first principal component in PCA. In one or more embodiments, a plurality of modes of variation may be extracted, wherein each mode (or principal component) may represent a specific way the shape of structure may be deformed from the mean shape, determined by one or more eigenvectors of the covariance matrix of the aligned shapes. In a non-limiting example, eigenvector with the highest eigenvalue may represent primary mode of variation which captures the largest amount of shape variability within example shapes, while subsequent modes (eigenvectors) capture decreasing amounts of variability.

Still referring to FIG. 1, additionally, processor 104 may use user feedback to train the machine-learning models described above. For example, structure modeling model and/or shape identification model 140 may be trained using past inputs and outputs of structure modeling model and/or shape identification model 140. In one or more embodiments, if user feedback indicates that a subsequent 3D model outputted by SSM 152 was "bad," then that output and the corresponding input e.g., set of ultrasonic images, corresponding CT-based 3D model may be removed from training data used to train structure modeling model and/or shape identification model 140, and/or may be replaced with a value entered by, e.g., another user that represents an ideal 3D model of the structure given the input the machine learning models originally received, permitting use in retraining, and adding to training data as described above; in either case, machine learning models described herein may be retrained with modified training data. In one or more embodiments, training data such as structure training data and/or structure training data may include user feedback. Further, apparatus 100 may be configured to validate one or more machine learning models described herein against real-world data, identifying areas where machine learning models may be underperforming or misaligned with clinical needs. Such feedback may also be used to guide model training, ensuring that machine learning models are not only accurate but also clinically meaningful and aligned with healthcare or medical professional's needs and priorities.

With continued reference to FIG. 1, processor 104 may be configured to generate an initial 3D model of a structure and/or aortic valve 116. As used in this disclosure, an "initial 3D model" refers to a foundational representation capturing the basic geometric and spatial characteristics of an organ in 3D space. In one or more embodiments, the initial 3D model may provide a "starting point" for subsequent refinement and customization, as described in further detail below, allowing for the integration of more detailed and patient-specific anatomical data. In one or more embodiments, the initial 3D model may be generated through direct 3D reconstruction from a series of two-dimensional (2D) ultrasonic images. In a non-limiting example, the set of images may include a plurality of ultrasonic images captured from different angles and positions within the heart. In one or more embodiments, the initial 3D model may include a generic model of an organ constructed using averaged anatomical data from a sample population characterized as healthy. In an embodiment, the initial 3D model may include a 3D data structure of a generic aortic valve. For the purposes of this disclosure, a 3D model of an aortic valve may be considered generic in cases where the 3D model represents average size and dimensional values for an aortic valve typically observed in healthy individuals. In one or more embodiments, a generic aortic valve model may include average dimensions and/or values within a particular standard deviation derived from a cohort of individuals without clinically significant abnormalities. Processor 104 may be configured to apply one or more 3D reconstruction algorithms, such as, without limitation, marching cubes, contour detection and segmentation, active contour models, and/or the like, to generate a coherent 3D representation, such as an initial model of cardiac anatomy. In some embodiments, this direct 3D reconstruction may leverage inherent spatial information embedded within the set of images 112, providing an intuitive and systematic method to model the initial 3D structure of the heart and/or its components, such as the aortic valve 116. Additionally, generic 3D modeling techniques may be utilized to create the initial 3D model. Such techniques may include surface modeling, solid modeling, parametric modeling, or other well-established approaches. One of ordinary skill in the art, upon reviewing the entirety of this disclosure, will understand the variety of 3D reconstruction algorithms that may be employed by processor 104 to generate an initial 3D model of the structure, aortic valve 116, and/or cardiac anatomy. In one or more embodiments, the initial 3D model may include a 3D representation of the structure and/or aortic valve 116 with an electroanatomical map overlaid on the 3D representation. As used herein, an "electroanatomical map" refers to a visualization of the electrical activity within the heart. In one or more embodiments, such a map may be visualized directly on the 3D representation of a patient's heart, enabling anatomic correlation with electrical conduction data. In one or more embodiments, the initial 3D model may assist in the planning, sizing, or assessment of aortic valve repair or replacement procedures, including transcatheter or surgical approaches. In one or more embodiments, variations or anomalies in the electroanatomical map overlaid on the initial 3D model may indicate complications such as improper device positioning, interference with conduction pathways, or paravalvular leakage following aortic valve implantation.

Additionally, or alternatively, and still referring to FIG. 1, the initial 3D model may be generated based on a plurality of standard anatomical templates, wherein the "plurality of standard anatomical templates," for the purpose of this disclosure, refers to predefined and commonly accepted representations of the human body's anatomical structures. In one or more embodiments, the plurality of standard anatomical templates may be selected from a data store containing an image database as described herein, based on statistical averages or shared anatomical characteristics. In a non-limiting example, the initial 3D model may include a template model selected from a plurality of pre-determined template models. The plurality of pre-determined template models may be generated by the processor based on the plurality of standard anatomical templates prior to generation of the initial 3D model using 3D reconstruction and/or modeling algorithms and techniques as previously described. In one or more embodiments, generating the initial 3D model may include selecting a template model from the plurality of template models based on the set of ultrasonic images and/or set of images 112. In one or more embodiments, the selected template model may represent a typical or average anatomical structure most similar to the subject's aortic valve 116, surrounding aortic root anatomy, or related cardiac structures. Such similarity may be determined using one or more similarity metrics, including but not limited to Structural Similarity Index (SSI), Mean Squared Error (MSE), Peak Signal-to-Noise Ratio (PSNR), Normalized Cross-Correlation (NCC), Pearson correlation coefficient, or similar comparative methods between set of images 112 and each image set stored in the data store. The selected template model may then be adjusted and customized to fit the specific patient's anatomical characteristics using the subject-specific ultrasound data. In one or more embodiments, the template models may represent various anatomical structures such as blood vessels, cardiac chambers, the aortic valve 116, the ascending aorta, or adjacent regions relevant for aortic valve procedures. In one or more embodiments, each template model may correspond to a particular cardiac structure or region of interest for prosthetic aortic valve implantation. In one or more embodiments, selecting the appropriate template model may include identification of the aortic valve or surrounding structures within the set of images. Processor 104 may receive an input indicating the specific anatomical region, or alternatively, may utilize image classification techniques to automatically identify the aortic valve and select the corresponding template model for reconstruction and prosthetic device planning.

With continued reference to FIG. 1, processor 104 may be configured to refine initial 3D model as a function of 3D data structure of structure. In a non-limiting embodiment, refining initial 3D model of structure may include utilizing a statistical shape model (SSM) 152. It should be noted that SSM may not be the only method for refining initial 3D model. A person of ordinary skill in the art, upon reviewing the entirety of this disclosure, will be aware of various methods, such as, without limitation, mesh smoothing techniques, level set method, physics-based simulation, among others may be implemented, by processor 104, to refine initial 3D model described herein. In one or more embodiments, SSM may be constructed by analyzing one or more datasets of shapes and identifying, for example, mean shapes and main modes of variation within the one or more datasets. In a non-limiting example, SSM may start with calculation of at least one mean shape, which represents an average geometry of all the heart shapes in a given dataset, wherein the at least one mean shape may be served as a central reference point for processor 104 to understand different variations. In one or more embodiments, dataset may include, without limitation, any training data and/or any datasets within ultrasonic image databases described herein. SSM may also identify one or more principal modes of variation within given datasets described herein, wherein the "principal modes of variations," for the purpose of this disclosure, refer to main patterns or directions along which data points vary within dataset. In a non-limiting example, identifying principal modes of variations may include applying principal component analysis (PCA) on given dataset. Additionally, or alternatively, shapes may be described directly using plurality of shape parameter sets. In one or more embodiments, shape parameter sets may correspond to a plurality of modes of variations. Further, one or more statistical constraints (e.g., mean, variance, correlation, boundary, proportion constraint and/or the like) may be introduced into SSM based on the distribution of shape parameters within plurality of shape parameter sets.

With continued reference to FIG. 1, refining initial 3D model of structure may include aligning initial 3D model with 3D VOR of structure and/or aortic valve. In an embodiment, aligning initial 3D model with 3D VOR may include matching template model to 3D VOR; for instance, and without limitation, this may involve adjusting the position, orientation, and scale of template model to match the spatial distribution captured in 3D VOR. In one or more embodiments, matching template model to 3D VOR may include matching spatial features, wherein matching the spatial features may further include aligning the surface, boundaries and internal structures of template model with corresponding features in 3D VOR. In one or more embodiments, processor 104 may utilize one or more optimization techniques to achieve a desired alignment; for instance, and without limitation, processor may be configured to minimizing the difference between template model and 3D VOR using iterative closest point (ICP) algorithms, gradient descent, or any other optimization strategies. Additionally, alignment of template model with 3D VOR may also allow incorporation of patient-specific details (e.g., patient profile) into initial 3D model to form a final model as described in further detail below.

In a non-limiting example, and still referring to FIG. 1, refining initial 3D model of structure and/or cardiac anatomy may include deforming, using processor 104, template model to match 3D data structure of structure. As used in this disclosure, "deforming" means altering the geometric structure of a structure e.g., template model in a systematic and controlled manner to align the structure with the spatial characteristics captured in another structure e.g., 3D VOR. In one or more embodiments, processor 104 may utilize one or more mathematical deformation models such as, without limitation, B-splines, radial basis functions, or other deformation functions to control and guide the deformation process of template model. In one or more embodiments, one or more constraints listed above may be applied, by processor 104, based on anatomical knowledge, biomechanical properties, or other relevant factors to ensure that the deformation of template model is realistic and consistent with physiological principles as would be understood and/or expected by an ordinary person skilled in the art.

Still referring to FIG. 1, additionally, or alternatively, refining initial 3D model of structure may also include validating template model or deformed template model against 3D data structure or additional data such as, without limitation, expert input, adjust parameters, and/or the like. Such validation process may ensure that the refined model accurately represents the underlaying structure. In one or more embodiments, expert input may include any user input entered through a user interface as described in further detail below. In a non-limiting example, expert input may include, without limitation, clinical assessment, anatomical knowledge, or other professional insights that guide and evaluate the refinement process inputted to apparatus 100 by one or more users including medical professionals, subjects, patients, and/or any other related individuals. In a further embodiment, validating template model or deformed template model against 3D data structure may also include fine-tuning defamation controls, alignment settings, other model characteristics or properties to achieve desired alignment with 3D VOR or additional data. In one or more embodiments, other information that is incorporated and codified within template model/deformed template model and/or 3D data structure such as medical imaging, biomechanical simulations, patient-specific data/metadata may be validated and cross-verified. At least a machine-learning process, for example a machine-learning model described herein, may be used to validate by processor 104. In one or more embodiments, refining the initial 3D model includes deforming and/or refining the initial 3D model to match the 3D data structure representing the aortic valve. Processor 104 may use any machine-learning process described in this disclosure for this or any other functions.

With continued reference to FIG. 1, in one or more embodiments, embedded values described herein may be employed in the refinement process of initial 3D model of structure. In a non-limiting example, the embedded values may contribute to SSM by providing additional parameters that guide the deformation and alignment of the template to match 3D VOR. Embedded values such as, without limitation, presence indicators may be used by processor 104 to guide the deformation process by providing targets for alignment; for instance, and without limitation, SSM may be configured to identify specific target areas where initial 3D model e.g., a 3D LA model that needs to be deformed. Presence indicators, in this case, may reveal a bulge in LA wall that is not present in initial 3D model. In one or more embodiments, presence indicators may define the exact shape of the bulge in LA wall. Processor 104 may then deform initial 3D model, particularly the wall to match the bulge defined by presence indicators in 3D VOR.

Still referring to FIG. 1, generating 3D model 156 includes determining a level of uncertainty at least at one location of a plurality of locations of the 3D model 156 based on the set of shape parameters 136. A location may refer to each voxel of plurality of voxels, cells, geometric marker, and all other identifying markers/data points of a model as described throughout this disclosure. A plurality of locations may refer to the surface of 3D model 156, such as a set of pixels or a region on a model. "Uncertainty," as used herein, refers to the lack of confidence or precision in a model's predictions. In one or more embodiments, the level of uncertainty may be derived from variability within the distribution of shape parameters, image quality assessment, measurement errors and/or the like. In a non-limiting example, greater changes in structure geometry (indicated by the plurality of shape parameters) may correspond to a greater level of uncertainty at that location. This may be used to inform clinical decisions, for example, areas of high uncertainty may be avoided when planning a pathway for surgical intervention or additional imaging may be requested to reduce uncertainty in critical areas.

Still referring to FIG. 1, levels of uncertainty may refer to categories of uncertainty such as epistemic uncertainty, aleatoric uncertainty, model parameter uncertainty, pixel-wise uncertainty, boundary uncertainty, uncertainty in time series data, predictive uncertainty, systematic uncertainty, model output uncertainty, and the like. Epistemic uncertainty arises from a lack of knowledge or information. For example, limited training data for certain cardiac pathologies may contribute to higher epistemic uncertainty. Aleatoric uncertainty, also known as data uncertainty, results from inherent randomness or variability in the data. For example, variability in cardiac anatomy among different patients or imaging modalities introduces aleatoric uncertainty. Model Parameter Uncertainty is uncertainty associated with the model parameters, indicating how well the model has learned the underlying patterns in the training data. For example, variations in model parameters due to the stochastic nature of the optimization process contribute to parameter uncertainty. Pixel-wise Uncertainty is associated with individual pixels in the image. It provides a confidence measure for each pixel in the segmentation mask. For example, certain regions of a structure may be more challenging to segment accurately, leading to higher pixel-wise uncertainty. Boundary Uncertainty is related to the boundaries between different structures or regions in the image. For example, the precise delineation of the endocardium or epicardium may be uncertain in regions where the boundaries are not well-defined. Regarding uncertainty in Time Series Data, in tasks involving sequential data, such as cardiac imaging over time, uncertainty can be related to variations in the temporal dimension. For example, segmentation of dynamic structures like the beating heart involves handling uncertainty associated with different phases of the cardiac cycle. Predictive Uncertainty is uncertainty in the model's predictions for unseen data points. For example, when the model encounters a novel pathology or an atypical structure, predictive uncertainty measures its confidence in providing accurate segmentation. Systematic Uncertainty is uncertainty stemming from systematic errors or biases in the data collection process or the model architecture. For example, if the training data is biased towards a specific demographic, the model may exhibit uncertainty when applied to a more diverse patient population. Model Output Uncertainty is uncertainty associated with the actual output of the model, indicating how confident the model is in its segmentation predictions. For example, the model may output a segmentation mask with a probability or confidence score for each pixel, reflecting the uncertainty associated with that pixel's classification.

Still referring to FIG. 1, a level of uncertainty may include a degree, statistical measure, percentage, or variable whether linguistic or numerical, and the like identifying a range of uncertainty. For example, processor 104 may generate probability scores/confidence scores for locations of a model, indicating the model's confidence in its predictions. Calibration plots can be used to assess how well these confidence scores align with the true accuracy. Processor 104 may perform a threshold analysis to investigate how varying decision thresholds for classification or segmentation affects the trade-off between sensitivity and specificity in uncertain regions. Threshold analysis may include task-specific metrics for clinical relevance. For example, in cardiac image segmentation, critical regions like the myocardium may have stricter uncertainty thresholds compared to less critical regions. Processor 104 may implement Bayesian Neural Networks (BNNs) to perform posterior predictive checks to evaluate the agreement between the model's predictions and the observed data, such as data store 124, considering the uncertainty represented by the posterior distribution in Bayesian frameworks. In various embodiments, a level of uncertainty may be metrics determined by processor 104, such as Pixel-wise Uncertainty Metrics, Boundary Displacement Error (BDE), Uncertainty-Aware Loss Functions, Calibration Metrics, and the like.

Still Referring to FIG. 1, processor 104 is configured to generate a map regarding one or more levels of uncertainty. A "map," as used herein, refers to a visualization. Map may be level(s) of uncertainty to be visualized on the 3D model 156. Map may include a color-coded heatmap, including other visual cues, symbols or indicators that alert a user to areas of 3D model 156 that may require extra caution when used for planning or guidance during a medical procedure. For example, after obtaining the segmentation results from 3D model 156, map may be generated. Map may highlight the uncertainty or confidence level associated with each pixel in the segmentation. Assigning colors to different intensity levels in map allows for an intuitive visualization. Typically, warmer colors (e.g., red, or yellow) might represent high uncertainty, while cooler colors (e.g., blue, or green) could indicate low uncertainty. The color-coding can be adjusted based on specific thresholds or clinical requirements.

Still referring to FIG. 1, generating map may include methods such as Class Activation Mapping (CAM). Class Activation Mapping is a technique that originated for image classification tasks and has been extended to provide visual insights into the regions of an image that are most important for a particular class. CAM allows the visualization of the spatial attention of a convolutional neural network (CNN) by generating heat maps that highlight discriminative regions. CAM may be applied to the last convolutional layer of a CNN. The features extracted by this layer capture high-level semantic information, making it suitable for visualizing the importance of different regions in an image. CAM is typically applied to the last convolutional layer of a CNN. The features extracted by this layer capture high-level semantic information, making it suitable for visualizing the importance of different regions in an image. The output of the global average pooling is then fed into a fully connected layer with a softmax activation function. This converts the features into class scores, indicating the likelihood of the image belonging to different classes. The CAM algorithm computes a weighted sum of the original feature maps based on the weights of the fully connected layer. These weights are determined during the training process and represent the importance of each feature map for a specific class. The weighted sum is applied to the original feature maps, producing a single heat map. This heat map highlights the regions of the input image that contributed most to the prediction for the target class. The generated heat map can be overlaid on the input image, visually indicating which regions are most relevant for the predicted class. Typically, warmer colors (e.g., red, or yellow) represent higher activation or importance.

Still Referring to FIG. 1, generating map may include Grad-CAM (Gradient-weighted Class Activation Mapping). Grad-CAM is an extension of Class Activation Mapping (CAM) that enhances the localization capabilities by incorporating gradient information from the final convolutional layer of a neural network. Grad-CAM helps to generate heat maps that highlight discriminative regions in an image, providing more fine-grained insights into where a convolutional neural network (CNN) is focusing its attention when making predictions. In traditional CAM, the last convolutional layer's feature maps are linearly combined to obtain a weighted sum, and the resulting weights are used to create a heat map that highlights relevant regions for a specific class. Grad-CAM improves upon CAM by introducing gradient information. It computes the gradients of the predicted class score with respect to the feature maps of the last convolutional layer. Grad-CAM retains the global average pooling (GAP) operation applied after the last convolutional layer, as it is an integral part of CAM. The GAP operation condenses the spatial information into a single value per feature map. The gradients obtained in the previous step are used to calculate the importance of each feature map. These gradients represent the importance of each feature map in contributing to the final prediction. A weighted sum is computed using these gradients, and this is combined with the original feature maps. The computed sum goes through a ReLU activation function, discarding any negative values. This step emphasizes positive contributions and suppresses negative ones. The ReLU-activated weighted sum is linearly combined with the original feature maps to produce a weighted combination. This combination retains spatial information and helps create a more accurate heat map. The resulting heat map is often normalized to enhance visualization, ensuring that the values are within a specific range (e.g., between 0 and 1). The final heat map generated by Grad-CAM is then overlaid on the input image, highlighting the regions of interest for the predicted class. The intensity of the heat map indicates the importance of different regions. Grad-CAM enhances the interpretability and explainability of deep learning models, allowing practitioners and researchers to understand which parts of an image are crucial for a particular prediction. This is particularly valuable in applications such as medical imaging or any domain where understanding the decision-making process is critical.

Still Referring to FIG. 1, generating map may include utilizing a "SmoothGrad technique," a technique designed to improve the interpretability of neural network predictions by reducing the noise in the attribution maps or heat maps generated by visualizing gradients. It is particularly useful for understanding the decision-making process of deep learning models, especially in scenarios where the explanations need to be robust and less sensitive to input perturbations. The primary goal of SmoothGrad is to enhance the visual quality of attribution maps generated by visualizing gradients. Attribution maps highlight the regions in the input that contribute most to a model's prediction. SmoothGrad aims to reduce the impact of noise in these maps, providing more stable and interpretable visualizations. The key idea behind SmoothGrad is to introduce perturbations to the input data. Instead of attributing the prediction solely to the gradients calculated with respect to the original input, the gradients are averaged over multiple perturbed versions of the input. By averaging the gradients over multiple perturbed samples, SmoothGrad helps reduce the impact of noise or irrelevant features in the attribution maps. This is particularly beneficial when dealing with complex or noisy data sets. Perturbation techniques include adding Gaussian noise, random rotations, or random translations to the input data. These perturbations create variations in the input while preserving the essential features, leading to more stable and reliable attribution maps. For each perturbed input, gradients are calculated with respect to the model's output. These gradients are then averaged over all perturbed samples. This process smoothens the attribution map by reducing the influence of random noise. The averaged gradients may undergo normalization or scaling to ensure that the values are interpretable and within a specific range. This step can enhance the consistency and comparability of the attribution maps generated. The final step involves generating a heat map using the smoothed gradients. The heat map represents the attribution of different regions in the input to the model's prediction, providing a clearer and more stable visualization.

Still Referring to FIG. 1, generating map may include implementing one or more Gaussian Processes. A Gaussian Process is a collection of random variables, any finite subset of which has a joint Gaussian distribution. In simpler terms, it is a distribution over functions rather than a distribution over finite-dimensional vectors. Gaussian Processes (GPs) can be applied to generate heat maps in various ways, particularly in the context of regression tasks where one would want to predict continuous values across a spatial domain. Given a set of observed data points, the GP can predict the values at unobserved locations in the spatial domain. Importantly, it also provides uncertainty estimates associated with these predictions. This uncertainty can be visualized as a heat map. The predicted values from the GP represent the main heat map, indicating the expected values across the spatial domain. The uncertainty associated with each prediction can be visualized as an uncertainty heat map. This uncertainty heat map provides insights into regions where the model is less confident about its predictions. Overlay of the main heat map and the uncertainty heat map on the original spatial data may create a composite visualization. Warmer colors in the main heat map might represent higher predicted values, while the uncertainty heat map's intensity could indicate regions where the model's predictions are less certain.

Still referring to FIG. 1, processor 104 may be configured to overlay map onto 3D model 156. In one or more embodiments, the overlay may be placed on 3D model 156 and go through a refinement process as described above. In one or more embodiments, overlaying 3D model 156 with map may include utilizing interactive visualization techniques, which may allow user-mediated augmentation of the set of images. Overlaying map on a model may include implementing spatial alignment methods, texture mapping techniques wherein the color information from the heat map is mapped onto the vertices or faces of the 3D model, shader programs that define how the heat map values influence the final appearance of the 3D model, visualization software or programming libraries that support 3D rendering and overlay capabilities, interactivity visualization, quality control methods, and the like. For example, texture mapping may include UV Mapping wherein each point on the surface of a 3D model is associated with a set of texture coordinates often denoted as U and V. These coordinates are analogous to the X and Y coordinates on a 2D image. UV mapping establishes the correspondence between points on the 3D model and pixels on the 2D texture. In another example, interactive visualization may create visual representations of data that users can interact with and manipulate. This approach allows users to explore and analyze data dynamically, gaining insights through direct engagement with the visual representation. For example, mouse interactivity may allow users to interact with visual elements using mouse actions, such as hovering over data points for additional information, clicking to drill down into details, or dragging to pan and zoom. Filtering and Selection capabilities may allow a user to filter data based on specific criteria or select subsets of data for closer examination. This is particularly useful when dealing with large datasets. Spatial Exploration may allow users to zoom in to explore details or pan to navigate across the space.

Still referring to FIG. 1. in one or more embodiments, an ultrasonic image taken during a medical procedure or synthesized for machine learning training purposes may be overlaid at a corresponding location or 3D model. For example, a TEE frame taken during a TEE procedure or synthesized for machine learning training purposes may also be overlaid at a corresponding location or 3D model. Overlaying the ultrasonic image may include registering the ultrasonic image to the generated 3D model 156 using the image processing model. For example, the processing system may include at least a processor and a memory communicatively connected to the at least a processor, wherein the memory contains instructions configuring the at least a processor to receive a 3D model related to a structure of a subject, identify a region of interest within the 3D model, wherein identifying the region of interest includes locating at least a point of view on the 3D model and determining a view angle corresponding to the at least a view origin, wherein the at least a point of view and the corresponding view angle define at least one field of view that include at least a portion of the 3D model. The at least a processor may be further configured to generate at least a medical image as a function of the region of interest using an image generator, wherein the at least a medical image captures an anatomical structure of the at least a portion of the 3D model.

Still referring to FIG. 1, processor 104 may be configured to receive a reference model 162 of structure and/or a reference model 162 of the aortic valve. In one or more embodiments, reference model 162 may be consistent with 3D model 156. As used in this disclosure, a "reference model" is a predefined representation of an anatomical structure that serves as a baseline for comparison, analysis, or guidance. In an embodiment, reference model 162 may be aligned with the initial 3D model as described above. In one or more embodiments, reference model 162 may be used during imaging and interventional procedures, such as transcatheter aortic valve replacement (TAVR), to enhance visualization, orientation, and navigation. In an embodiment, the reference model 162 may serve as a conversion layer, wherein specific anatomical locations defined on the reference model 162, such as the aortic annulus, coronary ostia, or sino-tubular junction, can be mapped to corresponding coordinates on 3D model 156. Processor 104 may identify and translate positions of clinical interest (e.g., prosthetic valve landing zones, catheter tip location, or calcified regions) from the reference model 162 to the real-time 3D model 156 to support procedural planning and execution. In one or more embodiments, reference model 162 may be derived from prior imaging data (e.g., preoperative CT, TEE, or MRI scans), standardized anatomical atlases, or computed from historical patient datasets. This enables accurate alignment with intraoperative imaging modalities like real-time ultrasound, facilitating guidance of ultrasound imaging device during device navigation and deployment. For example, in aortic valve repair or replacement procedures, the reference model 162 may represent an idealized or average anatomical structure of a healthy aortic valve. This model may be overlaid onto real-time ultrasound images to assist in anatomical localization, identification of abnormalities (e.g., annular calcification or asymmetric leaflet motion), and confirmation of prosthetic device positioning. This comparative approach can improve accuracy, reduce procedural errors, and enhance clinical outcomes. Additionally, and/or alternatively, reference model 162 may support automated or semi-automated segmentation of the aortic valve and surrounding anatomical landmarks by providing structural templates for comparison. In one or more embodiments, this may include identifying the aortic annulus, leaflets, and left ventricular outflow tract to facilitate planning and deployment of a prosthetic valve. In one or more embodiments, reference model 162 may be used to track or localize interventional tools, such as catheters, guidewires, or delivery systems, within the heart. Ultrasound imaging device may detect the catheter's position in real time, and processor 104 may localize this position within the reference model 162. The system may then convert these coordinates to corresponding positions within 3D model 156 to provide clinicians with spatially accurate guidance. In one or more embodiments, computational operations, localization algorithms, or coordinate transformations may be calculated within the reference model 162 to reduce processing complexity and standardize outputs. A secondary algorithm may be applied to transform coordinates from reference model 162 to 3D model 156 by aligning common anatomical landmarks, ensuring consistency and accuracy across models.

With continued reference to FIG. 1, processor 104 may be configured to receive at least a valve model 132 representative of one or more prosthetic devices used in aortic valve repair or replacement procedures. In one or more embodiments, processor 104 is configured to receive a 3D model 156 representative of the aortic valve anatomy and/or a valve model 132 representative of a prosthetic device 128. For the purposes of this disclosure, a "valve model" refers to a three-dimensional (3D) digital representation of a prosthetic device designed for transcatheter or surgical aortic valve interventions. In one or more embodiments, the valve model 132 may include representations of prosthetic devices such as, but not limited to, balloon-expandable or self-expanding transcatheter heart valves (THVs), sutureless valves, or surgical bio-prostheses. Valve model 132 may correspond to commercially available aortic valve prostheses from one or more manufacturers and may reflect the device's geometry, frame structure, leaflet configuration, and radiopaque markers. In one or more embodiments, valve model 132 may be consistent with 3D model 156, which is generated from the set of ultrasound images using ultrasound imaging device. Processor 104 may retrieve a valve model 132 from data store 124, where a library of preloaded, validated 3D models of prosthetic devices 128 is stored for procedural planning and simulation. In one or more embodiments, a user (e.g., a clinician or interventional cardiologist) may manually select or input a desired valve model 132 through a user interface communicatively connected to processor 104. The selected valve model may then be virtually positioned within the aortic root of the 3D anatomical model to simulate valve deployment, assess annular fit, and evaluate potential complications such as paravalvular leakage or obstruction of coronary ostia. Processor 104 may also receive real-time sets of images from ultrasound imaging device, which may capture the passage of the prosthetic device 128 through vascular structures and into the left ventricular outflow tract (LVOT) via transfemoral or transapical access. Processor 104 may extract spatial and morphological features from the incoming images to dynamically update or align valve model 132 based on the orientation, positioning, and deployment status of the actual prosthetic valve.

With continued reference to FIG. 1, in one or more embodiments, receiving at least a valve model 132 may include extracting at least one cardiovascular characteristic datum from a set of images 112, determining a valve model datum 164 as a function of the cardiovascular characteristic datum, and/or generating a valve model 132 as a function of the valve model datum. In one or more embodiments, generating valve model 132 may include identifying and/or selecting valve model 132 from a plurality of prosthetic aortic valve models located in data store 124. For the purposes of this disclosure, a "cardiovascular characteristic datum" refers to data elements representing anatomical or functional features of the aortic valve complex. For example, and without limitation, cardiovascular characteristic datum may include annular diameter, valve orifice area, leaflet calcification severity, aortic root dimensions, left ventricular outflow tract (LVOT) dimensions, and aortic valve opening angle. In one or more embodiments, cardiovascular characteristic datum may be consistent with spatial or functional features extracted from aortic valve structures. These data may be derived using image processing algorithms, machine learning-based segmentation tools, manual clinician input, or combinations thereof. In one or more embodiments, processor 104 may determine cardiovascular characteristic datum using ultrasound images, such as through automated segmentation, annotation, deep-learning-based landmark detection. A "valve model datum" for the purposes of this disclosure refers to one or more data elements representing physical or functional properties of a prosthetic device. For example, valve model datum 164 may represent parameters such as frame diameter, radial expansion force, leaflet height, skirt length, or anchoring mechanism characteristics. In one or more embodiments, valve model datum 164 may be used to determine which type and size of prosthetic device 128 best corresponds to the specific anatomy and pathology of subject 120. For example and without limitation, processor 104 may compare valve model datum 164 against cardiovascular characteristic datum to identify a prosthetic device that provides optimal sealing, minimizes paravalvular regurgitation, and ensures compatibility with coronary ostia anatomy. In one or more embodiments, processor 104 may restrict selection to devices with expansion profiles or deployment trajectories that fall within clinically acceptable safety thresholds (e.g., ≤20% oversizing of annulus, no obstruction of coronary arteries). Valve model 132 may be generated and/or selected to quantitatively and visually reflect the selected prosthetic device.

With continued reference to FIG. 1, valve model datum 164 may represent sizing, configuration, and orientation parameters for a prosthetic device 128. Processor 104 may determine the optimal dimensions and deployment angles necessary to restore aortic valve competence while maintaining hemodynamic performance and minimizing shear stress across the leaflets or LVOT. The physical parameters used in valve model 132 may include stent frame diameter, effective orifice area, skirt height, and delivery catheter trajectory. In one or more embodiments, valve model datum 164 may also include functional outcome metrics such as target coaptation height, annular expansion force, and predicted paravalvular leak zone. Cardiovascular characteristic datum may further describe aortic valve pathologies such as bicuspid morphology, calcific degeneration, aortic stenosis severity, or annular asymmetry, which are used to refine valve model selection.

With continued reference to FIG. 1, in one or more embodiments, valve model datum 164 may indicate the type of prosthetic device 128 appropriate for a specific therapeutic approach in order to treat an improper aortic valve. This may include, without limitation, balloon-expandable transcatheter heart valves (e.g., SAPIEN series), self-expanding valves (e.g., Core Valve/Evolut series), mechanically anchored valves, or surgical bioprosthetic valves. Selection may depend on disease etiology (e.g., calcific aortic stenosis vs. aortic insufficiency), annular sizing, degree of calcification, and access route considerations. For example, a balloon-expandable valve may be preferred in patients with concentric annular calcification and low coronary take-off, whereas self-expanding valves may be better suited for elliptical annuli or large aortic roots. Additional parameters such as aortic angulation, sinus of Valsalva dimensions, and proximity to coronary ostia may be integrated into valve model datum 164 to guide selection and deployment planning. In one or more embodiments, processor 104 may correlate valve model datum 164 with the patient-specific 3D model (i.e., 3D model 156) reconstructed from set of images 112 to simulate device placement and predict outcomes such as paravalvular leak, valve embolization risk, LVOT obstruction, post-implant pressure gradients and/or the like.

With continued reference to FIG. 1, in one or more embodiments, processor 104 may be configured to generate device training data specific to aortic valve repair or replacement procedures. In a non-limiting example, device training data may include correlations between exemplary cardiovascular characteristic datums associated with a plurality of aortic valves and exemplary aortic valve model datums 164 corresponding to various prosthetic devices 128. In one or more embodiments, device training data may be stored in a data store 124. Device training data may be sourced from expert clinician annotations, historical procedural datasets, simulation results, public registries, or other clinical repositories. For example, a clinician may provide labeled examples of successful aortic valve replacements, including input on anatomical features (e.g., annular size, leaflet calcification patterns, aortic root diameter) and associated prosthetic valve device choices (e.g., self-expanding valve, balloon-expandable valve, specific frame dimensions or skirt configurations). These labeled examples may be stored as part of device training data. In one or more embodiments, this data may be used to train a machine learning model to map cardiovascular characteristic datums to corresponding valve model datums 164 and/or prosthetic aortic valve models 132. For instance, a trained model may learn to recommend a 26 mm balloon-expandable valve for a patient with severe aortic stenosis and an annular diameter of 23 mm with high calcification burden.

With continued reference to FIG. 1, processor 104 may update device training data iteratively through a feedback loop, incorporating new patient image data (e.g., set of images 112), updated cardiovascular characteristic datums, procedural outcomes (e.g., residual gradient, valve positioning accuracy, paravalvular leak severity), and revised valve model datums 164. In one or more embodiments, processor 104 may generate or update a device machine-learning model using supervised, unsupervised, or reinforcement learning techniques. The device machine-learning model may be trained or fine-tuned on device training data to improve prosthetic aortic valve selection and predict procedural success based on specific patient anatomy and pathology. For example, the model may learn that patients with horizontal aortas and large annuli may benefit from self-expanding valves with high radial force, while others with smaller sinuses and aortic root dilation may require low-profile balloon-expandable valves.

With continued reference to FIG. 1, processor 104 may apply a cohort classifier to categorize a patient, the patient's heart, or the set of images 112 into a defined patient cohort. This classification may be based on morphological, pathological, or historical procedural characteristics of the aortic valve. In one or more embodiments, classification may include calcific aortic stenosis (CAS) vs. aortic regurgitation (AR), bicuspid vs. tricuspid valve morphology, presence of aortic root dilation, prior aortic valve replacement and/or the like. The cohort classifier may be trained using historical cohort training data composed of labeled clinical cases that include imaging data, anatomical annotations, procedural outcomes, and prosthetic device selection. In one or more embodiments, valve model datum 164 may be determined based on the cohort classification, guiding processor 104 to recommend a class or type of prosthetic devices 128 suitable for the patient subgroup. For example, for a bicuspid aortic valve cohort with asymmetric calcification, the classifier may recommend a specific self-expanding valve with conformable frame geometry. In one or more embodiments, the output of the cohort classification process may be used to refine device training data in a continuous learning loop. Additionally, device training data generation and training of the device machine-learning model may occur in real time, either during pre-operative planning or intra-operative image acquisition and analysis.

With continued reference to FIG. 1, processor 104 may be configured to determine a valve model datum 164 and receive valve model 132 as a function of valve model datum 164. In one or more embodiments, determining valve model datum 164 may include simulating the placement of a plurality of prosthetic devices 128 within at least a 3D model 156, as a function of at least cardiovascular characteristic datum. In one or more embodiments, processor 104 may be configured to further receive repair-specific parameters such as coaptation height, left ventricular outflow tract (LVOT) clearance, or annular remodeling targets using set of images 112 and further select prosthetic device 128 as a result. In a non-limiting example, processor 104 may utilize finite element analysis (FEA), computational fluid dynamics (CFD), or tissue-device interaction models to simulate how various prosthetic devices 128 interact with the aortic root and valve complex, including effects on leaflet opening, calcification displacement, and hemodynamic gradients. In one or more embodiments, determining valve model datum 164 may include determining a pass datum as a function of cardiovascular characteristic datum and device-specific interaction parameters. For the purposes of this disclosure, a "pass datum" is a data element indicating whether a prosthetic device 128 is suitable for use in the patient's anatomy based on virtual placement or simulation output. In one or more embodiments, pass datum may include a position datum representing the spatial alignment of the prosthetic valve during simulated deployment. In one or more embodiments, pass datum may include an anchor datum representing the fixation stability or annular fit of the device. In one or more embodiments, pass datum may include a placement size datum indicating the device's deployed configuration, such as frame diameter, skirt height, or leaflet projection. In one or more embodiments, processor 104 may evaluate multiple prosthetic device 128 against the patient-specific 3D model (i.e., 3D model 156) and generate a pass/fail matrix to assist in selecting the optimal prosthetic valve. In one or more embodiments, this simulation-based planning may reduce procedural risks such as paravalvular leak or coronary obstruction, guide device selection, and improve procedural efficiency and clinical outcomes in aortic valve replacement.

With continued reference to FIG. 1, in one or more embodiments, receiving valve model 132 may include receiving the valve model 132 as a function of valve model datum 164. In one or more embodiments, valve model datum 164 may indicate a specific aortic valve or prosthetic device 128 to be utilized in a catheter-based or transcatheter aortic valve replacement (TAVR) procedure. In one or more embodiments, valve model datum 164 may include a size specification or device classification, wherein processor 104 is configured to identify and select at least one prosthetic device 128 that conforms to the parameters indicated within valve model datum 164. In an embodiment, a data repository such as data store 124 may maintain a library of aortic valve models 132, wherein processor 104 is configured to retrieve or select a valve model 132 consistent with the specified characteristics outlined in valve model datum 164. For example, and without limitation, if valve model datum 164 indicates a self-expanding valve appropriate for elliptical annuli with heavy calcification, processor 104 may identify a valve model 132 with corresponding radial force characteristics and supra-annular leaflet position. Similarly, if valve model datum 164 specifies the need to minimize LVOT obstruction in a small annulus, processor 104 may select from balloon-expandable valve models with low-profile delivery systems and tailored skirt geometries.

With continued reference to FIG. 1, In one or more embodiments, valve model 132 may represent a digital 3D representation of a prosthetic device 128 which is intended for pre-procedural simulation or intraoperative planning. In one or more embodiments, valve model datum 164 may further specify device attributes such as anchoring features, tissue compatibility, material composition (e.g., nitinol, polyester fabric), or device category (e.g., semi-rigid vs. fully flexible ring). In one or more embodiments, processor 104 may be configured to receive valve model 132 as a function of valve model datum 164.

With continued reference to FIG. 1, in one or more embodiments, processor 104 may be configured to identify one or more anomalies within ultrasound image and/or sets of images 112 that may be indicative of potential pathological changes associated with aortic valve disease. As used herein, an "anomaly" refers to a data point or set of data points that deviates from expected or normative values derived from a reference anatomical model, such as a generic 3D heart model. These deviations may suggest abnormalities relevant to aortic valve function or morphology. For example, and without limitation, anomalies within the set of images may include irregularities in cusp thickness, calcific burden, restricted motion, leaflet prolapse, annular enlargement, or abnormal echogenic patterns that deviate from healthy aortic valve anatomy. In one or more embodiments, anomalies may relate to changes in the spatial relationship or geometric dimensions of the aortic root, annulus, or left ventricular outflow tract (LVOT). In one or more embodiments, processor 104 may compare cardiovascular characteristic datum extracted from the set of images to corresponding generic cardiovascular characteristic datum derived from a generic 3D model of a healthy heart. In one or more embodiments, deviations in values between cardiovascular characteristic datum and generic cardiovascular characteristic datum, such as leaflet curvature, annular diameter, cusp thickness, or coaptation height, may be identified as anomalies. In one or more embodiments, anomalies may include spatial distortions, which may refer to differences in anatomical measurements (e.g., aortic annulus perimeter, sinus of Valsalva diameter, or inter-commissural distances) between the patient's heart and the generic 3D model. In one or more embodiments, upon identification of anomalies, processor 104 may be configured to generate a patient-specific 3D model by modifying a generic 3D model to reflect the identified aortic valve anomalies. The modification may include altering values within a 3D voxel grid or mesh structure, such as adjusting the geometry of the aortic valve cusps, annular shape, or aortic root to match the patient's unique anatomy. In an embodiment, only those features identified as anomalous may be modified, while features not visible or identifiable within the ultrasound image may retain default values from the generic 3D model. In one or more embodiments, identification of aortic valve anomalies and generation of the 3D model may further enable processor 104 to select or recommend a valve model 132 and/or prosthetic device 128 appropriate for treating the identified pathology. For example, processor 104 may correlate a detected annular enlargement with a specific size or shape of a prosthetic device 128 or select a device with sealing features suited for heavy calcification in the aortic valve.

With continued reference to FIG. 1, in one or more embodiments, data store 124 may include a plurality of valve models 132, each digitally representative of options available for implantation during aortic valve intervention. In one or more embodiments, processor 104 may utilize valve model datum 164 to generate a query that identifies at least one available valve model from the plurality of available valve models within the data store. For purposes of this disclosure, an "available valve model" may be defined as a digital 3D representation of a prosthetic device 128 that both meets the anatomical criteria of a subject and is physically available for use. For example, available valve model may include prosthetic devices that are present within a clinical inventory or supplier systems. In another non-limiting example, an available valve model may include a valve model 132 representative of a prosthetic device 128 that would be suitable for implementation within a particular subject and also available for use by a medical professional. In another non-limiting example, an available valve model may represent a balloon-expandable aortic valve with specific frame height and skirt dimensions that is in stock and suitable for implantation in a patient with a small annulus and high calcific burden. In one or more embodiments, data store 124 may include valve models 132 classified and/or grouped by dimensions, anatomical compatibility, therapeutic purpose (repair vs replacement), availability status and/or the like. In one or more embodiments, the data store may reflect real-time inventory levels in a hospital or clinical facility, ensuring that selected devices are not only appropriate but are also readily available.

With continued reference to FIG. 1, processor 104 may be configured to formulate and execute a search query, such as an SQL command based on valve model datum 164 in order to identify and/or retrieve valve model 132 from datastore. A "search query" for the purposes of this disclosure is a structured request for data. In one or more embodiments, search query may be used to search a database for a particular set of information such as valve models 132. In one or more embodiments, search query may include conditions for the desired type of data, such as a valve model 132 with a particular diameter and/or length. In one or more embodiments, search query may be in the form of a structured query language (SQL). In one or more embodiments, search query may include the data fields to retrieve, such as for example, diameter, material, device classification and/or the like. in one or more embodiments, search query may include source tables in which data should be retrieved from. In one or more embodiments, search query may include conditions and/or filters. For example, and without limitation, search query may include search conditions, such as minimum and maximum diameters, only prosthetic devices 128 belonging to a particular category and/or the like. In one or more embodiments, search query may retrieve data fields such as device diameter, leaflet span, anchoring mechanism, and availability status of a plurality of valve models 132. In one or more embodiments, search query may contain filters or conditions (e.g., "ring height≤5 mm") and may span multiple source tables or nodes within the database structure. For example, a query generation node may instruct processor 104 to access the device type classification table, filter for all clip-type devices, further filter for grasping arm dimensions compatible with posterior leaflet prolapse, cross-reference inventory table for in-stock units and/or the like. In one or more embodiments, search query may include a plurality of nodes. A "node" as referred to herein refers to an element or entity within a data structure. A node in the context of database queries, also referred to as a 'query generation node' may refer to a step or action in the process of generating a query. For example, and without limitation, node may include a step of accessing a database of files, accessing a particular classification of files and the like. In one or more embodiments nodes may include steps such as but not limited to receiving data identifying an initial set of data on database. In one or more embodiments, each node may represent a specific piece of information or condition related to the request. In one or more embodiments, nodes may be used to find and retrieve information within database. In one or more embodiments, nodes may be specific to what information should be retrieved. In one or more embodiments, nodes may include operations like table scans, index lookups, filtering conditions, and the like. In one or more embodiments, processor 104 may be configured to generate an SQL query and/or a search query including a plurality of nodes wherein each node may refer to a specific step in a process of data retrieval. In one or more embodiments, nodes may be used to filter information within database based on valve model datum 164. In one or more embodiments, nodes may provide instructions on how to identify and select the relevant data from database. In one or more embodiments, nodes may represent specific actions or conditions that need to be performed or met in order to retrieve the desired information from database. Each node may correspond to a specific element or event and may serve as a step in the process of generating a final query. In an embodiment, each node may be associated with a separate query, wherein each node may result in a different request received from database. In one or more embodiments, processor 104 may generate search query to query database to retrieve relevant information in association with valve model datum 164. In one or more embodiments, processor 104 may be configured to identify at least one available valve model from a plurality of valve model 132 as a function of the query and/or search query. In one or more embodiments, each node in the query generation process may represent a logical step, such as condition evaluation, filter application, or table join, and may operate independently or in sequence. In one or more embodiments, nodes may serve to ensure that device selection is dynamically responsive to both anatomical requirements and operational constraints.

With continued reference to FIG. 1, processor 104 may generate a search query having multiple nodes to retrieve valve models 132 that are best matched to the anatomical and procedural requirements derived from valve model datum 164. In one or more embodiments, the search query generated by processor 104 may include annulus diameter data. For the purposes of this disclosure, "annulus diameter" refers to the measured or estimated internal diameter of the aortic valve annulus. In one or more embodiments, the aortic valve annulus is an anatomical ring of fibrous tissue that serves as the anchoring zone for repair or replacement devices. In one or more embodiments, an undersized prosthetic device 128 may result in paravalvular leak or valve migration, while an oversized device may risk annular rupture, conduction system interference (e.g., with the bundle of His), or coronary obstruction. In one or more embodiments, annulus diameter may be determined from cardiovascular characteristic datum. In one or more embodiments, the annulus diameter may range between approximately 1.8 cm and 2.5 cm for aortic valves, although individual patient anatomy may fall outside these values. In one or more embodiments, processor 104 may use the derived annulus diameter to refine the search query such that only valve models 132 (e.g., balloon-expandable valves, self-expanding frames, or supra-annular prostheses) that fall within the annular compatibility range are identified or returned. In one or more embodiments, processor 104 may retrieve a list of compatible valve models 132 along with relevant metadata, such as anchoring strategy (e.g., intra-annular vs supra-annular), radial force profile, and leaflet height. In one or more embodiments, annulus diameter may also be used to evaluate and select multi-component repair systems (e.g., valve+sealing skirt hybrids) by matching each component to its respective anatomical sub-region.

With continued reference to FIG. 1, in one or more embodiments, processor 104 may be configured to receive a 3D model representative of the aortic valve of a subject and a valve model 132 representative of a prosthetic device 128. In an embodiment, the 3D model of the aortic valve may be generated from patient-specific imaging data set of images derived from TEE ultrasound imaging device. In one or more embodiments, cardiac feature datum and/or cardiovascular characteristic datum may be derived from the 3D model and/or set of images and used to generate valve model datum 164 and/or receive or generate valve model 132. In one or more embodiments, processor 104 may be configured to simulate the interaction between the 3D model and the received valve model 132 representative of the prosthetic device 128. This simulation may include, without limitation, finite element analysis (FEA), anatomical fit testing, mechanical anchoring evaluation, dynamic flow modeling and/or the like. In an embodiment, the simulation may evaluate one or more pass datum values, including but not limited to spatial orientation, anchoring confidence, device expansion profile, coaptation zone coverage, and annular remodeling characteristics. In one or more embodiments, the 3D model and valve model 132 may be used for procedural simulation, patient eligibility screening, inventory matching, post-procedural assessment and/or any other processes associated with aortic valve intervention.

With continued reference to FIG. 1, processor 104 may be configured to generate a superimposed model 176 by superimposing valve model 132 onto 3D model 156. For the purposes of this disclosure, a "superimposed model" refers to a 3D representation wherein the valve model 132 is digitally overlaid and positioned within the 3D model. In one or more embodiments, the 3D model may be derived from patient-specific imaging data (e.g., 3D echocardiography, CT, or MRI), and may include anatomical landmarks such as the aortic annulus, the three aortic cusps (left coronary, right coronary, and non-coronary), and adjacent structures such as the left ventricular outflow tract, ascending aorta, and coronary ostia. In one or more embodiments, processor 104 may be configured to determine a superimposed position for the valve model 132 within the 3D model, wherein the superimposed position may define the anatomical location and orientation at which the valve model 132 may be digitally implanted. The superimposed position may be determined as a function of cardiac feature datum, which may include dimensions, spatial coordinates, and morphological characteristics of the aortic valve complex, including annular calcification, cusp asymmetry, or sinus of Valsalva dimensions. In an embodiment, processor may utilize a machine vision system or image registration techniques as described in this disclosure to correlate the valve model's geometry with anatomical targets within the 3D model. In one or more embodiments, the superimposed model 176 may be stored in a data store 124 and retrieved for simulation, clinical review, or training purposes.

With continued reference to FIG. 1, in one or more embodiments, processor 104 may be configured to determine an optimal path for placement of the valve model 132 within the 3D model 156. For the purposes of this disclosure, an "optimal path" refers to a calculated or user-defined route through the cardiovascular system that enables safe, accurate, and efficient delivery of the prosthetic aortic repair device to its intended implantation site. In the context of transcatheter aortic valve procedures, the optimal path may include, without limitation, a transfemoral trajectory via the femoral artery through the descending and ascending aorta to the aortic root. In one or more embodiments, the optimal path may be determined based on anatomical constraints, patient-specific vascular access data, device profile and flexibility, and cardiovascular characteristic datum, including spatial clearance, vessel diameter, curvature tolerances, and aortic arch angulation.

In one or more embodiments, processor 104 may implement graph-based pathfinding algorithms such as Dijkstra's algorithm or A* algorithm, wherein the 3D model 156 is represented as a spatial graph with nodes corresponding to anatomical waypoints and edges representing traversable paths. In an embodiment, processor may assign weights to edges based on anatomical constraints, minimizing tortuosity, contact with sensitive structures (e.g., chordae tendineae or atrial wall), or excessive curvature. In one or more embodiments, optimal path may be manually defined or refined by a user through a graphical interface. For example, a clinician may interact with a user interface to annotate the trajectory, adjust path curvature, or constrain entry angles to improve procedural feasibility. In one or more embodiments, processor may generate a path model 180 representative of optimal path and superimpose the path model 180 onto 3D model along with the valve model 132. This composite visualization may aid in virtual planning, intraoperative guidance, or training simulations. In one or more embodiments, superimposed model 176 may include the final virtual representation of the prosthetic device 128 along its delivery path and within its implantation site in the aortic anatomy. The superimposed model 176 may be used by processor for outcome prediction, device compatibility verification, or to support real-time physician decision-making during an aortic repair procedure.

With continued reference to FIG. 1, in one or more embodiments, processor 104 may determine an optimal path through the use of a machine-learning model configured to predict suitable transcatheter trajectories for aortic valve repair procedures. In one or more embodiments, processor may be configured to generate path training data representative of procedural experience, anatomical variation, and device-specific navigation behavior. For the purposes of this disclosure, "path training data" refers to any dataset used to train or refine machine-learning models responsible for predicting or optimizing catheter paths for device delivery to the aortic valve. In a non-limiting example, path training data may include historical data from prior successful aortic valve repair interventions, annotated with navigation trajectories, anatomical constraints, procedural outcomes, and delivery techniques. In another non-limiting example, path training data may include labeled correlations between exemplary 3D models, exemplary valve models 132, and their corresponding optimal access paths to the aortic valve region. In one or more embodiments, path training data may be received from data store 124, generated from user inputs (including clinician-labeled path examples), and/or the like. In one or more embodiments, users, such as medical professionals, may manually label specific trajectories within 3D models to serve as a ground truth for supervised learning. In one or more embodiments, path training data may be refined iteratively through a feedback loop as a function of updated anatomical imaging (e.g., CT or echocardiography), cardiac feature datum, and segmentations generated over time from different patients or procedures. This continual refinement process may be used to update or retrain a machine-learning model dynamically, allowing for increased accuracy and personalization of catheter navigation based on patient-specific anatomy and evolving device technologies.

With continued reference to FIG. 1, processor 104 may generate a path machine-learning model trained using path training data or updated path training data. In one or more embodiments, processor 104 may use the path machine-learning model to determine an optimal path within 3D model 156. In one or more embodiments, model training and data generation may occur simultaneously in real time, allowing for rapid iterations and updates based on intraoperative feedback or user correction. The machine-learning model may include, without limitation, convolutional neural networks (CNNs), recurrent neural networks (RNNs), graph neural networks (GNNs), transformer-based architectures adapted for spatial navigation tasks in anatomical environments, and/or the like.

With continued reference to FIG. 1, for the purposes of this disclosure, a "path model" refers to a computational representation of an optimal path to be traversed in order to reach the aortic valve. Path model 180 may provide both visual and numerical guidance for navigating a catheter-based delivery system from a vascular access point to the target site within the aortic valve anatomy. In one or more embodiments, generating path model 180 may include dividing the optimal path into a sequence of discrete path points. Each path point may correspond to clinically relevant locations, such as a start point, one or more intermediate points, and an end point. In one or more embodiments, a start point may include the femoral artery, commonly used in aortic interventions. In one or more embodiments, intermediate points may represent the delivery system's trajectory through the iliac artery and ascending aorta, approaching the aortic valve. In one or more embodiments, an end point may define the device deployment site adjacent to or within the aortic annulus, or in proximity to the aortic valve leaflets targeted for repair. Each path point may be annotated with 3D spatial coordinates (e.g., [x, y, z]) and orientation vectors that reflect the desired directionality of the catheter or device at that point. Processor 104 may interpolate between path points using mathematical techniques such as Bézier curves or cubic splines to generate a smooth trajectory adapted to patient-specific anatomy and device bending characteristics. In one or more embodiments, the resulting path model 180 may be superimposed onto 3D model 156, allowing clinicians to visualize the procedure. In one or more embodiments, path model 180 may be used intraoperatively as a navigational guide to support real-time delivery of prosthetic device 128. Additionally, path model 180 may be stored in a data store for procedural planning, comparative analysis, simulation training, or retrospective evaluation.

With continued reference to FIG. 1, processor 104 may be configured to identify a position of transducer within 3D model 156 and/or reference model 162. In one or more embodiments, the at least a processor may be configured to receive set of images 112 and receive, from a probe position predictor, a position 166 or predicted position of the probe and/or transducer. In one or more embodiments, processor 104 may obtain, from the at least a transducer, a new frame of the set of images, generate, using a segmentation model, a segmented image of the structure in a new frame, generate, using the at least a processor, a comparison of the segmented image from the new frame with a plurality of segmentations obtained from adjacent probe positions of the at least a 3D model, and estimate, using the probe position predictor, a change in position of the TEE probe 102 based on the comparison. As used in this disclosure, a "probe position predictor" is a model or algorithm configured to estimate the current or future position of a probe and/or transducer. In an embodiment, the probe position predictor may estimate the position of the probe based on previously acquired sets of images, probe movement patterns, real-time imaging feedback, and the like. As used in this disclosure, a "predicted position" is an estimated spatial location and orientation of the probe. In one or more embodiments, predicted position may include and/or be consistent with a position 166 of probe. In an embodiment, the predicted position may be generated by the probe position predictor, which may help in guiding the probe's movement and positioning during imaging or intervention. As used in this disclosure, a "new frame" is an image frame captured by the transducer at a time during the imaging process. In an embodiment, the new frame may provide updated information on the structures and the current position of the probe.

With continued reference to FIG. 1, identifying the position 166 of the at least a transducer further may include estimating spatial coordinates of the at least a transducer as a function of imaging plane orientation and probe articulation angles. As used in this disclosure, "spatial coordinates" are a set of numerical values that define the position of a point or object within a three-dimensional space. In an embodiment, the spatial coordinates may represent the precise location of the probe or anatomical structures relative to a defined reference frame, enabling accurate navigation and alignment during imaging and interventional procedures. As used in this disclosure, "imaging plane orientation" is the angular positioning and alignment of the ultrasound imaging plane relative to the structures being visualized. Without limitation, the imaging plane orientation may be defined by parameters such as tilt, rotation, or angulation, which determine how the ultrasound beam intersects with the target anatomy, thereby influencing image clarity and diagnostic accuracy. As used in this disclosure, "probe articulation angles" is the angular adjustments of the Probe. In an embodiment, the probe articulation angles may be controlled mechanically or electronically. In an embodiment, the probe articulation angles may direct the ultrasound beam in different directions within the body. Without limitation, the probe articulation angles may include anterior-posterior flexion, lateral bending, rotational movements, and the like, which allow clinicians to optimize imaging views and navigate around anatomical structure with greater precision.

With continued reference to FIG. 1, in an embodiment, identifying the position 166 of at least a transducer may include estimating the spatial coordinates of the at least a transducer based on the imaging plane orientation and the probe articulation angles. Without limitation, the spatial coordinates may define the location of the at least a transducer within a three-dimensional reference frame, allowing for more accurate tracking of its position relative to the anatomical structure being imaged. Continuing, by incorporating these spatial details, the apparatus may enhance visualization and improve procedural guidance during ultrasound imaging. The imaging plane orientation may influence this estimation by defining the directional alignment of the ultrasound beam relative to the target anatomy. Without limitation, adjustments in the imaging plane, such as tilting or rotating, may affect the way anatomical structure appear within the imaging field. Continuing, by continuously monitoring these changes, the apparatus may refine its estimate of the spatial coordinates of the at least a transducer, enabling more consistent and reliable imaging. Additionally, and/or alternatively, the probe articulation angles may provide further input for positioning by accounting for the physical movements of the Probe. Continuing, as the Probe is flexed, rotated, or adjusted to different angles, the transducer position may dynamically shift. Without limitation, by integrating articulation angle data with imaging plane orientation, the apparatus may generate a more precise representation of the spatial location of the at least a transducer. Continuing, this approach may improve real-time imaging guidance, assist with the Probe navigation, and optimize procedural accuracy during TEE imaging and interventional procedures.

Still referring to FIG. 1, processor 104 may be configured to identify, using the at least a processor, position 166 of the at least a transducer relative to the structure, relative to aortic valve and/or relative to 3D model. In one or more embodiments, identification may include identifying the position by performing a registration between the at least a 3D model 156 and the reference model 162 to identify a relative position of the at least a transducer relative to the structure and/or aortic valve. In one or more embodiments, identifying a position may include performing a registration between 3D model 156 and initial set of images to identify relative position. In one or more embodiments, identifying a position may include performing a registration between 3D model and subsequent set of images. In one or more embodiments, identifying a position may include identifying a position of transducer and/or delivery system. As used in this disclosure, a "position" is the spatial location and orientation of an object within a defined reference frame. In an embodiment, the object may include the at least a transducer. In an embodiment, the position may be expressed in terms of spatial coordinates, angles, or other metrics that define the precise placement of the transducer relative to anatomical structures during imaging or interventional procedures. As used in this disclosure, "registration" is the process of aligning two or more datasets to establish spatial correspondence between them. In an embodiment, the registration may include aligning the at least a 3D model and a reference model. In an embodiment, the registration may involve mathematical transformations, landmark-based matching, algorithmic adjustments, and the like, to ensure that real-time imaging data is accurately mapped onto a predefined anatomical framework.

With continued reference to FIG. 1, as used in this disclosure, a "relative position" is the spatial relationship between two objects determined by comparing their respective positions within a common coordinate system. In an embodiment, the two objects may include the at least a transducer and the structure. In an embodiment, the relative position may help in tracking probe movement, guiding adjustments, and ensuring precise alignment during imaging and procedural navigation. In an embodiment, identifying the position of the at least a transducer and/or the ultrasound imaging device may include performing registration between a pre-existing 3D model and a reference model 162 of the structure. For instance, without limitation, the apparatus may compare the real-time ultrasound image data, such as sets of images with a reference model 162 of the heart to determine the relative position of the at least a transducer. Continuing, this process may help ensure that the ultrasound beam is correctly aligned with the target structure, such as the aortic valve and thereby improving visualization and procedural accuracy. Without limitation, the registration process may involve feature-based alignment, where key anatomical landmarks, such as the aortic annulus or pulmonary veins, are matched between the real-time imaging data and the reference model. Continuing, once aligned, the apparatus may compute the relative position of the at least a transducer, allowing for more precise probe navigation. For example, without limitation, if the at least a transducer is detected to be positioned too laterally relative to the left atrium, the apparatus may provide guidance for adjusting its angulation or depth to optimize imaging.

With continued reference to FIG. 1, registering the at least a 3D model 156 and the reference model 162 may include performing an image-based transformation using feature-matching techniques to align the at least a 3D model 156 with the reference model. As used in this disclosure, an "image-based transformation" is a computational process that applies mathematical operations to modify an image dataset to align with another reference dataset. In an embodiment, the image-based transformation may include scaling, rotating, translating, and/or warping an image to achieve spatial correspondence between different imaging modalities, frames, models, and the like. In an embodiment, the image-based transformation may be used to adjust the at least a 3D model 156 so that it aligns accurately with the reference model, enabling more precise anatomical visualization and procedural navigation. As used in this disclosure, "feature-matching techniques" refer to a computational method used to identify and align corresponding features between two datasets. In an embodiment, the feature-matching techniques may include detecting anatomical landmarks, edges, textures, or specific shapes in both datasets and then computing the optimal transformation needed to align them. Without limitation, the feature-matching techniques may use methods such as intensity-based correlation, keypoint detection (e.g., SIFT, SURF), or deep-learning-based pattern recognition to establish spatial correspondence. For example, without limitation, the image-based transformation may involve rotating and scaling a real-time ultrasound image to match the orientation and size of a pre-existing 3D model of the heart, ensuring that both datasets are in a common reference frame. Continuing, the feature-matching technique such as landmark-based alignment may detect key anatomical features, such as the aortic valve annulus in both the 3D model and the reference model, allowing for precise overlay and comparison. In an embodiment, registering the at least a 3D model 156 with the reference model 162 may involve performing an image-based transformation that utilizes feature-matching techniques to align the two datasets. For instance, without limitation, during a TEE-guided intervention, the apparatus may extract structural landmarks from the real-time ultrasound images and compare them to a precomputed 3D model of the patient's heart, cardiac anatomy, structure and/or the like. Without limitation, by identifying matching features, such as the sinuses of Valsalva or the coronary ostia, the apparatus may apply a transformation that adjusts the at least a 3D model 156 to fit the real-time imaging data. In an embodiment, the registration process may enhance probe navigation and procedural accuracy by ensuring that clinicians have a well-aligned representation of the anatomical structure. If feature-matching techniques detect a discrepancy in alignment, additional transformations, such as non-rigid deformations, may be applied to refine the overlay. Without limitation, this capability may improve visualization during complex interventions, such as aortic valve repair or transcatheter valve replacement, where precise spatial alignment is critical for procedural success.

With continued reference to FIG. 1, processor 104 may be configured to identify the position 166 of the transducer relative to the aortic valve by receiving, from a probe position predictor, a predicted position of the transducer. In one or more embodiments, processor may use sets of images to identify a predicted position and/or current position of transducer and/or probe. In one or more embodiments, processor may be configured to use an initial set of images to identify predicted position. An "initial set of images" for the purposes of this disclosure refers to a first set of images received by processor 104 in instances in which processor 104 receives more than one sets of images during an iteration of the processing of apparatus. In one or more embodiments, initial set of images may be consistent with set of images 112 as described in this disclosure. In one or more embodiments, set of images 112 may be referred to as 'initial set of images' to delineate between a second or subsequent set of images received by processor 104. In one or more embodiments, processor 104 may be configured to receive subsequent set of images. A "subsequent set of images" for the purposes of this disclosure refers to set of images that have been received by processor following receipt of an initial set of images. In one or more embodiments, processor 104 may be configured to receive subsequent set of images to determine changes in position of transducer. In one or more embodiments, processor 104 may be configured to obtain subsequent set of images similarly to that of initial set of images. In one or more embodiments, processor 104 may be configured to iteratively and/o continuously receive subsequent set of images in order to identify changes in position of transducer and/or probe. In one or more embodiments, set of images 112, initial set of images and/or subsequent set of images may include a real-time feed of image data being iteratively received from the transducer and/or TEE probe 102. In one or more embodiments, image data includes images received from ultrasound imaging device. A "real-time feed" for the purposes of this disclosure refers to a continuous transmission of data. In one or more embodiments, real time feed may include a continuous transmission of set of images from ultrasound imaging device to processor 104. In one or more embodiments, set of images may be iteratively and/or continuously received by processor 104, wherein set of images may differ based on changes in transducer location between an initial set of data received and a subsequent set of data received after movement of transducer. In one or more embodiments, processor 104 may be configured to iteratively and/or continuously receive set of images and identify probe positions, make new determinations, generate outputs and/or the like based on changes within set of images. In one or more embodiments, processor may be configured to compare the initial set of images to the subsequent set of images estimate, using the probe position predictor, a change in position of the transducer based on the comparison. In one or more embodiments, processor may receive initial set of images, identify the position of the transducer and receive subsequent set of images and identify a new location of the transducer based on changes in the sets of data. In one or more embodiments, processor 104 may identify changes in position by identifying new positions of transducer using subsequent set of images. In one or more embodiments, processor 104 may be configured to identify position of transducer relative to the aortic valve by iteratively and/or continuously determining the position of transducer and updating and/or changing positions based on subsequently received information.

With continued reference to FIG. 1, processor 104 is further configured to identify the position of delivery system 106 within the heart and/or 3D model 156. In one or more embodiments, processor is configured to identify the position of delivery system as a function of at least one image of the initial set of images. In one or more embodiments, processor 104 may determine the position of delivery system 106 using ultrasound imaging device and/or transducer. In one or more embodiments, the transducer may capture ultrasound data in the form of initial set of images and/or a subsequent set of images. Within at least one image of the initial set of images 112, delivery system 106 may appear as a bright object on a grayscale ultrasound image, attributed to acoustic impedance mismatch between the material of delivery system 106 and surrounding cardiac tissue. In one or more embodiments, the transducer may be oriented and/or manipulated in real time to acquire cross-sectional views of a target anatomical region, such as the aortic annulus. Delivery system 106 may be visually identified based on its reflective appearance, dynamic motion, and spatial relationship to anatomical landmarks. In one or more embodiments, a medical professional and/or system operator may simultaneously manipulate both delivery system 106 and the transducer to confirm dynamic spatial alignment, using techniques such as rotational sweeping or sector scanning to observe catheter trajectory and movement in real time. In one or more embodiments, processor 104 may execute one or more image-processing algorithms, including machine vision systems and/or trained image classifiers, to perform catheter localization within the ultrasound dataset. In a non-limiting example, edge detection and shape recognition filters (e.g., Sobel, Canny) may be applied to ultrasound images to detect bright gradients consistent with the linear or cylindrical profile of delivery system 106. These detected features may then be matched to predefined catheter geometries retrieved from local memory or data store 124 using a template matching process. Template matching may involve comparing captured image segments with stored catheter geometry models under varying orientations and imaging depths.

With continued reference to FIG. 1, in one or more embodiments, processor 104 may further determine the position of delivery system 106 by acquiring multiple image slices (where each image slice may refer to a single image within sets of images) from ultrasound imaging device. Processor 104 may generate 3D model 156 as a function of the images and/or slices, including a three-dimensional representation of cardiac anatomy. In one or more embodiments, automated segmentation algorithms may isolate and track delivery system 106 within the 3D model. In one or more embodiments, algorithms may detect and label portions of the delivery system, such as the tip and shaft, relative to segmented anatomical landmarks including the left ventricle, aortic root, and aortic annulus. This identification may leverage volume rendering, anatomical segmentation, and motion-based or appearance-based tracking techniques to localize delivery system 106. In one or more embodiments, the initial set of images may be spatially registered using known transducer positions and orientations. This registration may enable reconstruction of a 3D data structure that models both the patient-specific cardiac anatomy and the catheter's position therein. Within the 3D model, delivery system 106 may be recognized as a high-intensity, elongated object with distinct reflectivity and geometry, contrasting with surrounding cardiac tissue. In one or more embodiments, this information may be used to facilitate accurate positioning of a prosthetic device 128 for aortic valve repair, ensuring alignment with the aortic annulus and surrounding anatomical features.

With continued reference to FIG. 1, in one or more embodiments, machine vision systems, machine learning models, and/or CNNs as described in this disclosure may be trained to recognize the geometry, texture, and reflectivity patterns of delivery system 106 and prosthetic device 128 within set of images. These systems may use shape-based filters as described in this disclosure and intensity thresholding to isolate hyperechoic regions, excluding non-catheter structures based on non-linear or non-tubular morphology. In one or more embodiments, motion tracking algorithms may be employed to differentiate static cardiac structures from the dynamically manipulated delivery system 106. In one or more embodiments, when the delivery system is actively adjusted during the procedure, processor 104 may track its movement frame-by-frame or image-by-image across the 3D model, generating a temporal-spatial trajectory of its path. In one or more embodiments, delivery system 106 may be superimposed within the 3D model 156. This superimposition provides spatial context for its position relative to critical anatomical landmarks such as the aortic valve annulus, left ventricular outflow tract, ascending aorta, and left ventricle. In one or more embodiments, apparatus 100 may include a user interface that allows for real-time reorientation of 3D model, enabling users to rotate, zoom, and slice through the volume to confirm precise catheter tip positioning and trajectory for accurate aortic valve device delivery. In one or more embodiments, position identification of delivery system 106 may be coordinated with identification of transducer position, as previously described. Processor 104 may identify catheter position as a function of image data and/or set of images that includes views of both delivery system 106 and transducer.

Still referring to FIG. 1, in one or more embodiments, position 166 of transducer and/or delivery system 106 may be determined based on an identification of anatomical landmarks within a plurality of images, such as sets of images. An "anatomical landmark" as described in this disclosure refers to a distinct, identifiable structure or feature within a biological anatomy that may serve as a spatial reference point within the body. Anatomical landmarks may be defined by consistent morphological, positional, or functional characteristics. In one or more embodiments, anatomical landmarks may include, but are not limited to, organs, vessels, bones, tissue junctions, or other physiologically relevant structures that can be visually recognized within set of images or ultrasound images as described above. In one or more embodiments, anatomical landmarks may be used to guide procedural planning, image registration, segmentation, positioning of medical devices and/or the like by providing fixed or relatively invariant reference positions within a given anatomical context, such as the aortic valve. In one or more embodiments, one or more medical images, such as echocardiographic frames (e.g., TEE) may be received and processed by processor 104 to extract anatomical features or structures relevant to cardiac orientation. Such anatomical landmarks may include, without limitation, the aortic valve, aortic root, sino-tubular junction, left ventricular outflow tract, coronary ostia, and/or the like. In one or more embodiments, a machine vision system and/or any other system as described in this disclosure may be configured to identify anatomical landmarks within set of images. In one or more embodiments, image processing algorithms such as, without limitation, edge detection, segmentation, contour extraction, and/or template matching may be applied to identify landmark positions in two-dimensional images. In one or more embodiments, a relative spatial relationship or distance between the identified TEE probe 102 (or tip thereof) and one or more anatomical landmarks may be calculated. In an embodiment, processor 104 may utilize triangulation techniques and/or spatial registration algorithms to determine the relative coordinates of the probe tip or the catheter-based delivery system within the cardiac anatomy. Additionally, or alternatively, depth or angle estimations may be derived based on echo signal characteristics and geometry of the probe in reference to known anatomical planes. In one or more embodiments, processor may then be configured to identify anatomical landmarks within set of images.

Still referring to FIG. 1, in one or more embodiments, the identified positions of anatomical landmarks and the corresponding relative position of the TEE probe 102 and/or delivery system may be mapped onto a three-dimensional model (i.e. 3D model 156) of the patient-specific heart anatomy. In one or more embodiments, processor 104 may align or register the detected anatomical landmarks from the image data or set of images with corresponding features in the 3D model using rigid or non-rigid transformation algorithms such as, without limitation, Iterative Closest Point (ICP), B-spline registration, or affine transformation. In one or more embodiments, the relative distance or vector computed between the probe and the anatomical landmarks in 2D image space may be converted into 3D spatial coordinates through calibration matrices and geometric transformations. The 3D positioning of the probe and/or delivery system 106 may then be dynamically updated within the rendered 3D model, enabling visualization of its orientation and proximity to critical cardiac structures. Such visualization may aid in procedural guidance, anatomical orientation, and verification of access route (e.g., for transseptal puncture or device deployment). In one or more embodiments, position determination may further be enhanced by machine learning algorithms trained on annotated datasets containing image landmarks and associated probe/device positions. In a non-limiting example, a convolutional neural network (CNN) may be configured to automatically infer probe position from echocardiographic image sequences. Additionally, recurrent neural networks (RNNs), such as long short-term memory (LSTM) networks, may be utilized to analyze sequential image data to predict motion trajectory or orientation of the probe over time. In one or more embodiments, processor may identify position of TEE probe 102 and/or delivery system relative to anatomical landmarks as a result. In one or more embodiments, processor may further identify position of TEE prove and/or delivery system relative to 3D model, wherein 3D model and positions of TEE probe 102 and/or delivery system may be visually presented to a medical professional. In one or more embodiments, processor 104 may be configured to continuously and/or iteratively track and update the 3D position of the TEE probe 102 and/or delivery system based on new incoming image data (e.g. subsequent set of images and/or real-time feed as described herein), thereby enabling real-time or near real-time tracking during an interventional procedure. Additionally, user interface 172 of display device 168 may be configured to overlay the tracked position of the probe or device within the 3D model or corresponding imaging plane, facilitating spatial orientation and navigation for the operator.

With continued reference to FIG. 1, processor 104 may be configured identify the position of delivery system 106 within 3D model 156 and/or reference model 162, in a similar manner to the identification of the position of the transducer as described in this disclosure. In one or more embodiments, the processor 104 may obtain real-time images of delivery system within set of images and use a catheter position predictor to estimate its current or predicted position within the 3D model or reference model. The catheter position predictor may function similarly, and/or be consistent with, probe position predictor, by utilizing previously acquired sets of images, catheter movement patterns, and real-time imaging feedback to estimate the spatial coordinates of the delivery system 106. In one or more embodiments, processor may use segmentation techniques, similar to those used for transducer, to generate a segmented image of the catheter's current location in the latest frame of real-time imaging within sets of images. This segmented image can be compared to a set of previous segmentations, allowing the processor to estimate the change in position of the delivery system 106 based on the comparison, and adjust the model accordingly. In an embodiment, the delivery system 106 may also be identified through a registration process (as described above), where processor performs an alignment between 3D model and reference model similar to that of transducer. This enables the identification of the delivery system's position relative to the aortic valve and anatomical structures during the intervention. In one or more embodiments, processor may continually refine the estimated position of the delivery system as new frames of image data are received, and adjust its predicted position based on real-time updates. In one or more embodiments, delivery system's position may be expressed in terms of spatial coordinates, such as angles and distances, similar to how the transducer position is expressed relative to the 3D model. In one or more embodiments, processor may calculate delivery system's precise location and orientation based on this information, thus providing spatial feedback for real-time guidance during the aortic valve repair.

With continued reference to FIG. 1, processor 104 may be configured to identify a position of delivery system 106 relative to 3D model 156, as well as an orientation and location of prosthetic device 128 relative to the 3D model. In one or more embodiments, processor 104 may dynamically adjust the position of valve model 132 relative to changes associated with delivery system 106, such that valve model 132 may accurately portray the location and/or orientation of prosthetic device 128. In one or more embodiments, once processor 104 identifies the position of delivery system 106, processor may adjust the placement of valve model 132 by determining a relative position between valve model 132 and the delivery system within the 3D model. In one or more embodiments, the movement of valve model 132 relative to the delivery system may be guided by the catheter's trajectory, the anatomical constraints of the patient's heart, the planned path for the prosthetic device 128 delivery, and/or the like. As a non-limiting example, processor 104 may adjust valve model 132 along the optimal path determined previously, ensuring precise alignment with the aortic valve annulus. In one or more embodiments, processor 104 may utilize the same pathfinding and machine learning algorithms described above to adjust the valve in response to data received in real time. For example, as the delivery system moves through cardiac chambers, valve model 132 may move within the 3D model 156 accordingly. In one or more embodiments, processor 104 may be configured to provide visual feedback to the user through a display by showing the movement of valve model 132 relative to delivery system 106 as the catheter progresses through the patient's heart. In one or more embodiments, the processor may iteratively receive a real-time feed in the form of sets of images to continuously refine the relative position and orientation of the valve model 132 and delivery system 106.

With continued reference to FIG. 1, processor is configured to display the position of delivery system 106 relative to 3D model 156 using at least valve model 132. In one or more embodiments, the processor may display the position of the delivery system by superimposing valve model 132 onto the 3D model and orienting valve model 132 relative to changes in movement of the delivery system and/or prosthetic device 128 as described above. In one or more embodiments, the position of the delivery system may be visualized through changes in the location of valve model 132 relative to the 3D model. In one or more embodiments, processor 104 may be configured to display the position of delivery system 106 relative to 3D model 156, where the display includes a path model 180 for the implantation of prosthetic device 128 within the heart of the subject. In one or more embodiments, the processor may use previously determined position data for the delivery system 106 and/or predicted trajectory data to generate a visual path model 180. This path model 180 may represent the proposed or actual route of the delivery system as it is navigated through the subject's anatomy toward the target location for prosthetic valve implantation, such as within the ascending aorta or aortic valve annulus. In one or more embodiments, path model 180 may be displayed by the processor and may be overlaid onto the 3D model 156 of the heart, enabling real-time guidance and navigation. In one or more embodiments, path model 180 may take into account key anatomical landmarks, vessel pathways, and potential obstacles in the heart to help optimize the deployment of prosthetic device 128. In an embodiment, a display may dynamically adjust path model 180 as delivery system 106 progresses through the heart, updating the visual representation based on real-time imaging feedback and the current position of the catheter.

With continued reference to FIG. 1, the at least a processor 104 may be further configured to display, using a graphical user interface (e.g., User interface 172) of a downstream device, such as a user device 168 the position of the at least a transducer, and overlay, on the at least a 3D model 156, a visual indication of a probe trajectory of the at least a transducer. A "graphical user interface," as used herein, is a graphical form of user interface that allows users to interact with electronic devices. A graphical user interface may include, be included in, and/or be consistent with any user interface 172 as described in this disclosure. In one or more embodiments, GUI may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

With continued reference to FIG. 1, in an embodiment, the graphical user interface and an event handler may operate together to enable seamless interaction between the user and the apparatus 100. The GUI serves as a visual and interactive layer through which the user engages with the apparatus 100, presenting elements such as buttons, sliders, input fields, and informational displays. The event handler, on the other hand, functions as the underlying mechanism that monitors and responds to user interactions with the GUI. For example, when a user clicks a button on the GUI to request an explanation of a concept, the event handler may detect the click event, identify its context, and trigger the appropriate processes within the apparatus 100 to generate a tailored response. This interplay may ensure dynamic and responsive system behavior, as the event handler processes various input events such as clicks, taps, keystrokes, or voice commands, and relays these inputs to the relevant system components. The GUI subsequently updates to reflect the system's responses, such as displaying output, modifying visual elements, or providing real-time feedback. Together, the GUI and event handler create an intuitive and interactive experience, bridging user actions and system functionality to achieve efficient and personalized outcomes.

With continued reference to FIG. 1, an "event handler," as used in this disclosure, is a module, data structure, function, and/or routine that performs an action in response to an event. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to a user in response to such requirements.

With continued reference to FIG. 1, as used in this disclosure, a "visual element" is a component or feature within a system, display, or interface that conveys information through visual means. In a non-limiting example, the visual element may include text, images, icons, shapes, colors, and/or other graphical components designed to be perceived by the user. In a non-limiting example, the visual element may aid in communication, navigation, and/or interaction with the system. Without limitation, the visual element may be used to enhance user experience, guide behavior, and/or represent data visually in an intuitive or informative way. A visual element may include data transmitted to display device, client device, and/or graphical user interface. In one or more embodiments, visual element may be interacted with. For example, visual element may include an interface, such as a button or menu. In one or more embodiments, visual element may be interacted with using a user device such as a smartphone, tablet, smartwatch, or computer.

With continued reference to FIG. 1, in an embodiment, the apparatus 100 and/or the downstream device may include a data structure. In one or more embodiments, downstream device may include user device 168. as used in this disclosure, "data structure" is a way of organizing data represented in a specialized format on a computer configured such that the information can be effectively presented in a graphical user interface. In one or more embodiments, the data structure includes any input data. In one or more embodiments, the data structure contains data and/or rules used to visualize the graphical elements within a graphical user interface. In one or more embodiments, the data structure may include any data described in this disclosure. In one or more embodiments, the data structure may be configured to modify the graphical user interface, wherein data within the data structure may be represented visually by the graphical user interface. In one or more embodiments, the data structure may be continuously modified and/or updated by processor 104, wherein elements within graphical user interface may be modified as a result. In one or more embodiments, the data structure may include 3D model, reference 3D model, initial 3D model, probe estimation and/or any information received and/or generated by processor 104. In one or more embodiments, processor 104 may be configured to transmit display device and or the downstream device. Transmitting may include, nd without limitation, transmitting using a wired or wireless connection, direct, or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio, and microwave data and/or signals, combinations thereof, and the like, among others. Processor 104 may transmit the data described above to a database wherein the data may be accessed from the database. Processor 104 may further transmit the data above to a display device, client device, or another computing device. The data structure may serve as the organizational framework that stores, retrieves, and manages data required for processing events and updating the GUI. The data structure may act as a bridge between the user's input, captured by the event handler, and the output displayed on the GUI, ensuring that information is handled efficiently and accurately throughout the interaction. For example, without limitation, when a user interacts with a dropdown menu in the GUI to select a topic, the event handler may capture this input and accesses a data structure, such as a dictionary or tree, which maps each topic to its associated resources or actions. The data structure may retrieve the relevant information such as text explanations, videos, or interactive exercises, and passes it back to the event handler, which may then trigger the appropriate updates to the GUI, such as displaying the selected topic's content. In another embodiment, the data structure may also maintain the state of the system, tracking user progress, preferences, and session history. For instance, without limitation, a hash table may store user specific configurations, such as preferred learning styles or recent activity, which the event handler references when processing interactions. The GUI may then dynamically adapt to display content aligned with these configurations. This integration may ensure that user inputs are seamlessly translated into meaningful system outputs, with the data structure enabling rapid access, consistency, and scalability throughout the process. As used in this disclosure, a "hash table" is a data structure that stores data in a way that allows for fast retrieval, insertion, and deletion of elements. The hash table may organize data into key-value pairs, where each key is unique and used to identify its corresponding value. A hash table may use a hash function to compute an index, or hash code, from the key, which determines where the key-value pair is stored within an array or list.

With continued reference to FIG. 1, as used in this disclosure, an "interactive element" is a component or feature within a graphical user interface (GUI) that allows users to perform actions, provide input, or engage with the apparatus 100. Interactive elements may be designed to facilitate two-way communication between the user and the system, enabling the user to influence the behavior of the apparatus or obtain feedback in response to their actions. Examples of interactive elements may include buttons, dropdown menus, sliders, checkboxes, input fields, and hyperlinks. More advanced interactive elements may include drag-and-drop interfaces, interactive diagrams, or dynamically updating content areas that respond to user actions in real time. The interactive elements may enhance user engagement by providing intuitive and responsive mechanisms for interacting with the system. Interactive elements may operate by responding to user actions such as clicks, taps, swipes, or keyboard inputs, and triggering predefined system behaviors or processes. The execution of the interactive elements may require a combination of front-end and back-end technologies that work together to provide seamless functionality and user interaction. On the front end, technologies such as HTML and CSS may define the structure, appearance, and layout of the interactive elements, while JavaScript may enable dynamic functionality. For example, without limitation, JavaScript may detect when the user clicks a button and trigger actions or animations. Front-end frameworks like React, Angular, or Vue.js may further enhance development by offering reusable components and efficient rendering mechanisms. On the back end, the system may process the user's input, retrieve the necessary data, and communicate with the front end to provide an appropriate response. APIs may act as a bridge between the front end and back end, facilitating data transfer, such as sending a user's form submission to the server and retrieving processed results. Server-side logic implemented using languages like Python, Java, or Node.js, may handle input processing and return relevant data, such as a user's profile or quiz questions. Additional supporting technologies may ensure the smooth operation of interactive elements. Event listeners, for instance, may continuously monitor for specific actions like mouse clicks or text entries, executing code when such events are detected. Efficient data structures, such as hash tables or dictionaries, may store interactive state data, such as user preferences or settings, for quick access and updates. Databases, including MySQL or MongoDB, may manage and store the data required for interactive features, such as user profiles or historical activity. Communication technologies may also help maintain the responsiveness of interactive elements. AJAX (Asynchronous JavaScript and XML) may allow the front end to update portions of a web page without requiring a full page reload, enhancing responsiveness. WebSockets may provide real-time interaction capabilities, such as live chats or collaborative tools, by enabling persistent communication between the client and the server. Without limitation, the apparatus 100 may include one or more APIs. As used in this disclosure, an "application programming interface (API)" is a set of defined protocols, tools, and methods that allow different software applications, systems, or components to communicate and interact with each other. An API may act as an intermediary that enables a client application, such as a user-facing app, to send requests to a server or service and receive the necessary responses, facilitating seamless integration and functionality across diverse systems.

With continued reference to FIG. 1, as used in this disclosure, a "visual indication" refers to a visual representation. As used in this disclosure, a "probe trajectory" refers to the path or predicted movement of a probe within a defined spatial reference frame. In an embodiment, a visual indication of a probe trajectory may be displayed on an imaging interface, allowing clinicians to track the current, past, or anticipated position of the probe relative to anatomical structures. The visual indication may include elements such as lines, arrows, color-coded overlays, or dynamic markers that assist in guiding the probe during navigation and positioning. In one or more embodiments, the probe trajectory may include the trajectory of a transducer and/or delivery system 106. In an embodiment, the visual indication of a probe trajectory may appear as a dynamic overlay on an imaging display, providing real-time feedback on the movement and positioning of the probe and/or transducer relative to cardiac structures. In one or more embodiments, the visual indication of the probe trajectory may include a color-coded path showing the current and previous positions of the probe, with a projected trajectory represented by a dashed or highlighted line extending toward the aortic valve. The display may also incorporate directional arrows or gradient shading to indicate the intended or recommended movement of the probe based on real-time tracking and predictive algorithms. Additionally, and/or alternatively, the visual indication of a probe trajectory may be presented as a semi-transparent overlay that adjusts dynamically as the probe moves, allowing clinicians to anticipate its placement and orientation during aortic valve repair procedures. In some implementations, the visual indication of a probe trajectory may be displayed with adjustable markers indicating key anatomical landmarks, such as the aortic valve annulus or sinotubular junction, helping guide the probe to an optimal imaging position. The graphical user interface (GUI) may also include numerical data or annotations showing the probe articulation angles, depth, and relative position within the imaging plane.

With continued reference to FIG. 1, apparatus 100 may further include a display device 168. As used in this disclosure, a "display device" is an electronic device that visually presents information to a user. In one or more embodiments, display device may be consistent with downstream device as described in this disclosure. In an embodiment, display device may include an output interface that translates data such as, without limitation, subsequent 3D model from processor 104 or other computing devices into a visual form that can be easily understood by user. In one or more embodiments, subsequent 3D model/or other data described herein such as, without limitation, ultrasonic images, 3D VOR, shape parameters initial model and/or template model may also be displayed through display device 168 using a user interface 172. User interface 172 may include a graphical user interface (GUI), wherein the GUI may include a window in which subsequent 3D model and/or other data described herein may be displayed. In an embodiment, user interface 172 may include one or more graphical locator and/or cursor facilities allowing user to interact with subsequent 3D model and/or any other data, or even process described herein; for instance, and without limitation, by using a touchscreen, touchpad, mouse, keyboard, and/or other manual data entry device, user may enter user input containing selecting specific regions, adding comments, adjusting parameter, and/or the like. In a non-limiting example, user interface 172 may include one or more menus and/or panels permitting selection of measurements, models, visualization of data/model to be displayed and/or used, elements of data, functions, or other aspects of data/model to be edited, added, and/or manipulated, options for importation of and/or linking to application programmer interfaces (APIs), exterior services, data source, machine-learning models, and/or algorithms, or the like. Persons skilled in the art, upon reviewing the entirety of this disclosure, will be aware of various ways in which a visual interface and/or elements thereof may be implemented and/or used as described in this disclosure.

Still referring to FIG. 1, in one or more embodiments, an apparatus and/or method described herein may enable ultrasonic imaging to replace or serve as an alternative to MRI and/or CT scans for aortic valve assessment. This approach may reduce radiation exposure to subjects and offer a safer imaging option, especially for patients with implants.

Figure 2B:
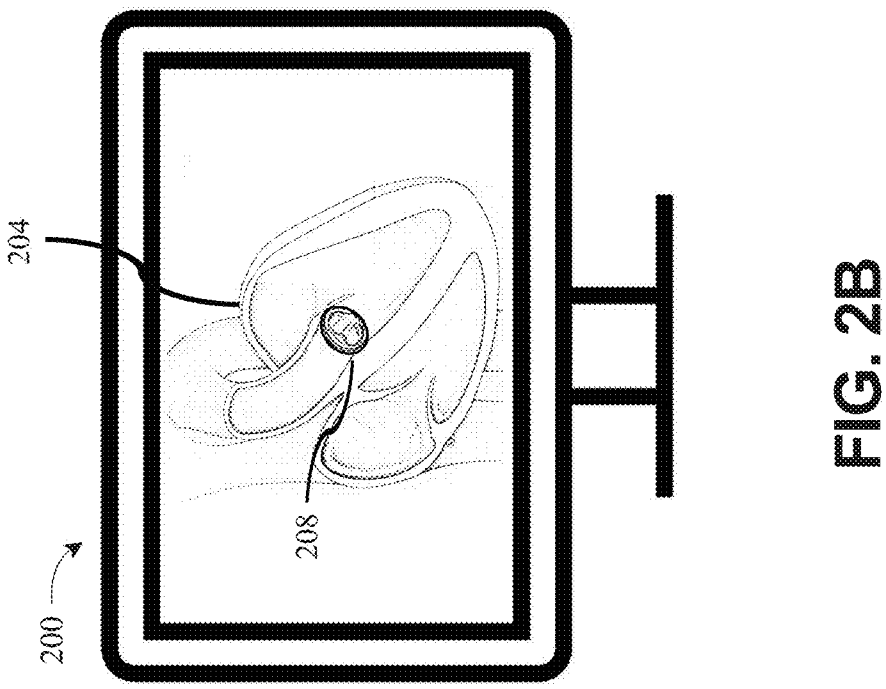
FIGS. 2A-2B are exemplary embodiments of a user interface.
Figure 2A:
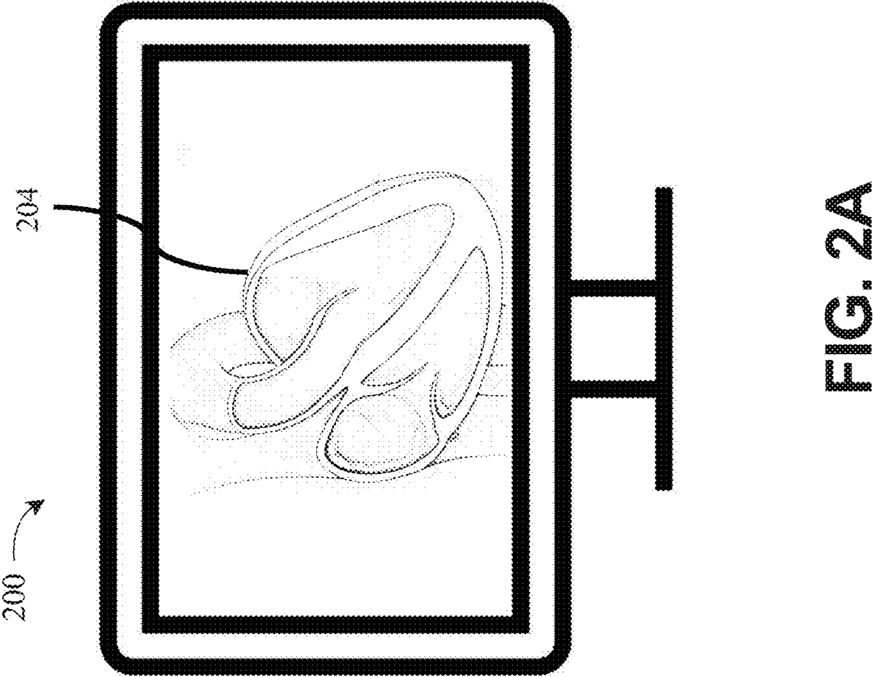

Referring now to FIGS. 2A-B, an exemplary embodiment of a user interface 200 is described. In one or more embodiments, user interface 200 may include any interface as described in this disclosure. The interface may be configured to display data created in this disclosure, such as, but not limited to, a 3D representation of the aortic valve, a 3D heart model, valve models, anatomical maps, and/or related visualizations.

Referring specifically to FIG. 2A, user interface 200 may include 3D model 204. In one or more embodiments, 3D model 204 may include a patient-specific heart model including the aortic valve. This 3D representation may be rendered on a display operatively coupled to a processor and incorporate anatomical features derived from a set of images and/or ultrasound data. The 3D model 204 may accurately depict cardiac structures such as the left ventricle, ascending aorta, aortic valve leaflets, aortic annulus, and surrounding tissues. In one or more embodiments, 3D model 204 may represent a patient's heart, serving as a map or reference during aortic valve interventions. The model may be generated by the processor using a combination of generic cardiac feature data and patient-specific imaging, including identification of anomalies or variations. Ultrasound images may be analyzed to extract cardiac characteristic data and compared against a generic 3D heart model. Spatial deviations, tissue density changes, or morphological irregularities may be identified and used to personalize the 3D model. Features not directly identified may retain default values from the generic template.

Referring to FIGS. 2A-2B, user interface 200 may support interactive manipulation of 3D model 204, such as rotation, zooming, and sectional views. In one or more embodiments, the interface may highlight or annotate key anatomical features of the aortic valve, including leaflet curvature, annular dimensions, and coaptation geometry. Measurements such as annular diameter or leaflet length may be overlaid on the model to aid in pre-operative planning.

Referring specifically to FIG. 2B, user interface 200 may display a 3D model with valve model 208 overlaid or superimposed onto 3D model 204. Valve model 208 may represent a prosthetic aortic valve intended for implantation at or near the native aortic valve. The prosthetic valve may be virtually positioned within the annular space or valve region of 3D model 204 in a proposed orientation and depth. Medical professionals may use valve model 208 to visualize device placement. In one or more embodiments, the user interface 200 may guide clinicians during aortic valve surgery or transcatheter aortic valve replacement (TAVR) procedures. The interface may enable visualization of the spatial relationship between the prosthetic valve and anatomical structures including the aortic annulus, left ventricular outflow tract, and adjacent cardiac tissues. This visualization can assist clinicians in assessing device fit, orientation, and potential complications such as interference with coronary ostia or paravalvular leaks. The combined 3D model and valve model may be used for planning and guiding aortic valve interventions. User interface 200 may also support simulating device deployment, adjusting implant trajectories, and reviewing multiple valve model options. In one or more embodiments, valve model 208 may be selected from a plurality of stored valve models matched based on anatomical fit and clinical parameters derived as described in reference to FIG. 1.

Figure 3:
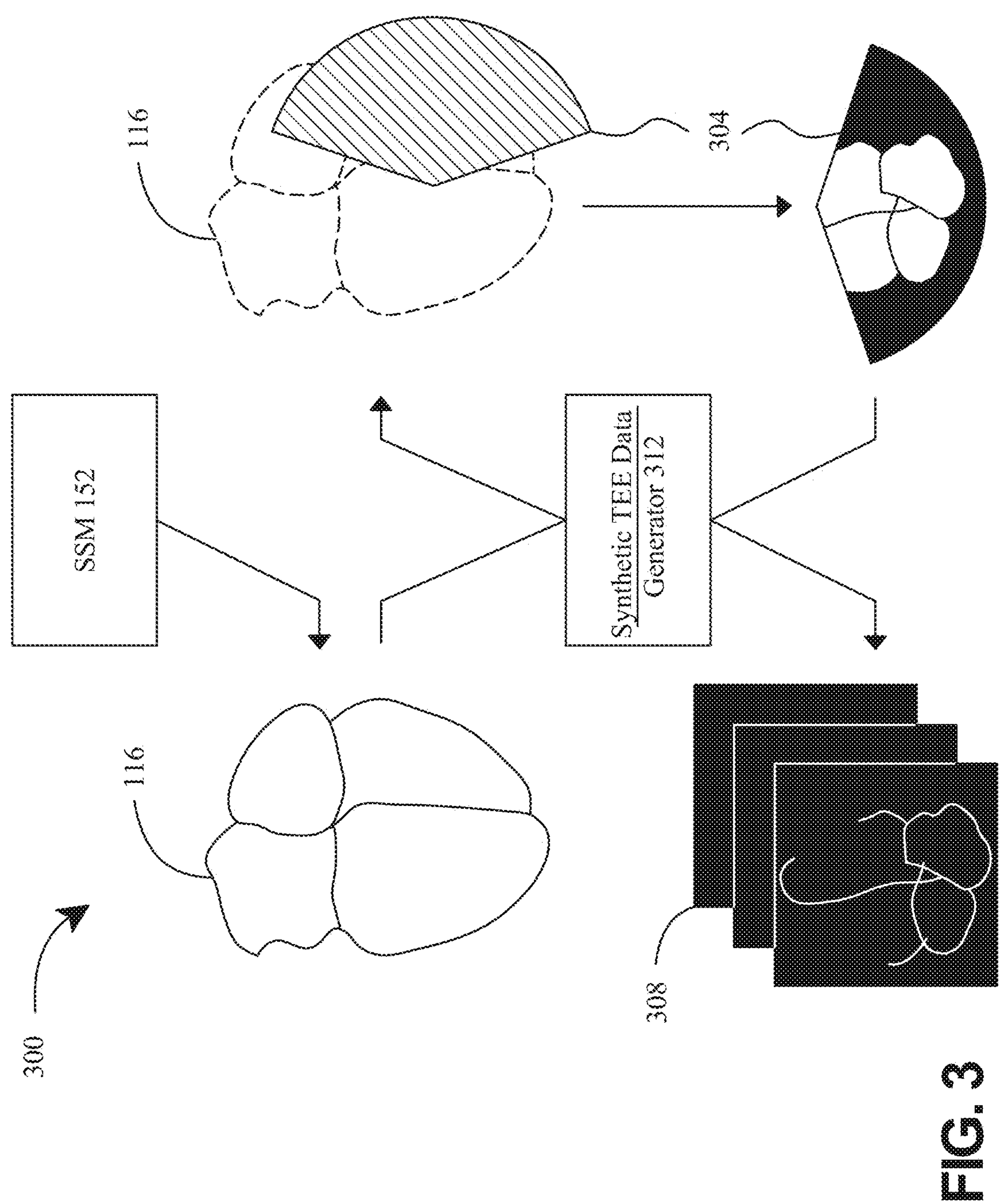
FIG. 3 is a flow diagram of an exemplary embodiment of an exemplary TEE image generation process.

Now referring to FIG. 3, a flow diagram of an exemplary embodiment of an ultrasonic image generation process 300 using TEE (transesophageal echocardiography) is described. In an embodiment, structure training data may be generated, at least in part using a TEE image generation process. In one or more embodiments, processor 104 may be configured to receive a 3D model of the heart, such as any 3D model of structure as described herein, and identify a TEE view 304 (i.e., a visual representation of an image obtained using transesophageal echocardiography). In one or more embodiments, the 3D model received by processor 104 may be derived from CT scans as described above with reference to FIG. 1. In one or more embodiments, processor 104 may receive CT scans directly in lieu of 3D models. A synthetic TEE frame 308 may then be generated by processor 104 as a function of the identified TEE view 304, wherein the synthetic TEE frame 308 may be used as one of the training examples in the structure training data.

With continued reference to FIG. 3, in one or more embodiments, processor 104 may interface with one or more 3D models (i.e., detailed representations of the heart's anatomy in a 3D space, capturing intricate structures, chambers, vessels, valves, and more) or other imaging modalities and/or databases. Processor 104 may be equipped with algorithms such as convolutional neural networks (CNN), gradient boosting machines, support vector machines (SVM), principal component analysis (PCA), and/or the like to analyze the geometry and spatial relationships within the 3D models. In one or more embodiments, 3D models may be received from SSM 152 as described above with reference to FIG. 1, using a communicative connection between processor 104 and SSM 152. In a non-limiting example, processor 104 may be configured to determine optimal viewpoints or angles from which TEE view 304 would provide the desired diagnostic value or procedural guidance.

Still referring to FIG. 3, in one or more embodiments, identification and selection of TEE view 304 may be performed automatically using one or more machine learning models as described herein. In a non-limiting example, processor 104 may utilize one or more machine learning models trained on cardiac anatomy viewpoint identification training data, wherein the training data includes a plurality of cardiac anatomies as input correlated with a plurality of TEE images as output. The trained machine learning models may then be used to identify at least one TEE view 304 (i.e., the most informative view) for a given cardiac anatomy.

Still referring to FIG. 3, in other cases, TEE view 304 may be defined by a user such as a medical professional. In a non-limiting example, user interface 172 of display device 168 may allow a user (e.g., a clinician) to manually rotate, pan, and zoom a displayed 3D model and/or corresponding CT scans. As the user does so, processor 104 may dynamically calculate and display potential TEE views 304 based on the user's chosen perspective. Additionally, or alternatively, depending on the cardiac procedure being planned or executed, processor 104 may prioritize certain TEE views 304. For instance, and without limitation, TEE view 304 may be pre-defined. For atrial fibrillation ablation, a TEE view 304 may emphasize visualization of the pulmonary veins' entrances into the left atrium (LA). In other cases, TEE view 304 may be automatically identified by processor 104, using one or more machine learning models as described herein, such as, without limitation, a synthetic TEE data generator as described in detail below.

With continued reference to FIG. 3, as used in this disclosure, a "synthetic TEE frame" refers to a digitally generated or simulated image that emulates a visual representation obtained from TEE view 304. In one or more embodiments, synthetic TEE frames 308 may be produced using computational methods and/or models such as, without limitation, a synthetic TEE data generator 312 based on pre-existing data, models, or simulations, e.g., identified TEE views 304. One or more image processing techniques and/or computer vision algorithms such as, without limitation, histogram equalization, adaptive filtering, edge detection (e.g., Canny or Sobel operators), contour extraction, and/or the like may be applied by processor 104 on segmented CT scans and/or 3D models based on identified TEE view 304. Synthetic TEE frame 308 may be rendered on a blank canvas or background that mimics the echogenicity of a TEE image according to extracted contours, wherein the extracted contours may be represented as bold lines and enhanced with shading to give depth. In one or more embodiments, synthetic TEE frame 308 may be validated and verified by overlaying synthetic TEE frame 308 onto the original TEE view 304 to ensure accuracy and resemblance.

Still referring to FIG. 3, in one or more embodiments, generating synthetic TEE frames 308 may include implementations of one or more aspects of "generative artificial intelligence," a type of AI that uses machine learning algorithms to create, establish, or otherwise generate data. Such data may include, without limitation, ultrasonic images that are similar to one or more provided training examples. In an embodiment, a machine learning module described herein may generate one or more generative machine learning models that are trained on one or more sets of CT scans and/or 3D models in TEE image view 304 as described above. Synthetic TEE data generator 312 may include one or more generative machine learning models configured to generate new examples similar to the training data of the one or more generative models but are not exact replicas; for instance, and without limitation, data quality or attributes of the generated examples may bear a resemblance to the training data provided to the one or more generative machine learning models, wherein the resemblance may pertain to underlying patterns, features, or structures found within the provided training data.

Still referring to FIG. 3, in one or more embodiments, generative machine learning models within synthetic TEE data generator may include one or more generative models. As described herein, "generative models" refers to statistical models of the joint probability distribution P(X,Y) on a given observable variable x, representing features or data that can be directly measured or observed (e.g., CT scans and/or 3D models derived from CT scans) and target variable y, representing the outcomes or labels that one or more generative models aim to predict or generate (e.g., synthetic TEE frames 308). In one or more embodiments, generative models may rely on Bayes' theorem to find joint probability; for instance, and without limitation, Naïve Bayes classifiers may be employed by the computing device to categorize input data such as, without limitation, CT scans and/or 3D models derived from CT scans into different views.

In a non-limiting example, and still referring to FIG. 3, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P (A/B)=P (B/A) P (A)=P (B), where P (A/B) is the probability of hypothesis A given data B also known as posterior probability; P (B/A) is the probability of data B given that the hypothesis A was true; P (A) is the probability of hypothesis A being true regardless of data also known as prior probability of A; and P (B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

Still referring to FIG. 3, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as P(X, Y)=P(Y)ΠiP(Xi | Y), wherein P(Y) may be the prior probability of the class, and P(X¿|Y) is the conditional probability of each feature given the class. One or more generative machine learning models containing Naïve Bayes classifiers may be trained on labeled training data, estimating conditional probabilities $P(X_i|Y)$ and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of TEE images based on CT scans and/or 3D models derived from CT scans (e.g., identified TEE views 304), wherein the models may be trained using training data containing a plurality of features of input data as described herein and/or the like correlated to a plurality of TEE views.

Still referring to FIG. 3, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIGS. 5-7.

With continued reference to FIG. 3, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 5 to distinguish between different categories e.g., real vs. fake, or states e.g., TRUE vs. FALSE within the context of generated data such as, without limitations, synthetic TEE frames 308, and/or the like. In some cases, processor 104 may implement one or more classification algorithms such as, without limitation, Support Vector Machines (SVM), Logistic Regression, Decision Trees, and/or the like to define decision boundaries.

In a non-limiting example, and still referring to FIG. 3, generator of GAN may be responsible for creating synthetic data that resembles real TEE images. In some cases, GAN may be configured to receive CT scans and/or 3D models derived from CT scans as input and generates corresponding examples of TEE images containing information describing anatomy in different TEE views. On the other hand, discriminator of GAN may evaluate the authenticity of the generated content by comparing it to true TEE images, for example, discriminator may distinguish between genuine and generated content and providing feedback to generator to improve the model performance. Additionally, or alternatively, GAN may include a conditional GAN as an extension of the basic GAN as described herein that allows for generation of TEE images using pre-existing CT scans and/or 3D models derived from CT scans based on certain conditions or labels. In standard GAN, generator may produce samples from random noise, while in a conditional GAN, generator may produce samples based on random noise and a given condition or label.

With continued reference to FIG. 3, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. 3, VAE may be used by processor 104 to model complex relationships between CT scans and/or 3D models derived from CT scans. In some cases, VAE may encode input data into a latent space, capturing example TEE images. Such encoding process may include learning one or more probabilistic mappings from observed CT scans and/or 3D models derived from CT scans to a lower-dimensional latent representation. Latent representation may then be decoded back into the original data space, therefore reconstructing the 3D models representing example TEE images. In some cases, such decoding process may allow VAE to generate new examples or variations that are consistent with the learned distributions.

Additionally, or alternatively, and still referring to FIG. 3, processor 104 may be configured to continuously monitor synthetic TEE data generator. In an embodiment, processor 104 may configure discriminator to provide ongoing feedback and further corrections as needed to subsequent input data. An iterative feedback loop may be created as processor 104 continuously receive real-time data, identify errors (e.g., distance between synthetic TEE frame 308 and real TEE images) as a function of real-time data, delivering corrections based on the identified errors, and monitoring subsequent model outputs and/or user feedback on the delivered corrections. In an embodiment, processor 104 may be configured to retrain one or more generative machine learning models within synthetic TEE data generator based on user modified TEE frames or update training data of one or more generative machine learning models within synthetic TEE data generator by integrating validated synthetic TEE frames (i.e., subsequent model output) into the original training data. In such embodiment, iterative feedback loop may allow synthetic TEE data generator to adapt to the user's needs and performance requirements, enabling one or more generative machine learning models described herein to learn and update based on user responses and generated feedback.

With continued reference to FIG. 3, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models that may be used generating synthetic TEE frames 308.

Still referring to FIG. 3, in a further non-limiting embodiment, synthetic TEE data generator 312 may be further configured to generate a multi-model neural network that combines various neural network architectures described herein. In a non-limiting example, multi-model neural network may combine LSTM for time-series analysis with GPT models for natural language processing. Such fusion may be applied by computing device to generate synthetic TEE frames 308. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models that may be used to generating synthetic TEE frames 308 as described herein. As an ordinary person skilled in the art, upon reviewing the entirety of this disclosure, will be aware of various multi-model neural network and combination thereof that may be implemented by apparatus 100 in consistent with this disclosure.

Figure 4:
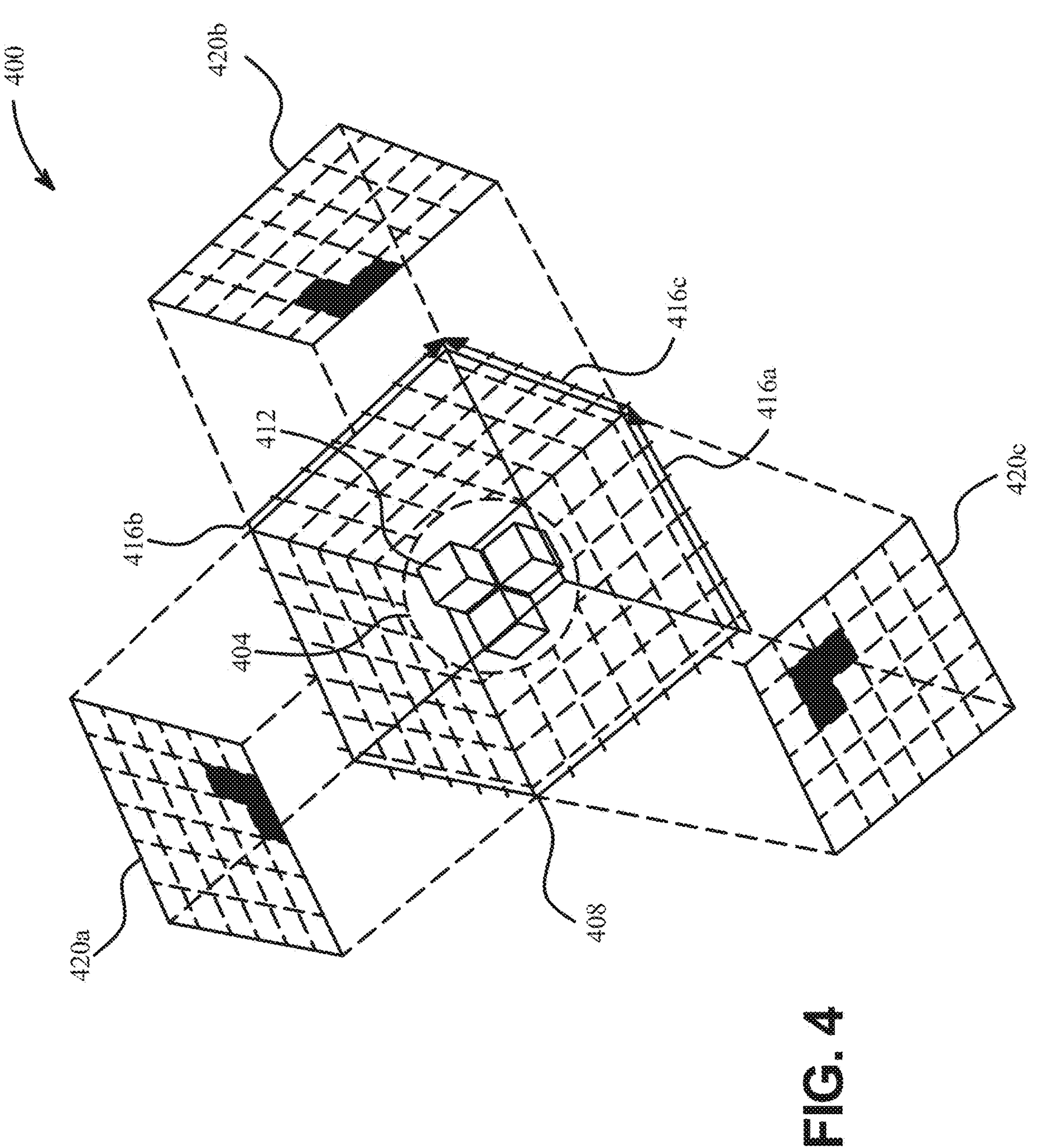
FIG. 4 illustrates an exemplary embodiment of a three-dimensional (3D) voxel occupancy representation.

Now referring to FIG. 4, an exemplary embodiment of a 3D VOR 400 is illustrated. 3D VOR 400 may be used to represent 3D object 404. In an embodiment, 3D VOR 400 may divide a 3D space 408 into a grid of one or more cubic units e.g., voxels 412, wherein each voxel 412 represents a specific volume within 3D space 408. In a non-limiting example, 3D object 404 may include a structure pertaining to a subject.

Still referring to FIG. 4, in one or more embodiments, each voxel 412 may act as a basic building block. In a non-limiting example, each voxel 412 may be configured to represent a discrete portion of 3D space 408. In an embodiment, each voxel 412 may include a presence indicator as described above with reference to FIG. 1, which denotes whether the voxel is occupied or unoccupied. In such embodiment, the binary or continuous value may allow 3D VOR 400 to map the presence or absence of material within each voxel 412, creating a granular representation of 3D object 404.

With continued reference to FIG. 4, in one or more embodiments, the resolution of 3D VOR 400 may be determined by the size and number of voxels within the grid. In a non-limiting example, smaller voxel may provide a higher resolution, capturing finer details, while larger voxels offer a more generalized representation.

Still referring to FIG. 4, in an embodiment, voxels 412 may be arranged in a regular pattern along three axis **416*a*, 416*b*, 416*c*, each pointing a distinct direction. In a non-limiting example, voxels 412 may be arranged along x, y, and z axes, wherein such arrangement may facilitate efficient manipulation and rendering of the 3D object 404. In one or more embodiments, spatial features 420*a*, 420*b*, 420*c* such as, without limitation, edges, surfaces, textures, and any other spatial features as described above with reference to FIG. 1, may be extracted from 3D VOR 400** by analyzing the relationships and patterns between neighboring voxels.

Figure 5:
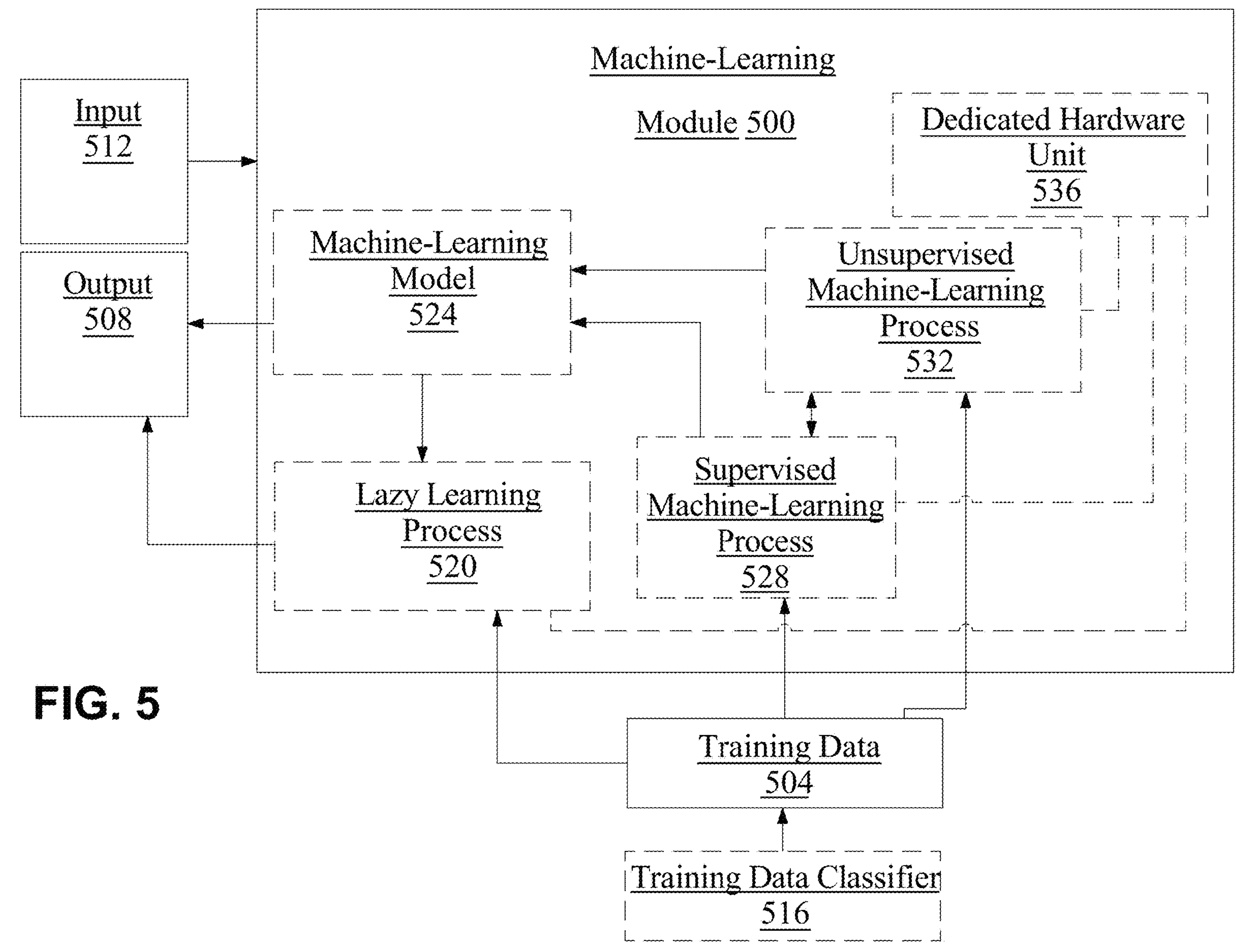
FIG. 5 is a block diagram of an exemplary machine-learning process.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, image sets may be correlated with plurality of CT-based 3D models as training data that may be used to train 3D modeling machine learning model as described above with reference to FIG. 1.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to at least one template model of plurality of template modules as described above with reference to FIG. 1.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data analyzed are represented by more training examples than values that are encountered less frequently. Alternatively or additionally, a set of training examples may be compared to a collection of representative values in a database and/or presented to a user, so that a process can detect, automatically or through user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators to take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be. Processor may interpolate the low pixel count image to convert the 100 pixels into pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In one or more embodiments, and with continued reference to FIG. 5, computing device, processor, and/or module may down-sample elements of a training example to a desired lower number of data elements. As a non-limiting example, a high pixel count image may have 256 pixels, however a desired number of pixels may be. Processor may down-sample the high pixel count image to convert the 256 pixels into pixels. In one or more embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean upside-effects of compression.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively, or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created through the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include a plurality of image sets as described above as inputs, a plurality of shape parameter sets as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation, gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively, or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including, without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any current or previously deployed version of a machine-learning model and/or algorithm as a starting point. Training data for retraining may be collected, preconditioned, sorted, classified, sanitized, or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
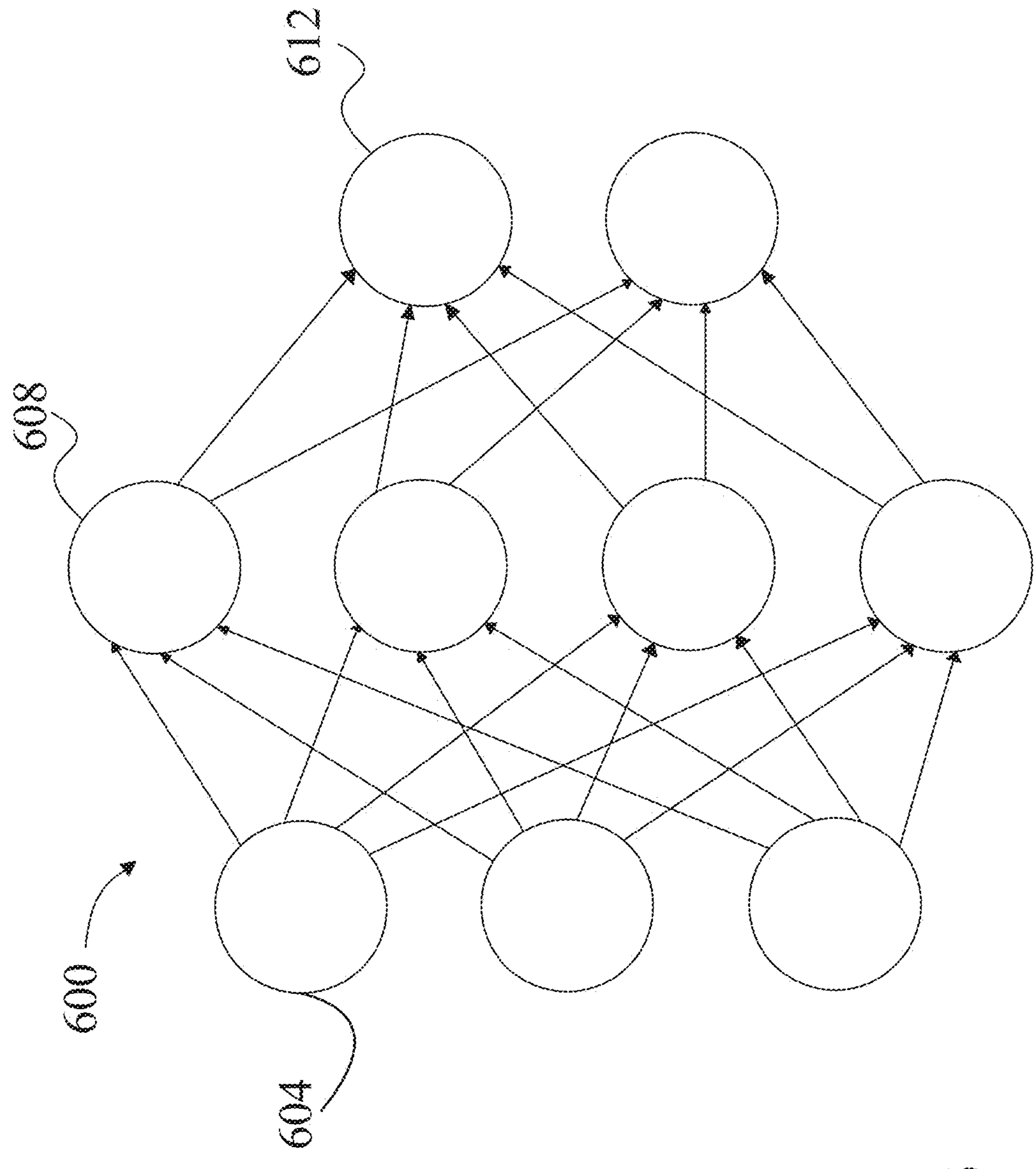
FIG. 6 is a diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created through the process of "training" the network, in which elements from a training data set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network including an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 7:
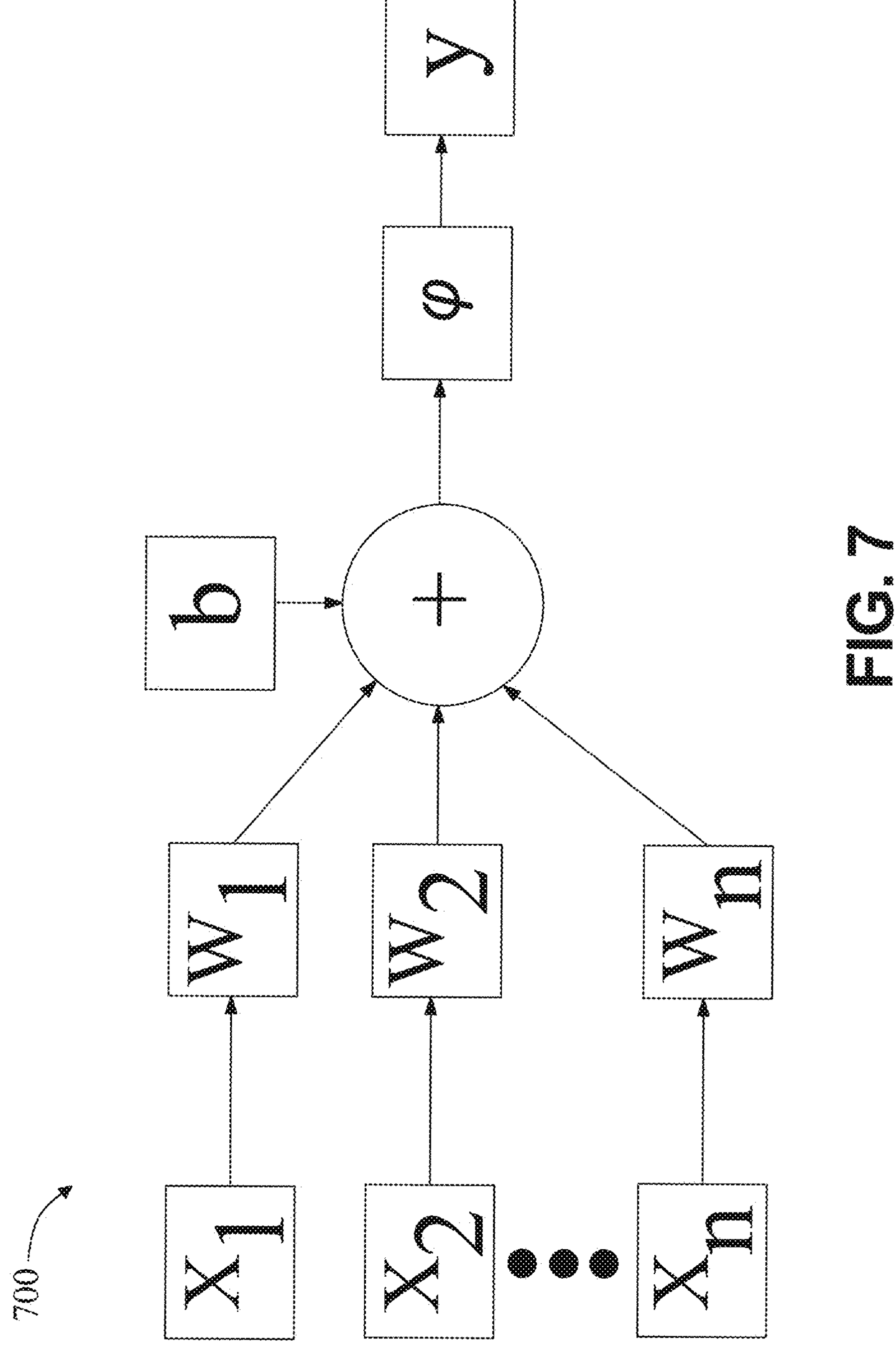
FIG. 7 is a diagram of an exemplary embodiment of a node of a neural network.

Referring now to FIG. 7, an exemplary embodiment of a node 700 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as f(x)=max (0, x), a "leaky" and/or "parametric" rectified linear unit function such as f(x)=max (ax, x) for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in one or more embodiments), a softmax function such as $$f(x_i) = \frac{e^x}{\sum_i x_i}$$

where the inputs to an instant layer are $x_i$, a swish function such as f(x)=x*sigmoid(x), a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0. \\ x & \text{for } x \geq 0 \end{cases}$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
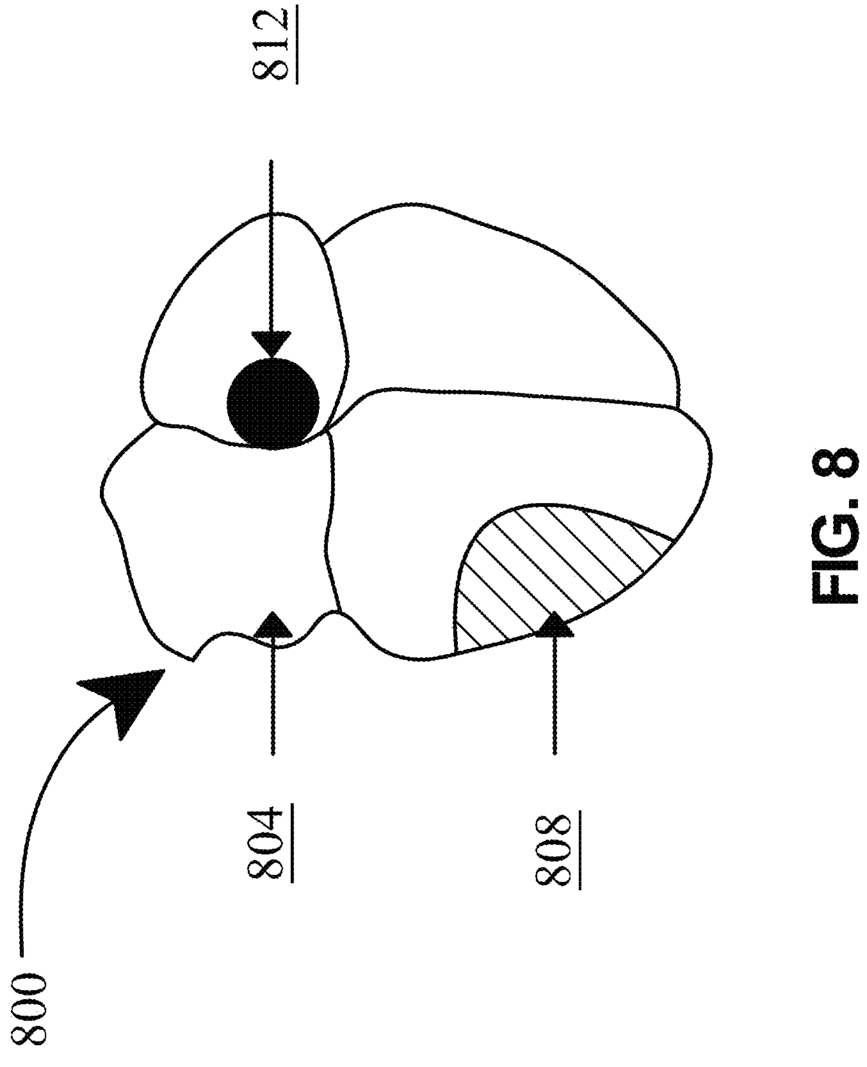
FIG. 8 is a diagram illustrating an exemplary embodiment of an overlaid heat map.

Now referring to FIG. 8, an exemplary embodiment of an overlaid heat map 800 is illustrated. Heat map 800 may include map embodiments as described in FIG. 1. Heat map 800 may illustrate one or more of levels of uncertainty differentiated by color, shading, texture, and the like as described above. For example, heat map 800 may depict a first level of uncertainty 804, wherein a first level may represent, in one or more embodiments, a high percentage of certainty and/or accuracy, in the depiction of a shape parameter, location, geometric identifier and the like. Heat map 800 may depict a second level of uncertainty 808, wherein a second level may represent, in one or more embodiments, a lower percentage of certainty and/or accuracy than first level of uncertainty 804. Additionally, Heat map 800 may depict a third level of uncertainty 812, wherein a third level may represent a lower percentage of certainty and/or accuracy than first level of uncertainty 804 and second level of uncertainty 808. The depictions of each level of uncertainty may be scaled based on color code/texture code-based scales as described above. For example, first level of uncertainty 804 may include a light shading of an area of the 3D model, wherein as the level of uncertainty progress, the shading darkens as in third level of uncertainty 812.

Figure 9:
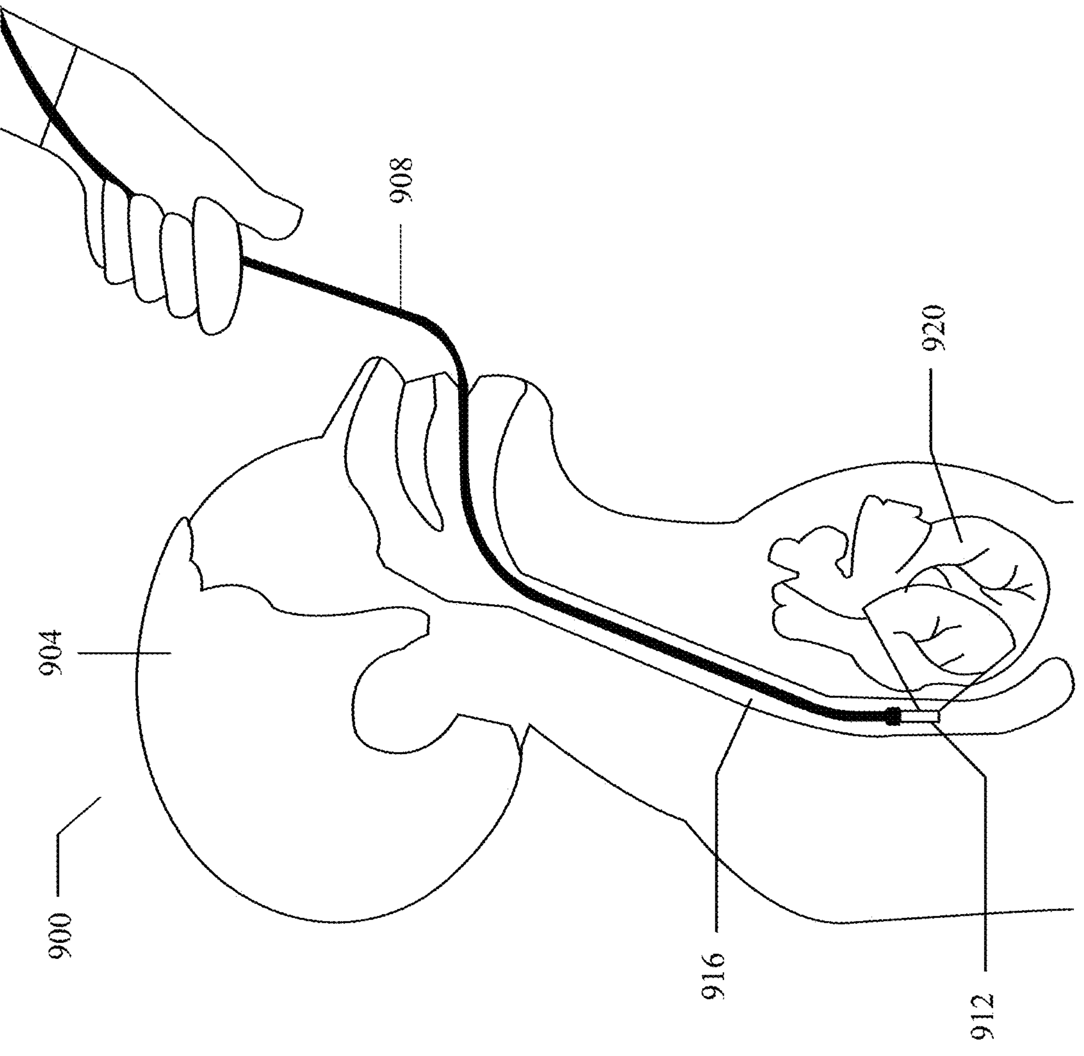
FIG. 9 is a schematic diagram of an exemplary transesophageal echocardiogram.

Now referring to FIG. 9, a schematic of an exemplary transesophageal echocardiogram (TEE) procedure 900 is shown. In one or more embodiments, TEE procedure 900 may be performed during another procedure, for instance heart surgery. According to some embodiments, a patient 904 has an endoscope 908, with an ultrasonic transducer 912, inserted into his esophagus 916. As one's esophagus 916 is proximal one's heart 920, ultrasonic transducer 912 may generate echocardiograms.

Still referring to FIG. 9, in one or more embodiments, transesophageal echocardiography (TEE) may provide superior imaging quality than intracardiac echocardiography (ICE), as larger ultrasound transducers 912 may be placed within the esophagus 916 than within heart 920. In one or more embodiments, ultrasound transducers must be substantially miniaturised to fit within heart 920, as in ICE catheters. As esophagus 916 may be proximal to heart 920, TEE may provide a clear image of various heart structures without needing vascular access (as commonly required by ICE). Additionally, TEE may be performed without obstructing patient's 904 ribcage and intermediary tissues (as commonly required by transthoracic echocardiography [TTE]). In one or more embodiments, TEE images may also provide information associated with angle of acquisition. Angle of acquisition may be an angle of TEE probe with respect to esophagus 916 (e.g., esophageal axis).

Still referring to FIG. 9, in one or more embodiments, TEE echocardiogram data, including images showing heart structures and, in one or more embodiments, angle of acquisition, may be used as input to any machine learning process described in this application, for instance with reference to FIGS. 1-8, and 9. For instance TEE echocardiogram data may be used to reconstruct 3D heart models. In one or more embodiments, TEE echocardiogram data is input into a machine learning model that outputs a 3D heart model (e.g., 3D mesh model and/or statistical shape model).

Still referring to FIG. 9, in one or more embodiments, TEE may be a preferred imaging modality for structural heart interventions, such as without limitation left atrial appendage occlusion (LAOO), aortic, tricuspid and/or other heart valve replacement procedures as described in this disclosure. In one or more embodiments, technology and improvements described in this disclosure permit creation and/or modification of a 3D heart mesh from TEE data to aid in planning implant size selection, as well as to guide implantation procedures. In one or more embodiments, virtual placement of a 3D model of a candidate implant (such as without limitation LAAO device and/or heart valve implants) can be simulated on a 3D heart model generated by any method described in this disclosure. This novel and improved functionality may validate appropriate size and placement of implants within heart 920, as well as other organs within body of patient 904. For example, in the context of electrophysiology procedures, TEE procedure 900 can be used to create heart anatomical models that can be used as reference for electroanatomic mapping, and guidance of ablation catheters for atrial fibrillation procedures (such as without limitation pulmonary vein isolation).

Still referring to FIG. 9, in one or more embodiments, applications described with reference to TEE procedure 900 above can be extended for use with TTE and point of care ultrasound (POCUS). In one or more embodiments, both TTE and POCUS may acquire ultrasound images of chest/surface of patient 904. In one or more embodiments, TTE and POCUS data may be used as an input (and/or training data) for any machine learning process described in this disclosure, for instance with reference to FIGS. 1-8 and 9. In one or more embodiments, use of TTE and/or POCUS data (in machine learning processes described in this disclosure) may require adjustment in ultrasound acquisition parameters and positions to acquire a sufficient number of frames for 3D reconstruction. In one or more embodiments, TTE and POCUS offer improved accessibility (with POCUS being portable/mobile as well) and non-invasive 3D heart modeling, often without anesthesia or sedation, compared to catheterized 3D heart modeling commonly performed today for electroanatomical mapping and ablation procedures. This may be implemented with reference to FIGS. 1-9 and without limitation.

Figure 10A:
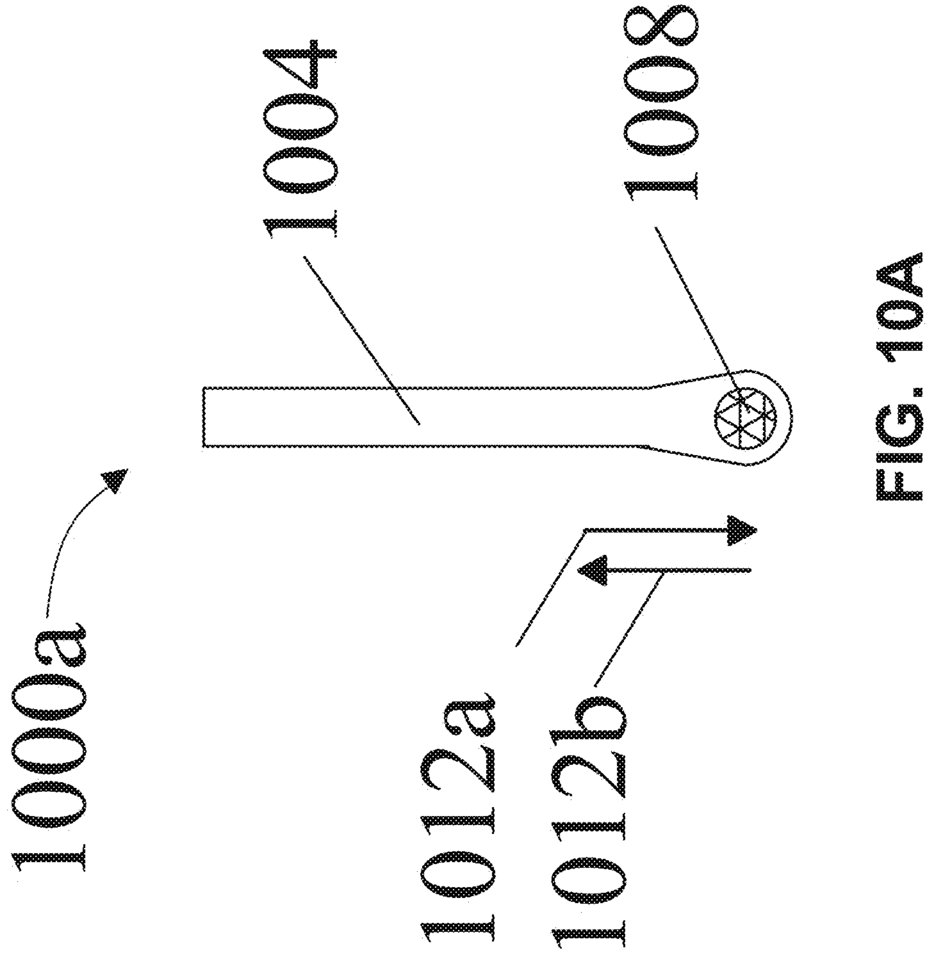
FIG. 10A is an exemplary illustration of a front view of at least a TEE probe with at least a transducer in a withdraw and an advance movement.

Referring now to FIG. 10A, an exemplary illustration 1000*a* of a front view of at least a TEE probe with at least a transducer in a withdraw and an advance movement. In an embodiment, the illustration 1000*a* may include at least a TEE probe 1004. In an embodiment, the illustration 1000*a* may include at least a transducer 1008. In an embodiment, the illustration 1000*a* may include a withdraw and an advance movement 1012*a*-*b* of the at least a TEE probe 1004. As used in this disclosure, an "advance movement" is the forward motion of a TEE probe. In an embodiment, the advance movement 1012*a* may include the at least a TEE probe 1004 inserted deeper into the esophagus or stomach to capture imaging from different anatomical perspectives. Continuing, the advance movement 1012*a* may allow for visualization of deeper structures, such as the transgastric short-axis view of the heart, where the probe is positioned in the stomach to obtain high-resolution images of the ventricles and outflow tracts. As used in this disclosure, a "withdraw movement" is the backward motion of a TEE probe 1004. In an embodiment, the withdraw movement 1012*b* may include the at least a TEE probe 1004 being retracted toward the upper esophagus to obtain imaging from a different set of views. The withdraw movement 1012*b* may enable imaging from higher esophageal positions, such as the mid-esophageal four-chamber view, which provides a comprehensive look at the atria, ventricles, and valve structures.

Figure 10B:
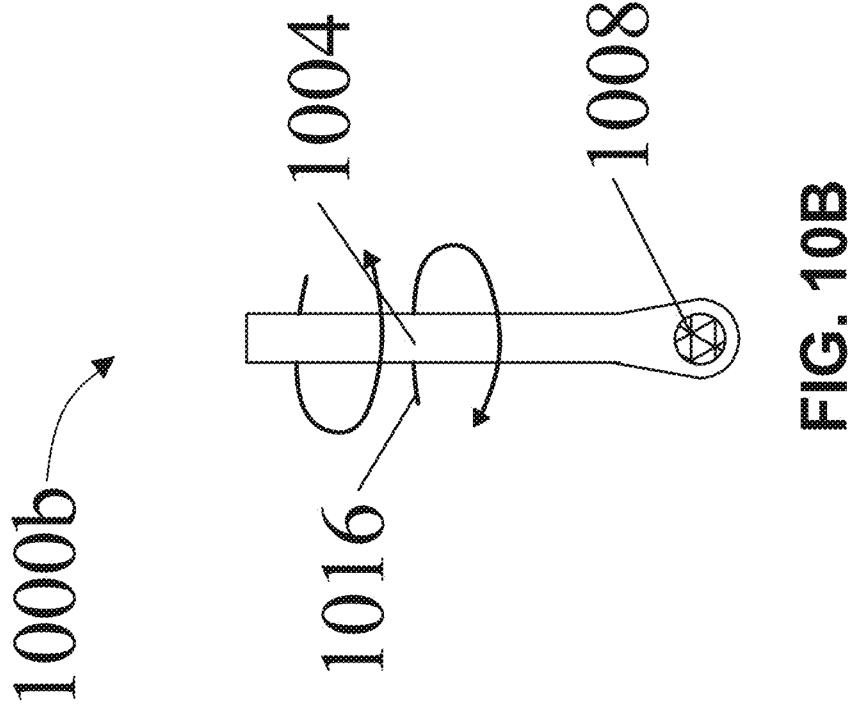
FIG. 10B is an exemplary illustration of a front view of at least a TEE probe with at least a transducer in a turning movement.

Referring now to FIG. 10B, an exemplary illustration 1000*b* of a front view of at least a TEE probe with at least a transducer in a turning movement. In an embodiment, the illustration 1000*b* may include at least a TEE probe 1004. In an embodiment, the illustration 1000*b* may include at least a transducer 1008. In an embodiment, the illustration 1000*b* may include a turning movement 1016 of the at least a TEE probe 1004. As used in this disclosure, a "turning movement" is the twisting motion of a TEE probe and/or its transducer around its longitudinal axis. In an embodiment, the turning movement 1016 may be used to adjust the imaging angle and obtain different cross-sectional views of a structure. The turning movement 1016 may allow for controlled rotation of the at least a transducer 1008 to optimize visualization of anatomical features without advancing or withdrawing the TEE probe 1004. Without limitation, the turning movement 1016 may facilitate transitions between standard echocardiographic planes, such as rotating from a mid-esophageal four-chamber view to a mid-esophageal long-axis view, providing additional perspectives for diagnostic assessment and procedural guidance.

Figure 10C:
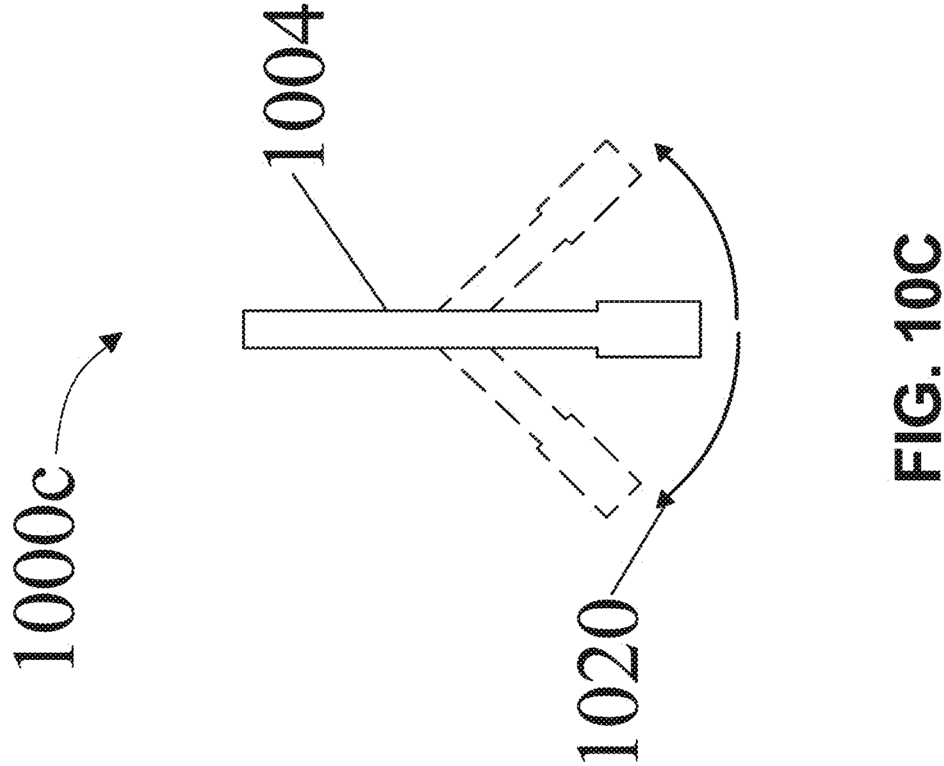
FIG. 10C is an exemplary illustration of a side view of at least a transducer in a retroflex and an anteflex movement.

Referring now to FIG. 10C, an exemplary illustration 1000*c* of a side view of at least a transducer in a retroflex and an anteflex movement. In an embodiment, the illustration 1000*c* may include at least a TEE probe 1004. In an embodiment, the illustration 1000*c* may include at least a transducer 1008. In an embodiment, the illustration 1000*c* may include a retroflex and an anteflex movement 1020 of the at least a TEE probe 1004. As used in this disclosure, a "retroflex movement" is the backward bending or angulation of a TEE probe tip. In an embodiment, the retroflex movement0 may move the TEE probe 1004 tip the toward the esophagus or stomach wall and may adjust the imaging angle and enhance visualization of posterior structures. Without limitation, the retroflex movement0 may be used to obtain views such as the transgastric long-axis view, where the TEE probe 1004 tip is flexed to better align with the left ventricular outflow tract and aortic valve. As used in this disclosure, an "anteflex movement" the forward bending or angulation of a TEE probe tip. In an embodiment, the anteflex movement0 may include moving the TEE probe 1004 tip toward the anterior aspect of the body to capture imaging of structures located more anteriorly in the chest. Without limitation, the anteflex movement0 may assist in optimizing imaging of structures such as the mitral valve and left ventricular apex, particularly when performing detailed assessments of valvular function or guiding interventional procedures.

Figure 10D:
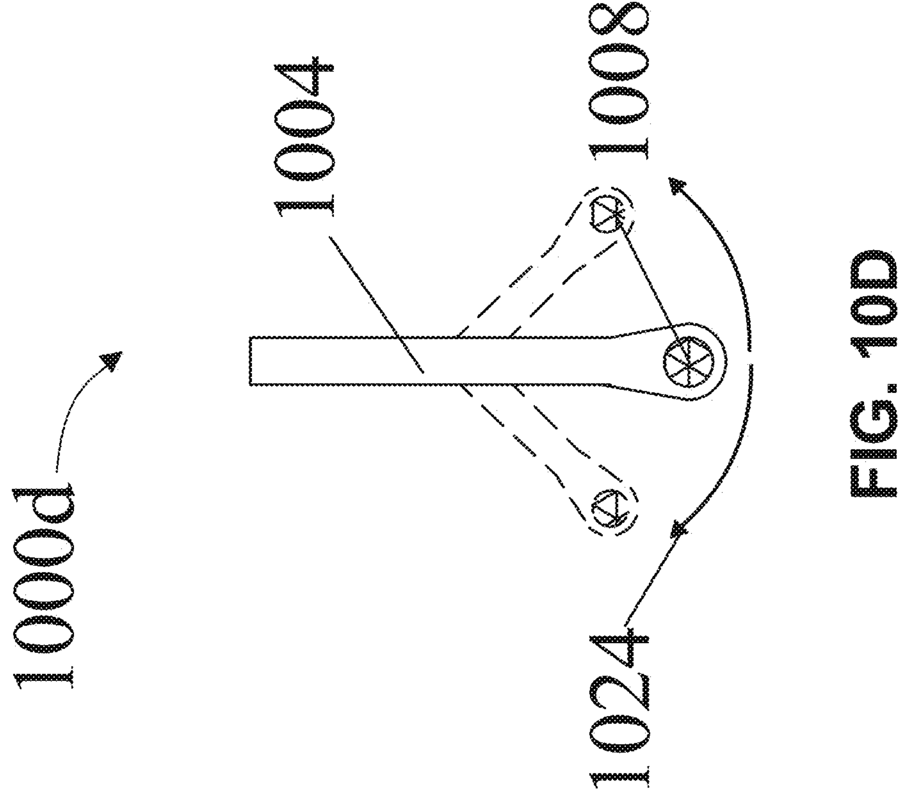
FIG. 10D is an exemplary illustration of a front view of at least a TEE probe with at least a transducer in a left flex and a right flex movement.

Referring now to FIG. 10D, an exemplary illustration 1000*d* of a front view of at least a TEE probe with at least a transducer in a left flex and a right flex movement. In an embodiment, the illustration 1000*d* may include at least a TEE probe 1004. In an embodiment, the illustration 1000*d* may include at least a transducer 1008. In an embodiment, the illustration 1000*c* may include a left flex and a right flex movement 1024 of the at least a TEE probe 1004. As used in this disclosure, a "left flex movement" may refer to the lateral bending or angulation of a TEE probe tip. In an embodiment, the left flex movement may move the TEE probe 1004 tip toward the left side of the subject's body to adjust the imaging plane and optimize visualization of cardiac structures. The left flex movement may be used to enhance imaging of the mitral valve, particularly when obtaining oblique or off-axis views for more comprehensive diagnostic assessments. As used in this disclosure, a "right flex movement" is the lateral bending or angulation of a TEE probe tip. In an embodiment, the right flex movement 1024 may move the TEE probe 1004 tip toward the right side of the subject's body to modify the imaging orientation and improve visualization of structures positioned more to the right. The right flex movement 1024 may assist in capturing views of the right atrium, right ventricle, and tricuspid valve, enabling better assessment of right-sided heart function and potential abnormalities.

Figure 10E:
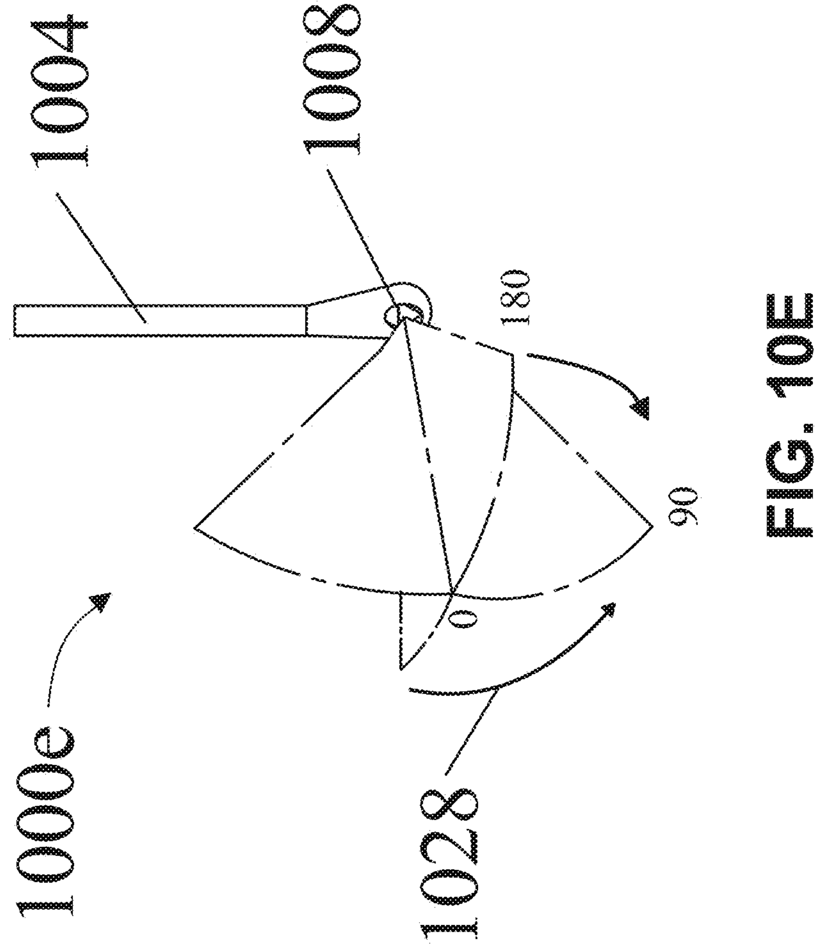
FIG. 10E is an exemplary illustration of an isometric view of at least a TEE probe with at least a transducer degrees of freedom.

Referring now to FIG. 10E, an exemplary illustration 1000*e* of an isometric view of at least a TEE probe with at least a transducer and degrees of freedom of movement. In an embodiment, the illustration 1000*e* may include at least a TEE probe 1004. In an embodiment, the illustration 1000*e* may include at least a transducer 1008. In an embodiment, the illustration 1000*e* may include a rotating movement 1028 of the at least a TEE probe 1004. As used in this disclosure, "degrees of freedom of movement" is the independent directions in which a TEE probe or its transducer may be maneuvered. In an embodiment, the degrees of freedom of movement 1028 may include advance movement (insertion), withdraw movement (retraction), retroflex movement (backward bending), anteflex movement (forward bending), left flex movement (lateral bending to the left), right flex movement (lateral bending to the right), and rotation movement (twisting around the longitudinal axis). Without limitation, these controlled movements may allow for precise positioning of the at least a transducer 1008 to acquire optimal ultrasound images of anatomical structures, such as the heart, from multiple perspectives.

Figure 11:
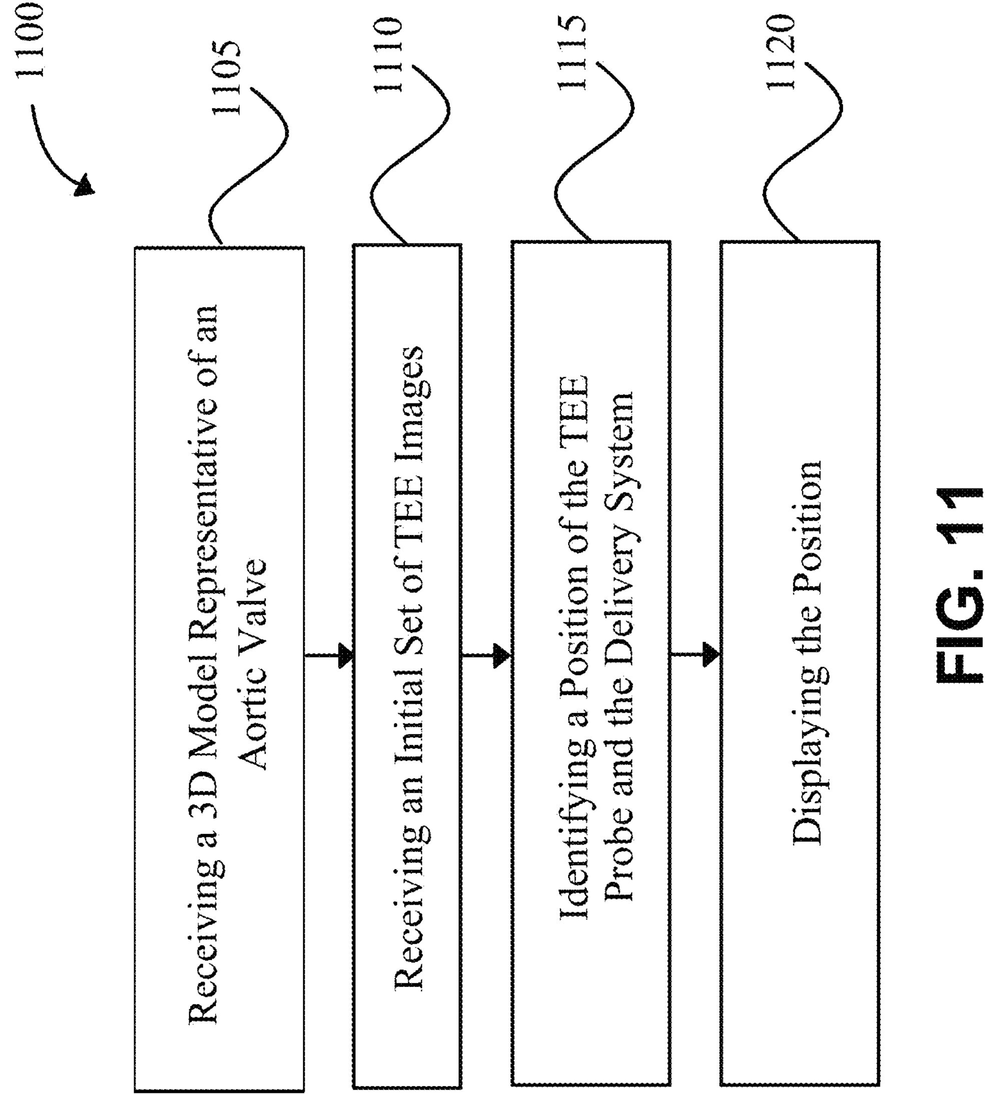
FIG. 11 is a flow diagram illustrating an exemplary embodiment of a method localization associated with mitral valve intervention.

Referring now to FIG. 11, an exemplary embodiment of a method 1100 for localization associated with aortic valve repair using transesophageal echocardiography is described. At step 1105, method 1100 includes receiving, by at least a processor, a 3D model representative of an aortic valve. This may be implemented with reference to FIGS. 1-10 and without limitation.

With continued reference to FIG. 11, at step 1110, method 1100 includes receiving, by the at least a processor and a transesophageal echocardiography (TEE) probe, an initial set of TEE images wherein the TEE probe is configured to capture TEE images of the aortic valve pertaining to a subject and the TEE probe is further configured to capture a delivery system, wherein the delivery system includes a delivery catheter configured for aortic valve repair. In one or more embodiments, delivery system may include a prosthetic device. In one or more embodiments, prosthetic device may be situated at a distal end of the delivery catheter. In one or more embodiments, the delivery system is located within a field of view of the TEE probe. This may be implemented with reference to FIGS. 1-10 and without limitation.

With continued reference to FIG. 11, at step 1115, method 1100 includes identifying, by the at least a processor, a position of the TEE probe and the delivery system by identifying anatomical landmarks within the initial set of TEE images and locating the position of the TEE probe and the delivery system relative to the anatomical landmarks. This may be implemented with reference to FIGS. 1-10 and without limitation.

With continued reference to FIG. 11, at step 1120, method 1100 includes displaying, by the at least a processor, the position of the delivery system relative to the 3D model.

With continued reference to FIG. 11, in one or more embodiments, receiving the 3D model includes, generating, using a 3D reconstruction model, the 3D model. In one or more embodiments, receiving the 3D model includes determining a valve model datum as a function of the 3D model, wherein the valve model datum includes information associated with at least a dimension of the prosthetic device for implantation at or near the aortic valve. In one or more embodiments, receiving the 3D model further includes identifying a valve model as a function of the valve model datum, wherein the valve model is representative of the prosthetic device. In one or more embodiments, displaying the position of the delivery system relative to the 3D model includes superimposing the valve model onto the 3D model to create a superimposed model and displaying the superimposed model. In one or more embodiments, prosthetic device includes an annuloplasty ring designed to repair an aortic annulus of the aortic valve. In one or more embodiments, the prosthetic device includes a mechanical valve configured to replace the aortic valve. In one or more embodiments, displaying the position of the delivery system relative to the 3D model includes displaying a path model for implantation of the prosthetic device within a heart of the subject. In one or more embodiments, the initial set of TEE images includes a real-time feed of image data being iteratively received from the TEE probe. In one or more embodiments, receiving the valve model includes identifying one or more anomalies within the initial set of TEE images and selecting at least one valve model from a plurality of valve models as a function of the one or more anomalies. This may be implemented with reference to FIGS. 1-10 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 12:
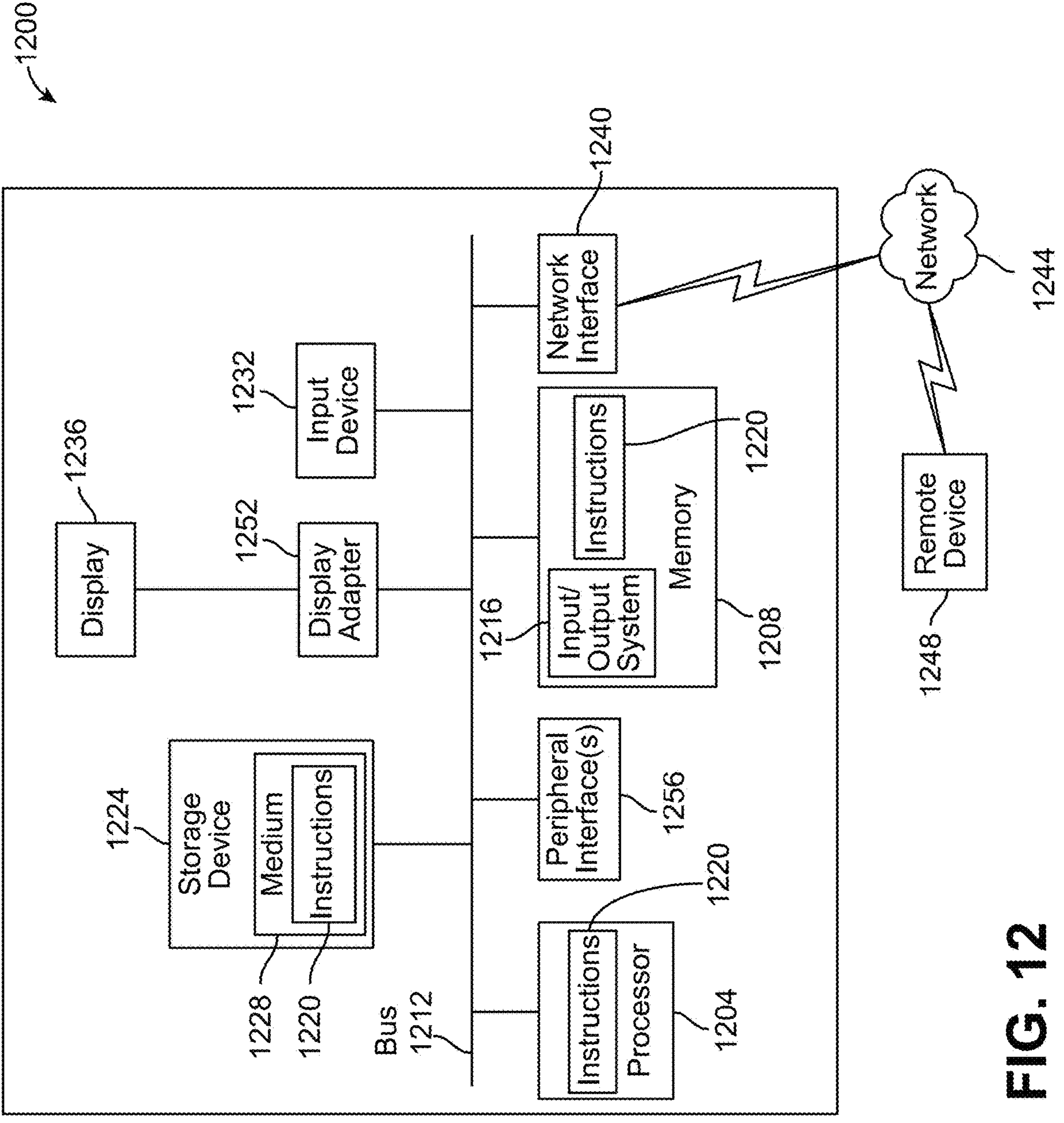
FIG. 12 is a block diagram of a computing system that can be used to implement any one or more of the methodologies disclosed herein and any one or more portions thereof.

FIG. 12 shows a diagrammatic representation of one embodiment of a computing device in the exemplary form of a computer system 1200 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1200 includes a processor 1204 and a memory 1208 that communicate with each other, and with other components, via a bus 1212. Bus 1212 may include any of several types of bus structures including, but not limited to, a memory bus, a memory controller, a peripheral bus, a local bus, and any combinations thereof, using any of a variety of bus architectures.

Processor 1204 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1204 may be organized according to Von Neumann and/or Harvard architecture as a non-limiting example. Processor 1204 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 1208 may include various components (e.g., machine-readable media) including, but not limited to, a random-access memory component, a read only component, and any combinations thereof. In one example, a basic input/output system 1216 (BIOS), including basic routines that help to transfer information between elements within computer system 1200, such as during start-up, may be stored in memory 1208. Memory 1208 may also include (e.g., stored on one or more machine-readable media) instructions (e.g., software) 1220 embodying any one or more of the aspects and/or methodologies of the present disclosure. In another example, memory 1208 may further include any number of program modules including, but not limited to, an operating system, one or more application programs, other program modules, program data, and any combinations thereof.

Computer system 1200 may also include a storage device 1224. Examples of a storage device (e.g., storage device 1224) include, but are not limited to, a hard disk drive, a magnetic disk drive, an optical disc drive in combination with an optical medium, a solid-state memory device, and any combinations thereof. Storage device 1224 may be connected to bus 1212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1224 (or one or more components thereof) may be removably interfaced with computer system 1200 (e.g., via an external port connector (not shown)). Particularly, storage device 1224 and an associated machine-readable medium 1228 may provide nonvolatile and/or volatile storage of machine-readable instructions, data structures, program modules, and/or other data for computer system 1200. In one example, software 1220 may reside, completely or partially, within machine-readable medium 1228. In another example, software 1220 may reside, completely or partially, within processor 1204.

Computer system 1200 may also include an input device 1232. In one example, a user of computer system 1200 may enter commands and/or other information into computer system 1200 via input device 1232. Examples of an input device 1232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1232 may be interfaced to bus 1212 via any of a variety of interfaces (not shown) including, but not limited to, a serial interface, a parallel interface, a game port, a USB interface, a FIREWIRE interface, a direct interface to bus 1212, and any combinations thereof. Input device 1232 may include a touch screen interface that may be a part of or separate from display 1236, discussed further below. Input device 1232 may be utilized as a user selection device for selecting one or more graphical representations in a graphical interface as described above.

A user may also input commands and/or other information to computer system 1200 via storage device 1224 (e.g., a removable disk drive, a flash drive, etc.) and/or network interface device 1240. A network interface device, such as network interface device 1240, may be utilized for connecting computer system 1200 to one or more of a variety of networks, such as network 1244, and one or more remote devices 1248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1244, may employ a wired and/or a wireless mode of communication. In general, any network topology may be used. Information (e.g., data, software 1220, etc.) may be communicated to and/or from computer system 1200 via network interface device 1240.

Computer system 1200 may further include a video display adapter 1252 for communicating a displayable image to a display device, such as display 1236. Examples of a display device include, but are not limited to, a liquid crystal display (LCD), a cathode ray tube (CRT), a plasma display, a light emitting diode (LED) display, and any combinations thereof. Display adapter 1252 and display 1236 may be utilized in combination with processor 1204 to provide graphical representations of aspects of the present disclosure. In addition to a display device, computer system 1200 may include one or more other peripheral output devices including, but not limited to, an audio speaker, a printer, and any combinations thereof. Such peripheral output devices may be connected to bus 1212 via a peripheral interface 1256. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for localization associated with aortic valve repair using transesophageal echocardiography, wherein the apparatus comprises:

a transesophageal echocardiography (TEE) probe configured to capture TEE images of an aortic valve pertaining to a subject;

a delivery system comprising:

a delivery catheter, wherein the delivery catheter is configured to perform aortic valve repair; and a computing device configured to:

receive a three-dimensional (3D) model representative of the aortic valve and an initial set of TEE images from the TEE probe, wherein receiving the 3D model comprises:

determining a valve model datum as a function of the 3D model, wherein the valve model datum comprises information associated with at least a dimension of a prosthetic device configured for implantation at or near the aortic valve; and determining a valve model as a function of the valve model datum, wherein the valve model is representative of the prosthetic device, wherein determining the valve model comprises:

identifying one or more anomalies within the initial set of TEE images; and selecting at least one valve model from a plurality of valve models as a function of the one or more anomalies;

identify a position of the TEE probe and the delivery system by:

identifying anatomical landmarks within the initial set of TEE images; and locating the position of the TEE probe and the delivery system relative to the anatomical landmarks; and display the position of the delivery system relative to the 3D model.

2. The apparatus of claim 1, wherein receiving the 3D model comprises, generating, using a 3D reconstruction model, the 3D model as a function of the TEE images captured from the TEE probe.

3. The apparatus of claim 1, wherein displaying the position of the delivery system relative to the 3D model comprises:

superimposing the valve model onto the 3D model to create a superimposed model; and displaying the superimposed model.

4. The apparatus of claim 1, wherein the delivery system further comprises the prosthetic device and wherein the prosthetic device comprises an annuloplasty ring designed to repair an aortic annulus of the aortic valve.

5. The apparatus of claim 1, wherein the delivery system further comprises the prosthetic device and wherein the prosthetic device comprises a mechanical valve configured to replace the aortic valve.

6. The apparatus of claim 1, wherein displaying the position of the delivery system relative to the 3D model comprises displaying a path model for implantation of the prosthetic device within a heart of the subject.

7. The apparatus of claim 1, wherein the initial set of TEE images comprises a real-time feed of image data being iteratively received from the TEE probe.

8. A method for localization associated with aortic valve repair using transesophageal echocardiography, the method comprising:

receiving, by at least a processor, a three-dimensional (3D) model representative of an aortic valve and, by a transesophageal echocardiography (TEE) probe, an initial set of TEE images, wherein:

receiving the 3D model comprises:

determining a valve model datum as a function of the 3D model, wherein the valve model datum comprises information associated with at least a dimension of a prosthetic device configured for implantation at or near the aortic valve; and determining a valve model as a function of the valve model datum, wherein the valve model is representative of the prosthetic device, wherein determining the valve model comprises:

identifying one or more anomalies within the initial set of TEE images; and selecting at least one valve model from a plurality of valve models as a function of the one or more anomalies; and the TEE probe is configured to capture TEE images of the aortic valve pertaining to a subject;

providing a delivery system comprising a delivery catheter configured to perform aortic valve repair;

identifying, by the at least a processor, a position of the TEE probe and the delivery system by:

identifying anatomical landmarks within the initial set of TEE images; and locating the position of the TEE probe and the delivery system relative to the anatomical landmarks; and displaying, by the at least a processor, the position of the delivery system relative to the 3D model.

9. The method of claim 8, wherein receiving the 3D model comprises, generating, using a 3D reconstruction model, the 3D model as a function of the TEE images captured from the TEE probe.

10. The method of claim 1, wherein displaying the position of the delivery system relative to the 3D model comprises:

superimposing the valve model onto the 3D model to create a superimposed model; and displaying the superimposed model.

11. The method of claim 8, wherein the delivery system further comprises the prosthetic device and wherein the prosthetic device comprises an annuloplasty ring designed to repair an aortic annulus of the aortic valve.

12. The method of claim 8, wherein the delivery system further comprises the prosthetic device and wherein the prosthetic device comprises a mechanical valve configured to replace the aortic valve.

13. The method of claim 8, wherein displaying the position of the delivery system relative to the 3D model comprises displaying a path model for implantation of the prosthetic device within a heart of the subject.

14. The method of claim 8, wherein the initial set of TEE images comprises a real-time feed of image data being iteratively received from the TEE probe.

* * * * *